(12) United States Patent
Tabuteau

(10) Patent No.: US 11,110,173 B2
(45) Date of Patent: *Sep. 7, 2021

(54) PHARMACEUTICAL COMPOSITIONS COMPRISING MELOXICAM

(71) Applicant: AXSOME THERAPEUTICS, INC., New York, NY (US)

(72) Inventor: Herriot Tabuteau, New York, NY (US)

(73) Assignee: AXSOME THERAPEUTICS, INC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/067,006

(22) Filed: Oct. 9, 2020

(65) Prior Publication Data

US 2021/0030876 A1 Feb. 4, 2021

Related U.S. Application Data

(63) Continuation-in-part of application No. 16/842,063, filed on Apr. 7, 2020, now Pat. No. 10,799,588, which is a continuation-in-part of application No. 16/694,440, filed on Nov. 25, 2019, now Pat. No. 10,702,602, which is a continuation-in-part of application No. 16/565,111, filed on Sep. 9, 2019, now Pat. No. 10,532,101, which is a continuation-in-part of application No. 16/372,977, filed on Apr. 2, 2019, now Pat. No. 10,426,839, which is a continuation of application No. 15/988,104, filed on May 24, 2018, now Pat. No. 10,265,400, which is a continuation of application No. 15/902,770, filed on Feb. 22, 2018, now Pat. No. 10,029,010, which is a continuation of application No. 15/797,955, filed on Oct. 30, 2017, now Pat. No. 10,058,614, which is a continuation-in-part of application No. 15/132,130, filed on Apr. 18, 2016, now Pat. No. 9,821,075, which is a continuation of application No. PCT/US2016/026991, filed on Apr. 11, 2016.

(60) Provisional application No. 62/259,993, filed on Nov. 25, 2015, provisional application No. 62/526,884, filed on Jun. 29, 2017, provisional application No. 62/536,466, filed on Jul. 25, 2017, provisional application No. 62/114,215, filed on Feb. 10, 2015.

(51) Int. Cl.
| | |
|---|---|
| A61K 47/02 | (2006.01) |
| A61K 31/5415 | (2006.01) |
| A61K 31/4439 | (2006.01) |
| A61K 9/00 | (2006.01) |
| A61K 45/06 | (2006.01) |
| A61K 47/40 | (2006.01) |
| A61K 9/20 | (2006.01) |
| A61K 47/69 | (2017.01) |
| C08B 37/16 | (2006.01) |

(52) U.S. Cl.
CPC ............ *A61K 47/02* (2013.01); *A61K 9/0053* (2013.01); *A61K 9/2009* (2013.01); *A61K 31/4439* (2013.01); *A61K 31/5415* (2013.01); *A61K 45/06* (2013.01); *A61K 47/40* (2013.01); *A61K 47/6951* (2017.08); *C08B 37/0012* (2013.01); *C08B 37/0015* (2013.01)

(58) Field of Classification Search
CPC ................ A61K 31/5415; A61K 47/02; A61K 31/4439; A61K 9/2009; A61K 45/06; C08B 37/0015; C08B 37/0012
See application file for complete search history.

(56) References Cited

U.S. PATENT DOCUMENTS

| | | | |
|---|---|---|---|
| 4,233,299 A | 11/1980 | Trummlitz et al. | |
| 5,872,145 A | 2/1999 | Plachetka | |
| 6,060,499 A | 5/2000 | Plachetka | |

(Continued)

FOREIGN PATENT DOCUMENTS

| | | |
|---|---|---|
| CA | 2565941 A1 | 11/2005 |
| CN | 101984960 A | 3/2011 |

(Continued)

OTHER PUBLICATIONS

Lainez, M. in Neuropsychiatric Disease and Treatment, 2(3) 247-259 (2006) (Year: 2006).*

'Meloxicam' at http://web.archive.org/web/20141113013539/ https://www.mayoclinic .org/drugs-supplements/meloxicam-oral-route/proper-use/drg-20066928 (Year: 2014).*

Hu et al., Predicting Biological Functions of Compounds Based on Chemical-Chemical Interactions, PLoS One, 6(12), Dec. 2011, 9 pgs.

(Continued)

*Primary Examiner* — Dennis Heyer
(74) *Attorney, Agent, or Firm* — Maschoff Brennan; Brent A. Johnson; Yuefen Zhou

(57) ABSTRACT

Disclosed herein are compositions comprising an NSAID such as meloxicam and/or rizatriptan in combination with a cyclodextrin and/or a carbonate or a bicarbonate. These compositions may be orally administered, for example, to improve the bioavailability or pharmacokinetics of the NSAID for the treatment of pain such as migraine, arthritis, and other conditions. Also disclosed herein are methods of treating pain, such as migraine, comprising administering meloxicam and rizatriptan to a human being suffering from pain, such as migraine. For migraine, these methods may be particularly useful when the meloxicam and rizatriptan are administered while the human being is suffering from an acute attack of migraine pain or migraine aura. In some embodiments, the combination of meloxicam and rizatriptan may be administered in a manner that results in a $T_{max}$ of meloxicam of 3 hours or less.

28 Claims, 20 Drawing Sheets

(56) References Cited

U.S. PATENT DOCUMENTS

| | | | |
|---|---|---|---|
| 6,077,539 A | 6/2000 | Plachetka et al. | |
| 6,284,269 B1 * | 9/2001 | Struengmann | A61K 47/6951 |
| | | | 424/461 |
| 6,384,034 B2 | 5/2002 | Simitchieva et al. | |
| 6,479,551 B1 | 11/2002 | Plachetka et al. | |
| 6,495,535 B1 | 12/2002 | Plachetka et al. | |
| 6,586,458 B1 | 7/2003 | Plachetka | |
| 6,926,907 B2 | 8/2005 | Plachetka | |
| 7,030,162 B2 | 4/2006 | Plachetka et al. | |
| 7,060,694 B2 | 6/2006 | Plachetka et al. | |
| 7,332,183 B2 | 2/2008 | Plachetka et al. | |
| 8,022,095 B2 | 9/2011 | Plachetka | |
| 8,206,741 B2 | 6/2012 | Plachetka | |
| 8,512,727 B2 * | 8/2013 | Cooper | A61P 13/12 |
| | | | 424/422 |
| 8,557,285 B2 | 10/2013 | Plachetka | |
| 8,835,407 B2 | 9/2014 | Mosher et al. | |
| 8,852,636 B2 | 10/2014 | Plachetka | |
| 8,858,996 B2 | 10/2014 | Plachetka | |
| 8,865,190 B2 | 10/2014 | Plachetka | |
| 8,945,621 B2 | 2/2015 | Ault et al. | |
| 9,161,920 B2 | 10/2015 | Plachetka | |
| 9,198,888 B2 | 12/2015 | Plachetka | |
| 9,220,698 B2 | 12/2015 | Ault et al. | |
| 9,265,732 B2 | 2/2016 | Plachetka et al. | |
| 9,345,695 B2 | 5/2016 | Plachetka | |
| 9,364,439 B2 | 6/2016 | Plachetka | |
| 9,393,208 B2 | 7/2016 | Ault et al. | |
| 9,539,214 B2 | 1/2017 | Plachetka | |
| 9,707,181 B2 | 7/2017 | Plachetka | |
| 9,801,824 B2 | 10/2017 | Ault et al. | |
| 9,801,827 B2 | 10/2017 | Plachetka et al. | |
| 9,821,075 B2 | 11/2017 | Tabuteau | |
| 10,029,010 B1 | 7/2018 | Tabuteau | |
| 10,058,614 B2 | 8/2018 | Tabuteau | |
| 10,137,131 B2 | 11/2018 | Tabuteau | |
| 10,195,278 B2 | 2/2019 | Tabuteau | |
| 10,195,279 B2 | 2/2019 | Tabuteau | |
| 10,265,324 B2 | 4/2019 | Tabuteau | |
| 10,265,399 B2 | 4/2019 | Tabuteau | |
| 10,265,400 B2 | 4/2019 | Tabuteau | |
| 10,307,484 B2 | 6/2019 | Tabuteau | |
| 10,322,181 B2 | 6/2019 | Tabuteau | |
| 10,363,312 B2 | 7/2019 | Tabuteau | |
| 10,369,224 B2 | 8/2019 | Tabuteau | |
| 10,369,225 B2 | 8/2019 | Tabuteau | |
| 10,426,839 B2 | 10/2019 | Tabuteau | |
| 10,456,471 B2 | 10/2019 | Tabuteau | |
| 10,463,736 B2 | 11/2019 | Tabuteau | |
| 10,471,014 B2 | 11/2019 | Tabuteau | |
| 10,471,068 B2 | 11/2019 | Tabuteau | |
| 10,471,069 B2 | 11/2019 | Tabuteau | |
| 10,485,871 B2 | 11/2019 | Tabuteau | |
| 10,512,692 B2 | 12/2019 | Tabuteau | |
| 10,512,693 B2 | 12/2019 | Tabuteau | |
| 10,517,950 B1 | 12/2019 | Tabuteau | |
| 10,532,101 B1 | 1/2020 | Tabuteau | |
| 10,537,642 B1 | 1/2020 | Tabuteau | |
| 10,561,664 B1 | 2/2020 | Tabuteau | |
| 10,583,088 B2 | 3/2020 | Tabuteau | |
| 10,583,144 B2 | 3/2020 | Tabuteau | |
| 10,653,777 B2 | 5/2020 | Tabuteau | |
| 10,688,102 B2 | 6/2020 | Tabuteau | |
| 10,688,185 B2 | 6/2020 | Tabuteau | |
| 10,695,429 B2 | 6/2020 | Tabuteau | |
| 10,695,430 B2 | 6/2020 | Tabuteau | |
| 10,702,535 B2 | 7/2020 | Tabuteau | |
| 10,702,602 B2 | 7/2020 | Tabuteau | |
| 10,722,583 B2 | 7/2020 | Tabuteau | |
| 10,729,696 B2 | 8/2020 | Tabuteau | |
| 10,729,697 B2 | 8/2020 | Tabuteau | |
| 10,729,773 B2 | 8/2020 | Tabuteau | |
| 10,729,774 B1 | 8/2020 | Tabuteau | |
| 10,758,617 B2 | 9/2020 | Tabuteau | |
| 10,758,618 B2 | 9/2020 | Tabuteau | |
| 10,780,165 B2 | 9/2020 | Tabuteau | |
| 10,780,166 B2 | 9/2020 | Tabuteau | |
| 10,799,588 B2 | 10/2020 | Tabuteau | |
| 10,821,181 B2 | 11/2020 | Tabuteau | |
| 10,821,182 B2 | 11/2020 | Tabuteau | |
| 10,894,053 B2 | 1/2021 | Tabuteau | |
| 10,905,693 B2 | 2/2021 | Tabuteau | |
| 10,918,722 B2 | 2/2021 | Tabuteau | |
| 10,933,136 B2 | 3/2021 | Tabuteau | |
| 10,933,137 B2 | 3/2021 | Tabuteau | |
| 10,987,358 B2 | 4/2021 | Tabuteau | |
| 11,013,805 B2 | 5/2021 | Tabuteau | |
| 11,013,806 B2 | 5/2021 | Tabuteau | |
| 11,020,483 B2 | 6/2021 | Tabuteau | |
| 2002/0016348 A1 | 2/2002 | Simitchieva et al. | |
| 2004/0229038 A1 | 11/2004 | Cooper et al. | |
| 2005/0249806 A1 | 11/2005 | Proehl et al. | |
| 2007/0154542 A1 | 7/2007 | Tananbaum et al. | |
| 2007/0281927 A1 | 12/2007 | Tyavanagimatt et al. | |
| 2009/0068262 A1 | 3/2009 | Zalit et al. | |
| 2009/0203680 A1 | 8/2009 | Hanna | |
| 2009/0311335 A1 * | 12/2009 | Jenkins | A61K 31/616 |
| | | | 424/491 |
| 2010/0226943 A1 | 9/2010 | Brennan et al. | |
| 2013/0266658 A1 | 10/2013 | Weiß et al. | |
| 2014/0248353 A1 | 9/2014 | Ryoo et al. | |
| 2016/0228576 A1 | 8/2016 | Tabuteau | |
| 2018/0050106 A1 | 2/2018 | Tabuteau | |
| 2018/0127490 A1 | 5/2018 | Bigal et al. | |
| 2018/0207274 A1 | 7/2018 | Tabuteau | |
| 2018/0214380 A1 | 8/2018 | Tabuteau | |
| 2018/0256593 A1 | 9/2018 | Tabuteau | |
| 2018/0264114 A1 | 9/2018 | Tabuteau | |
| 2018/0264115 A1 | 9/2018 | Tabuteau | |
| 2018/0271981 A1 | 9/2018 | Tabuteau | |
| 2018/0280306 A1 | 10/2018 | Tabuteau | |
| 2018/0280308 A1 | 10/2018 | Tabuteau | |
| 2018/0280512 A1 | 10/2018 | Tabuteau | |
| 2018/0289806 A1 | 10/2018 | Tabuteau | |
| 2018/0289807 A1 | 10/2018 | Tabuteau | |
| 2018/0289808 A1 | 10/2018 | Tabuteau | |
| 2019/0000975 A1 | 1/2019 | Tabuteau | |
| 2019/0070192 A1 | 3/2019 | Tabuteau | |
| 2019/0142942 A1 | 5/2019 | Tabuteau | |
| 2019/0142943 A1 | 5/2019 | Tabuteau | |
| 2019/0224320 A1 | 7/2019 | Tabuteau | |
| 2019/0224321 A1 | 7/2019 | Tabuteau | |
| 2019/0231792 A1 | 8/2019 | Tabuteau | |
| 2019/0255177 A1 | 8/2019 | Tabuteau | |
| 2019/0307884 A1 | 10/2019 | Tabuteau | |
| 2019/0314504 A1 | 10/2019 | Tabuteau | |
| 2019/0336510 A1 | 11/2019 | Tabuteau | |
| 2020/0000819 A1 | 1/2020 | Tabuteau | |
| 2020/0000820 A1 | 1/2020 | Tabuteau | |
| 2020/0000919 A1 | 1/2020 | Tabuteau | |
| 2020/0000920 A1 | 1/2020 | Tabuteau | |
| 2020/0000921 A1 | 1/2020 | Tabuteau | |
| 2020/0000922 A1 | 1/2020 | Tabuteau | |
| 2020/0009250 A1 | 1/2020 | Tabuteau | |
| 2020/0030338 A1 | 1/2020 | Tabuteau | |
| 2020/0038408 A1 | 2/2020 | Tabuteau | |
| 2020/0085951 A1 | 3/2020 | Tabuteau | |
| 2020/0085952 A1 | 3/2020 | Tabuteau | |
| 2020/0085953 A1 | 3/2020 | Tabuteau | |
| 2020/0085954 A1 | 3/2020 | Tabuteau | |
| 2020/0085955 A1 | 3/2020 | Tabuteau | |
| 2020/0155565 A1 | 5/2020 | Tabuteau | |
| 2020/0179396 A1 | 6/2020 | Tabuteau | |
| 2020/0222539 A1 | 7/2020 | Tabuteau | |
| 2020/0230239 A1 | 7/2020 | Tabuteau | |
| 2020/0230240 A1 | 7/2020 | Tabuteau | |
| 2020/0230241 A1 | 7/2020 | Tabuteau | |
| 2020/0246461 A1 | 8/2020 | Tabuteau | |
| 2020/0246462 A1 | 8/2020 | Tabuteau | |
| 2020/0254097 A1 | 8/2020 | Tabuteau | |
| 2020/0261466 A1 | 8/2020 | Tabuteau | |
| 2020/0261467 A1 | 8/2020 | Tabuteau | |
| 2020/0276311 A1 | 9/2020 | Tabuteau | |
| 2020/0289524 A1 | 9/2020 | Tabuteau | |

(56) References Cited

U.S. PATENT DOCUMENTS

| | | |
|---|---|---|
| 2020/0330476 A1 | 10/2020 | Tabuteau |
| 2020/0338198 A1 | 10/2020 | Tabuteau |
| 2020/0376124 A1 | 12/2020 | Tabuteau |
| 2020/0376125 A1 | 12/2020 | Tabuteau |
| 2020/0405861 A1 | 12/2020 | Tabuteau |
| 2020/0405862 A1 | 12/2020 | Tabuteau |
| 2021/0000956 A1 | 1/2021 | Tabuteau |
| 2021/0008211 A1 | 1/2021 | Tabuteau |
| 2021/0030876 A1 | 2/2021 | Tabuteau |
| 2021/0121474 A1 | 4/2021 | Tabuteau |
| 2021/0128575 A1 | 5/2021 | Tabuteau |
| 2021/0128576 A1 | 5/2021 | Tabuteau |
| 2021/0154299 A1 | 5/2021 | Tabuteau |

FOREIGN PATENT DOCUMENTS

| | | |
|---|---|---|
| CN | 101987081 | 3/2011 |
| CN | 102526058 A | 7/2012 |
| WO | 1998006392 A1 | 2/1998 |
| WO | 1999009988 A1 | 3/1999 |
| WO | 2000035448 | 6/2000 |
| WO | 2000059475 | 10/2000 |
| WO | 2005021041 A1 | 3/2005 |
| WO | 2005076987 | 8/2005 |
| WO | 2005105102 A1 | 11/2005 |
| WO | 2008006216 | 1/2008 |
| WO | 2012072570 | 6/2012 |
| WO | 2014161131 A1 | 10/2014 |
| WO | 2016131067 | 8/2016 |
| WO | 2017042607 | 3/2017 |
| WO | 2018129220 A1 | 7/2018 |

OTHER PUBLICATIONS

Johnell et al., Concomitant Use of Gastroprotective Drugs Among Elderly NSAID/COX-2 Selective Inhibitor Users: A Nationwide Register-Based Study, Clinical Drug Investigation, 28(11), 687-695, Nov. 2008.
Leonard et al., Proton Pump Inhibitors and Traditional Nonsteroidal Anti-Inflammatory Drugs and the Risk of Acute Interstitial Nephritis and Acute Kidney Injury, Pharmacoepidemiology and Drug Safety, 21(11), 1155-1172, Nov. 2012.
Vonkeman et al., Proton-Pump Inhibitors are Associated with a Reduced Risk for Bleeding and Perforated Gastroduodenal Ulcers Attributable to Non-Steroidal Anti-Inflammatory Drugs: A Nested Case-Control Study, Arthritis Research & Therapy, 9(3), May 2007, 8 pgs.
Yilmaz et al., Does Adding Misoprostol to Standard Intravenous Proton Pump Inhibitor Protocol Improve the Outcome of Aspirin/NSAID-Induced Upper Gastrointestinal Bleeding?, Digestive Diseases and Sciences, 52(1), 110-118, Jan. 2007.
International search report dated Aug. 11, 2016, corresponding to international patent application No. PCT/US2016/026991.
Witten opinion of the international searching authority dated Aug. 11, 2016, corresponding to international patent application No. PCT/US2016/026991.
Stella et al., Toxicologic Pathology, 2008, 36:30-42.
Jain et al., AAAPS PharmSciTech, 2011, 12(4):1163-1175.
Baboota et al., Journal of Inclusion Phenomena and Macrocyclic Chemistry, 2005, 51:219-224.
U.S. Appl. No. 15/132,130, filed Apr. 18, 2016 First Named Inventor: Herriot Tabuteau Assignee: Axsome Therapeutics, Inc.
U.S. Appl. No. 15/797,955, filed Oct. 30, 2017 First Named Inventor: Herriot Tabuteau Assignee: Axsome Therapeutics, Inc.
U.S. Appl. No. 15/902,770, filed Feb. 22, 2018 First Named Inventor: Herriot Tabuteau Assignee: Axsome Therapeutics, Inc.
U.S. Appl. No. 15/936,176, filed Mar. 26, 2018 First Named Inventor: Herriot Tabuteau Assignee: Axsome Therapeutics, Inc.
U.S. Appl. No. 15/976,800, filed May 10, 2018 First Named Inventor: Herriot Tabuteau Assignee: Axsome Therapeutics, Inc.
U.S. Appl. No. 15/984,055, filed May 18, 2018 First Named Inventor: Herriot Tabuteau Assignee: Axsome Therapeutics, Inc.
U.S. Appl. No. 15/986,215, filed May 22, 2018 First Named Inventor: Herriot Tabuteau Assignee: Axsome Therapeutics, Inc.
U.S. Appl. No. 15/988,104, filed May 24, 2018 First Named Inventor: Herriot Tabuteau Assignee: Axsome Therapeutics, Inc.
U.S. Appl. No. 15/989,734, filed May 25, 2018 First Named Inventor: Herriot Tabuteau Assignee: Axsome Therapeutics, Inc.
U.S. Appl. No. 16/000,701, filed Jun. 5, 2018 First Named Inventor: Herriot Tabuteau Assignee: Axsome Therapeutics, Inc.
U.S. Appl. No. 16/001,697, filed Jun. 6, 2018 First Named Inventor: Herriot Tabuteau Assignee: Axsome Therapeutics, Inc.
U.S. Appl. No. 16/002,865, filed Jun. 7, 2018 First Named Inventor: Herriot Tabuteau Assignee: Axsome Therapeutics, Inc.
U.S. Appl. No. 16/006,548, filed Jun. 12, 2018 First Named Inventor: Herriot Tabuteau Assignee: Axsome Therapeutics, Inc.
U.S. Appl. No. 16/006,642, filed Jun. 12, 2018 First Named Inventor: Herriot Tabuteau Assignee: Axsome Therapeutics, Inc.
U.S. Appl. No. 16/006,692, filed Jun. 12, 2018 First Named Inventor: Herriot Tabuteau Assignee: Axsome Therapeutics, Inc.
Hosie et al., British Journal of Rheumatology, 35 (suppl.1), 39-43,1996.
Wojtulewski et al., British Journal of Rheumatology; 35 (suppl.1), 22-28,1996.
Goldstein et al., Intragastric Acid Control in Non-Steroidal Anti-inflammatory Drug Users: Comparison of Esomeprazole, Lansoprazole and Pantoprazole, Alimentary Pharmacology & Therapeutics 23, 1189-1196, 2006.
Euller-Ziegler et al. Meloxicam: a review of its pharmacokinetics, efficacy and tolerability following intramuscular administration, Inflamm. res. 50, Supplement 1, S5-S9, 2001.
U.S. Appl. No. 16/181,086, filed Nov. 5, 2018 First Named Inventor: Herriot Tabuteau Assignee: Axsome Therapeutics, Inc.
U.S. Appl. No. 16/247,406, filed Jan. 14, 2019 First Named Inventor: Herriot Tabuteau Assignee: Axsome Therapeutics, Inc.
U.S. Appl. No. 16/248,449, filed Jan. 15, 2019 First Named Inventor: Herriot Tabuteau Assignee: Axsome Therapeutics, Inc.
Iroko Pharmaceuticals, Vivlodex Label, Oct. 2015.
Mayo Clinic, http://web. archive.org/web/20141113013539/https://www.mayoclinic.org/drugs-supplements /meloxicam-oral-route/proper-use/drg-20066928 (bearing an alleged date of 2014) (retrieved from the internet Mar. 3, 2019) (2014).
U.S. Appl. No. 16/372,958, filed Apr. 2, 2019 First Named Inventor: Herriot Tabuteau Assignee: Axsome Therapeutics, Inc.
U.S. Appl. No. 16/372,977, filed Apr. 2, 2019 First Named Inventor: Herriot Tabuteau Assignee: Axsome Therapeutics, Inc.
U.S. Appl. No. 16/374,081, filed Apr. 3, 2019 First Named Inventor: Herriot Tabuteau Assignee: Axsome Therapeutics, Inc.
U.S. Appl. No. 16/403,034, filed May 3, 2019 First Named Inventor: Herriot Tabuteau Assignee: Axsome Therapeutics, Inc.
U.S. Appl. No. 16/440,695, filed Jun. 13, 2019 First Named Inventor: Herriot Tabuteau Assignee: Axsome Therapeutics, Inc.
U.S. Appl. No. 16/454,319, filed Jun. 27, 2019 First Named Inventor: Herriot Tabuteau Assignee: Axsome Therapeutics, Inc.
U.S. Appl. No. 16/513,612, filed Jul. 16, 2019 First Named Inventor: Herriot Tabuteau Assignee: Axsome Therapeutics, Inc.
Láinez, "Rizatriptan in the treatment of migraine." Neuropsychiatric disease and treatment, 2(3), p. 247, Sep. 2006.
U.S. Appl. No. 16/565,111, filed Sep. 9, 2019 First Named Inventor: Herriot Tabuteau Assignee: Axsome Therapeutics, Inc.
U.S. Appl. No. 16/566,476, filed Sep. 10, 2019 First Named Inventor: Herriot Tabuteau Assignee: Axsome Therapeutics, Inc.
U.S. Appl. No. 16/567,859, filed Sep. 11, 2019 First Named Inventor: Herriot Tabuteau Assignee: Axsome Therapeutics, Inc.
U.S. Appl. No. 16/568,703, filed Sep. 12, 2019 First Named Inventor: Herriot Tabuteau Assignee: Axsome Therapeutics, Inc.
U.S. Appl. No. 16/570,434, filed Sep. 13, 2019 First Named Inventor: Herriot Tabuteau Assignee: Axsome Therapeutics, Inc.
U.S. Appl. No. 16/570,451, filed Sep. 13, 2019 First Named Inventor: Herriot Tabuteau Assignee: Axsome Therapeutics, Inc.
U.S. Appl. No. 16/572,042, filed Sep. 16, 2019 First Named Inventor: Herriot Tabuteau Assignee: Axsome Therapeutics, Inc.
U.S. Appl. No. 16/589,692, filed Oct. 1, 2019 First Named Inventor: Herriot Tabuteau Assignee: Axsome Therapeutics, Inc.

(56) References Cited

OTHER PUBLICATIONS

U.S. Appl. No. 16/653,877, filed Oct. 15, 2019 First Named Inventor: Herriot Tabuteau Assignee: Axsome Therapeutics, Inc.
Landy S, Rice K, Lobo B. Central sensitisation and cutaneous allodynia in migraine. CNS drugs, 18(6), 337-42, May 2004.
U.S. Appl. No. 16/688,491, filed Nov. 19, 2019 First Named Inventor: Herriot Tabuteau Assignee: Axsome Therapeutics, Inc.
U.S. Appl. No. 16/689,970, filed Nov. 20, 2019 First Named Inventor: Herriot Tabuteau Assignee: Axsome Therapeutics, Inc.
U.S. Appl. No. 16/690,464, filed Nov. 21, 2019 First Named Inventor: Herriot Tabuteau Assignee: Axsome Therapeutics, Inc.
U.S. Appl. No. 16/693,052, filed Nov. 21, 2019 First Named Inventor: Herriot Tabuteau Assignee: Axsome Therapeutics, Inc.
U.S. Appl. No. 16/694,440, filed Nov. 25, 2019 First Named Inventor: Herriot Tabuteau Assignee: Axsome Therapeutics, Inc.
Weatherall, "Drug therapy in headache," Clin. Med. (Lond.), 15(3), 273-279, Jun. 2015. (PMID: 26031979, Year 2015).
U.S. Appl. No. 16/773,567, filed Jan. 27, 2020 First Named Inventor: Herriot Tabuteau Assignee: Axsome Therapeutics, Inc.
U.S. Appl. No. 16/790,085, filed Feb. 13, 2020 First Named Inventor: Herriot Tabuteau Assignee: Axsome Therapeutics, Inc.
Cameron C, et al., Triptans in the Acute Treatment of Migraine: A Systematic Review and Network Meta-Analysis, DOI: 10.1111/head.12601, https://www.ncbi.nlm.nih.gov/pubmed/26178694, accessed on Mar. 25, 2020.
Ng-Mak DS, et al., Acute migraine treatment with oral triptans and NSAIDs in a managed care population, DOI: 10.1111/j.1526-4610.2007.01055.x, https://www.ncbi.nlm.nih.gov/pubmed/18819177, accessed on Mar. 25, 2020.
Lipton RB, et al., Impact of NSAID and Triptan use on developing chronic migraine: results from the American Migraine Prevalence and Prevention (AMPP) study, DOI: 10.1111/head.12201, https://www.ncbi.nlm.nih.gov/pubmed/23992516, accessed on Mar. 25, 2020.
U.S. Appl. No. 16/834,077, filed Mar. 30, 2020 First Named Inventor: Herriot Tabuteau Assignee: Axsome Therapeutics, Inc.
U.S. Appl. No. 16/835,848, filed Mar. 31, 2020 First Named Inventor: Herriot Tabuteau Assignee: Axsome Therapeutics, Inc.
U.S. Appl No. 16/837,769, filed Apr. 1, 2020 First Named Inventor: Herriot Tabuteau Assignee: Axsome Therapeutics, Inc.
U.S. Appl. No. 16/841,436, filed Apr. 6, 2020 First Named Inventor: Herriot Tabuteau Assignee: Axsome Therapeutics, Inc.
U.S. Appl. No. 16/842,063, filed Apr. 7, 2020 First Named Inventor: Herriot Tabuteau Assignee: Axsome Therapeutics, Inc.
U.S. Appl. No. 16/843,490, filed Apr. 8, 2020 First Named Inventor: Herriot Tabuteau Assignee: Axsome Therapeutics, Inc.
U.S. Appl. No. 16/844,634, filed Apr. 9, 2020 First Named Inventor: Herriot Tabuteau Assignee: Axsome Therapeutics, Inc.
Robert T., Migraine Management Essential 6: Rescue treatment; bearing an alleged date of Apr. 2011, https://migraine.com/blog/migraine-management-rescue-treatment/, accessed on Apr. 15, 2020.
American Headache Society, Home/News /MAST Study Identifies Most Bothersome Symptom (MBS) for Patients with Migraine, https://americanheadachesociety.org/news/mast-most-bothersome-symptom/, accessed on May 7, 2020.
Munjal et al., Most Bothersome Symptom in Persons With Migraine: Results From the Migraine in America Symptoms and Treatment (MAST) Study, The Journal of Head and Face Pain, https://headachejournal.onlinelibrary.wiley.com/doi/10.1111/head.13708, accessed on May 7, 2020.

U.S. Appl. No. 16/854,320, filed Apr. 21, 2020 First Named Inventor: Herriot Tabuteau Assignee: Axsome Therapeutics, Inc.
U.S. Appl. No. 16/857,435, filed Apr. 24, 2020 First Named Inventor: Herriot Tabuteau Assignee: Axsome Therapeutics, Inc.
U.S. Appl. No. 16/867,929, filed May 6, 2020 First Named Inventor: Herriot Tabuteau Assignee: Axsome Therapeutics, Inc.
International Search Report and Written Opinion, PCT/US2019/040495, dated Oct. 31, 2019.
Deshpande et al., Bi-layer tablets—An emerging trend: a review, International journal of pharmaceutical sciences and research, 2(10): 2534-2544, Oct. 1, 2011.
U.S. Appl. No. 16/885,975, filed May 28, 2020 First Named Inventor: Herriot Tabuteau Assignee: Axsome Therapeutics, Inc.
International Search Report, PCT/US2020/017046, dated Jun. 4, 2020.
Written Opinion of the International Searching Authority, PCT/US2020/017046, dated Jun. 4, 2020.
U.S. Appl. No. 16/921,006, filed Jul. 6, 2020, First Named Inventor: Herriot Tabuteau Assignee: Axsome Therapeutics, Inc.
U.S. Appl. No. 16/927,623, filed Jul. 13, 2020 First Named Inventor: Herriot Tabuteau Assignee: Axsome Therapeutics, Inc.
U.S. Appl. No. 16/997,740, filed Aug. 19, 2020 First Named Inventor: Herriot Tabuteau Assignee: Axsome Therapeutics, Inc.
U.S. Appl. No. 16/998,622, filed Aug. 20, 2020 First Named Inventor: Herriot Tabuteau Assignee: Axsome Therapeutics, Inc.
U.S. Appl. No. 17/016,172, filed Sep. 9, 2020 First Named Inventor: Herriot Tabuteau Assignee: Axsome Therapeutics, Inc..
U.S. Appl. No. 17/018,275, filed Sep. 11, 2020 First Named Inventor: Herriot Tabuteau Assignee: Axsome Therapeutics, Inc.
U.S. Appl. No. 17/021,131, filed Sep. 15, 2020 First Named Inventor: Herriot Tabuteau Assignee: Axsome Therapeutics, Inc.
U.S. Appl. No. 17/024,233, filed Sep. 17, 2020 First Named Inventor: Herriot Tabuteau Assignee: Axsome Therapeutics, Inc.
U.S. Appl. No. 17/067,006, filed Oct. 9, 2020 First Named Inventor: Herriot Tabuteau Assignee: Axsome Therapeutics, Inc.
U.S. Appl. No. 17/122,618, filed Dec. 15, 2020 First Named Inventor: Harriot Tabuteau Assignee: Axsome Therapeutics, Inc.
U.S. Appl. No. 17/145,744, filed Jan. 11, 2021 First Named Inventor: Herriot Tabuteau Assignee: Axsome Therapeutics, Inc.
U.S. Appl. No. 17/148,342, filed Jan. 13, 2021 First Named Inventor: Herriot Tabuteau Assignee: Axsome Therapertics, Inc.
International Preliminary Report on Patentability, PCT/US2019/040495, dated Jan. 14, 2021.
U.S. Appl. No. 17/165,274, filed Feb. 2, 2021 First Named Inventor: Herriot Tabuteau Assignee: Axsome Therapeutics, Inc.
U.S. Appl. No. 17/168,016, filed Feb. 4, 2021 First Named Inventor: Herriot Tabuteau Assignee: Axsome Therapeutics, Inc.
U.S. Appl. No. 17/170,453, filed Feb. 8, 2021 First Named Inventor: Herriot Tabuteau Assignee: Axsome Therapeutics, Inc.
U.S. Appl. No. 17/183,700, filed Feb. 24, 2021 First Named Inventor: Herriot Tabuteau Assignee: Axsome Therapeutics, Inc.
U.S. Appl. No. 17/318,691, filed May 12, 2021 First Named Inventor: Herriot Tabuteau Assignee: Axsome Therapeutics, Inc.
U.S. Appl. No. 17/319,898, filed May 13, 2021 First Named Inventor: Herriot Tabuteau Assignee: Axsome Therapeutics, Inc.
U.S. Appl. No. 17/325,616, filed May 20, 2021 First Named Inventor: Herriot Tabuteau Assignee: Axsome Therapeutics, Inc.
International Search Report and Written Opinion of the International Searching Authority, PCT/US2021/026027, dated Jun. 4, 2021.

* cited by examiner

PHARMACEUTICAL COMPOSITIONS COMPRISING MELOXICAM

CROSS-REFERENCE TO RELATED APPLICATIONS

This application is a continuation-in-part of U.S. patent application Ser. No. 16/842,063, filed Apr. 7, 2020, which is a continuation-in-part of U.S. patent application Ser. No. 16/694,440, filed Nov. 25, 2019, now U.S. Pat. No. 10,702,602; which is a continuation-in-part of U.S. patent application Ser. No. 16/565,111, filed Sep. 9, 2019, now U.S. Pat. No. 10,532,101; which is a continuation-in-part of U.S. patent application Ser. No. 16/372,977, filed Apr. 2, 2019, now U.S. Pat. No. 10,426,839; which is a continuation of U.S. patent application Ser. No. 15/988,104, filed May 24, 2018, now U.S. Pat. No. 10,265,400; which is a continuation of U.S. patent application Ser. No. 15/902,770, filed Feb. 22, 2018, now U.S. Pat. No. 10,029,010; which is a continuation of U.S. patent application Ser. No. 15/797,955, filed Oct. 30, 2017, now U.S. Pat. No. 10,058,614; which is a continuation-in-part of U.S. patent application Ser. No. 15/132,130, filed Apr. 18, 2016, now U.S. Pat. No. 9,821,075; which is a continuation of International Pat. App. No. PCT/US2016/026991, filed Apr. 11, 2016; which claims the benefit of U.S. Prov. Pat. App. Nos. 62/114,215, filed Feb. 10, 2015, and 62/259,993, filed Nov. 25, 2015; U.S. patent application Ser. No. 15/797,955 also claims the benefit of U.S. Prov. Pat. App. Nos. 62/526,884, filed Jun. 29, 2017, and 62/536,466, filed Jul. 25, 2017; any of the above applications, U.S. patents issued from, or U.S. publications of any of the above applications are incorporated by reference in their entirety.

BACKGROUND

Meloxicam, which has the structure:

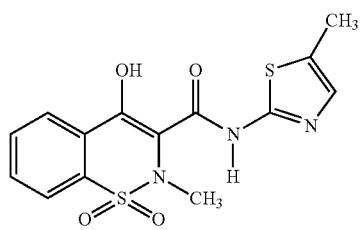 [SMILES: Cc1cnc(NC(=O)C2=C(O)c3ccccc3S(=O)(=O)N2C)s1]

is a nonsteroidal anti-inflammatory (NSAID) drug that exhibits anti-inflammatory, analgesic, and antipyretic activities. The meloxicam mechanism of action may be related to prostaglandin synthetase (cyclo-oxygenase, COX) inhibition which is involved in the initial steps of the arachidonic acid cascade, resulting in the reduced formation of prostaglandins, thromboxanes and prostacylin.

SUMMARY

Meloxicam and some other NSAIDs have poor aqueous solubility which may reduce bioavailability and slow the onset of pain relief resulting from their use. One means of increasing the solubility and bioavailability of meloxicam is through the use of cyclodextrins. Cyclodextrin (also known as cycloamyloses) are generally cyclic polysaccharides which form a bucket-like shape. Cyclodextrins help to increase bioavailability of other molecules because cyclodextrins are hydrophobic on the inside and hydrophilic on the inside which helps to facilitate the transport of molecules. The naturally occurring cyclodextrins include six, seven, and eight glucose units (α, β, and γ-cyclodextrin, respectively). However, synthetic cyclodextrins containing more or less glucose units are possible. In aqueous solutions, cyclodextrins can form complexes (i.e., an inclusion complex) with drugs by incorporating the drug into the center/hydrophobic portion of the cyclodextrin ring; although cyclodextrin compounds are also known to aggregate around a drug in a micelle-type structure. This ability of cyclodextrins may allow them to act as carriers to increase the bioavailability of less soluble drugs.

Some embodiments include a method of treating migraine comprising: selecting a human migraine patient with a history of inadequate response to prior migraine treatments, and orally administering a dosage form to the migraine patient, wherein the dosage form comprises a combination of: 1) a complex of meloxicam with a sulfobutyl ether β-cyclodextrin (SBEβCD), 2) a bicarbonate, and 3) a rizatriptan.

Some embodiments include an inclusion complex of meloxicam in a cyclodextrin.

Some embodiments include a dosage form comprising: 1) an inclusion complex of meloxicam and a cyclodextrin, or 2) meloxicam and a carbonate or a bicarbonate.

Some embodiments include a method of administering meloxicam orally, comprising orally administering a dosage form described herein to a patient in need of treatment.

Some embodiments include a method of administering meloxicam intravenously, comprising intravenously administering a dosage form described herein to a patient in need of treatment.

Disclosed herein are formulations for an inclusion complex of cyclodextrin and meloxicam with bicarbonate and methods of use thereof.

Disclosed herein are formulations and methods for delivering meloxicam with cyclodextrin to a subject by oral, enteral, intravenous, intramuscular, subcutaneous, intranasal, or other parenteral means.

Disclosed also are methods for treating pain and pain associated with conditions by delivering a dosage form with meloxicam, cyclodextrin, and bicarbonate by oral, enteral, intravenous, intramuscular, subcutaneous, intranasal, or other parenteral means to a subject.

A combination of rizatriptan and meloxicam (referred to herein for convenience as a "subject combination") may be used to treat a variety of pain conditions.

Rizatriptan has the structure as shown below.

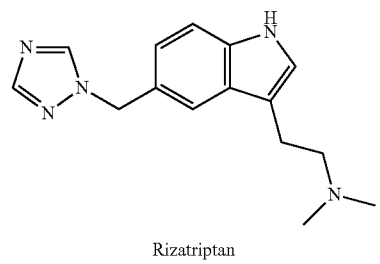 [SMILES: CN(C)CCc1c[nH]c2ccc(Cn3cncn3)cc12]

Rizatriptan

Some embodiments include a subject combination comprising: 1) an inclusion complex of meloxicam and a cyclodextrin, 2) rizatriptan, and 3) a bicarbonate for treating migraine in a human being. The migraine may be treatmentresistant migraine. The human being may have a history of inadequate response to prior treatments.

Some embodiments include a subject combination comprising rizatriptan and meloxicam that has rapid, sustained, substantial and statistically significant efficacy as compared to placebo, rizatriptan, or meloxicam in the acute treatment of migraine in patients with a history of inadequate response to prior acute treatments.

Some embodiments include a subject combination comprising rizatriptan and meloxicam that requires significantly less use of rescue medication as compared to rizatriptan, meloxicam, or placebo.

DETAILED DESCRIPTION

Figure 1:
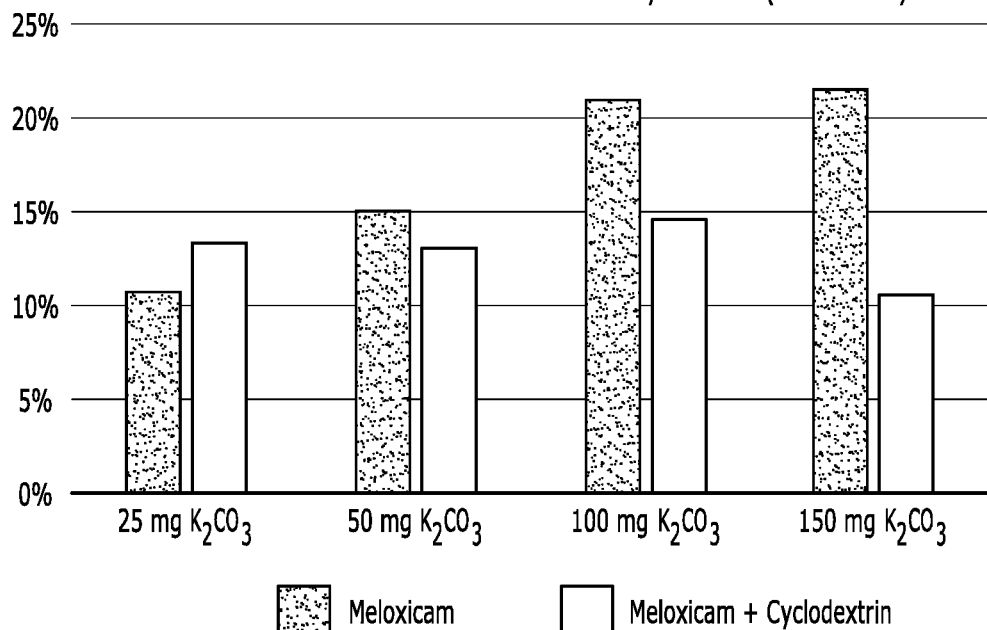
FIG. 1 is a depiction of the results described in Example 2 and contained in Table 6.
Figure 2:
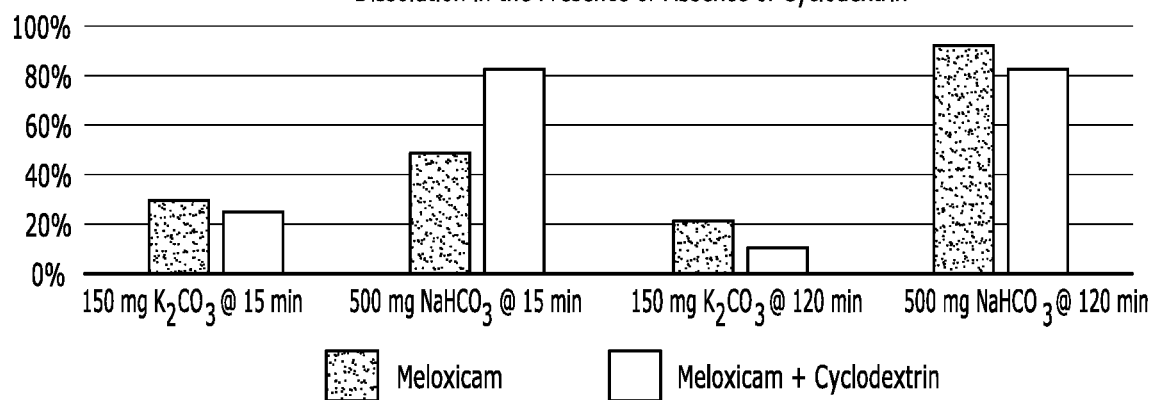
FIG. 2 is another depiction of the results described in Example 2 and contained in Table 6.
Figure 3:
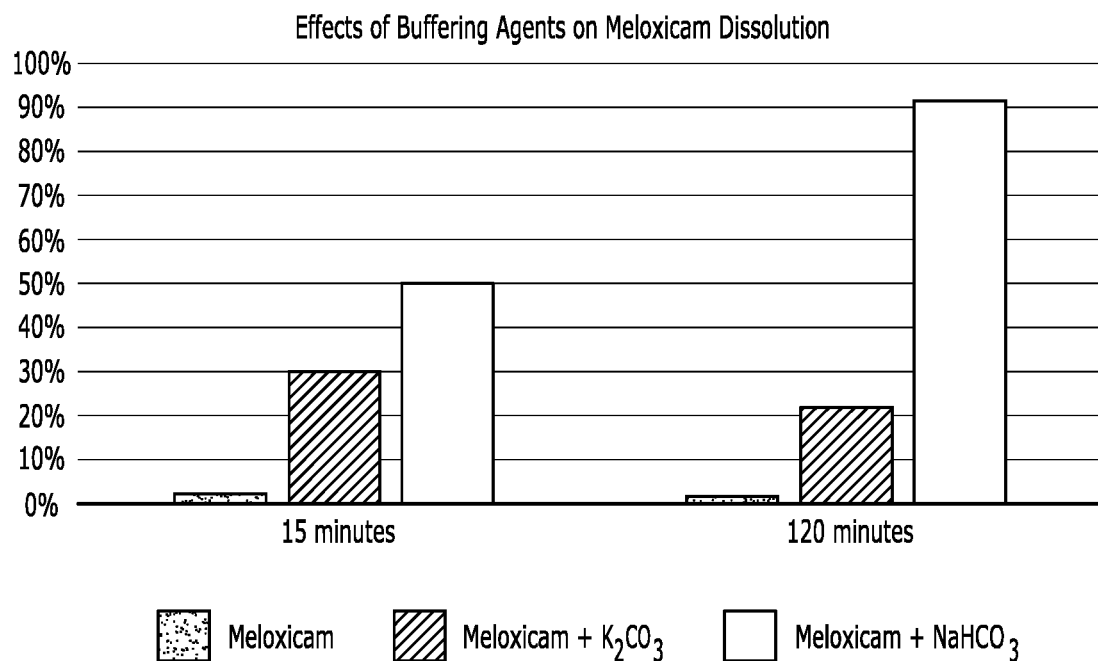
FIG. 3 is another depiction of the results described in Example 2 and contained in Table 6.
Figure 4:
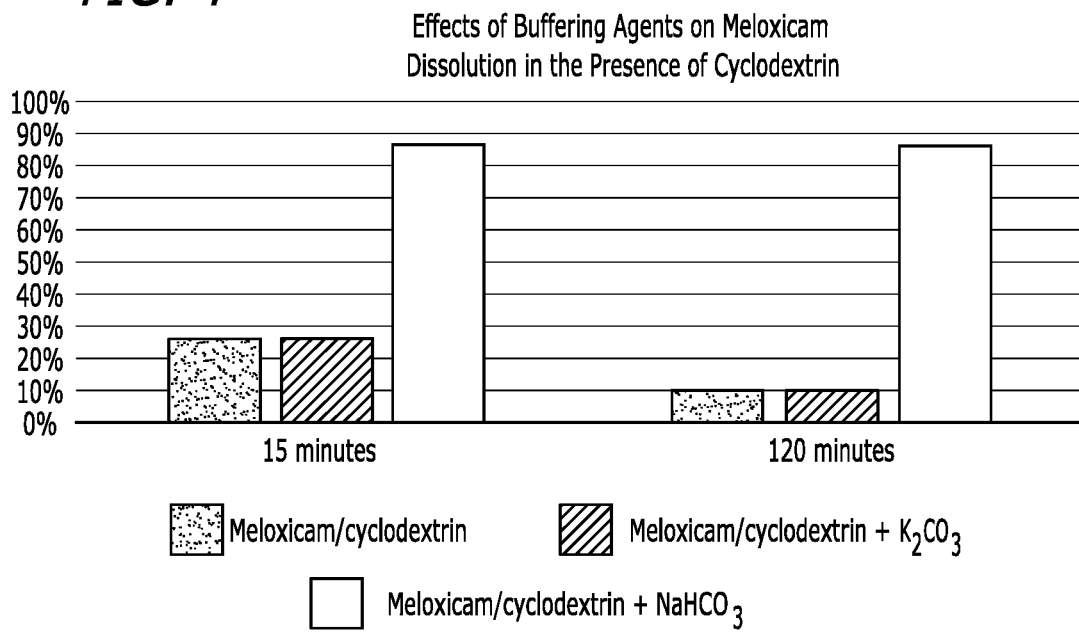
FIG. 4 is another depiction of the results described in Example 2 and contained in Table 6.
Figure 5:
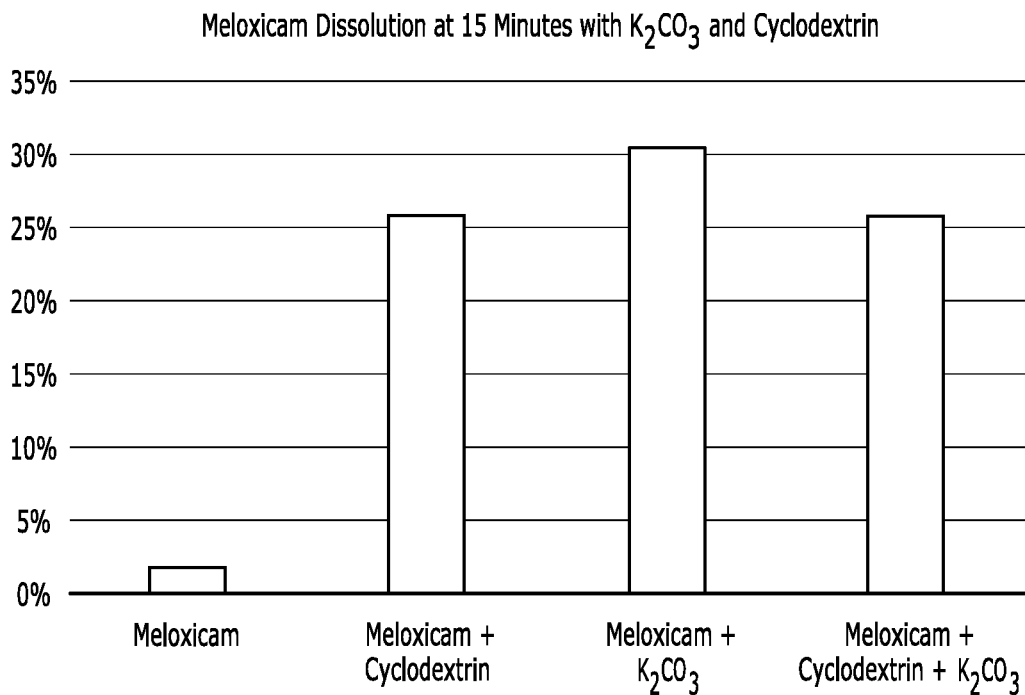
FIG. 5 is another depiction of the results described in Example 2 and contained in Table 6.
Figure 6:
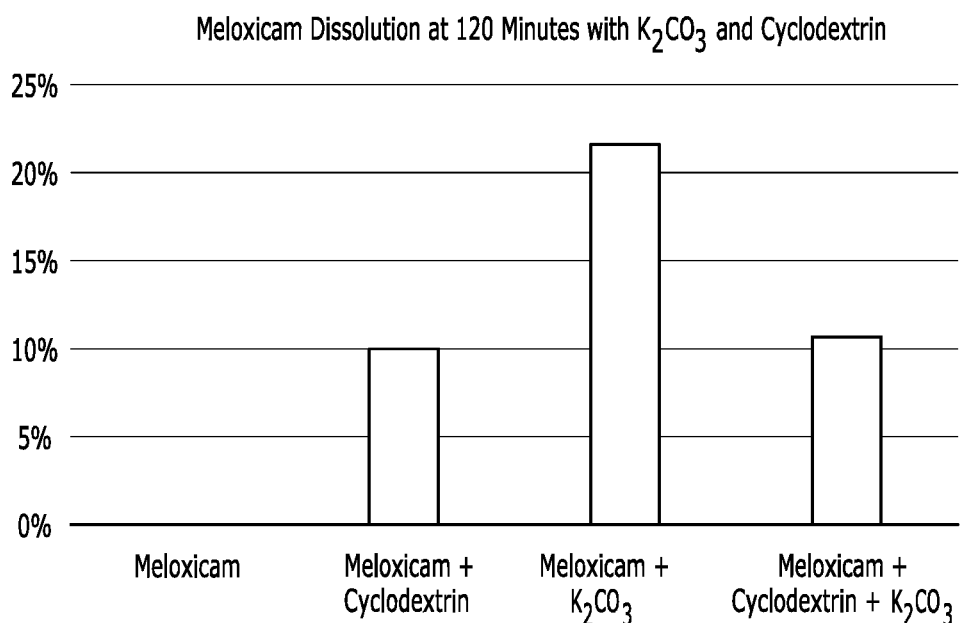
FIG. 6 is another depiction of the results described in Example 2 and contained in Table 6.
Figure 7:
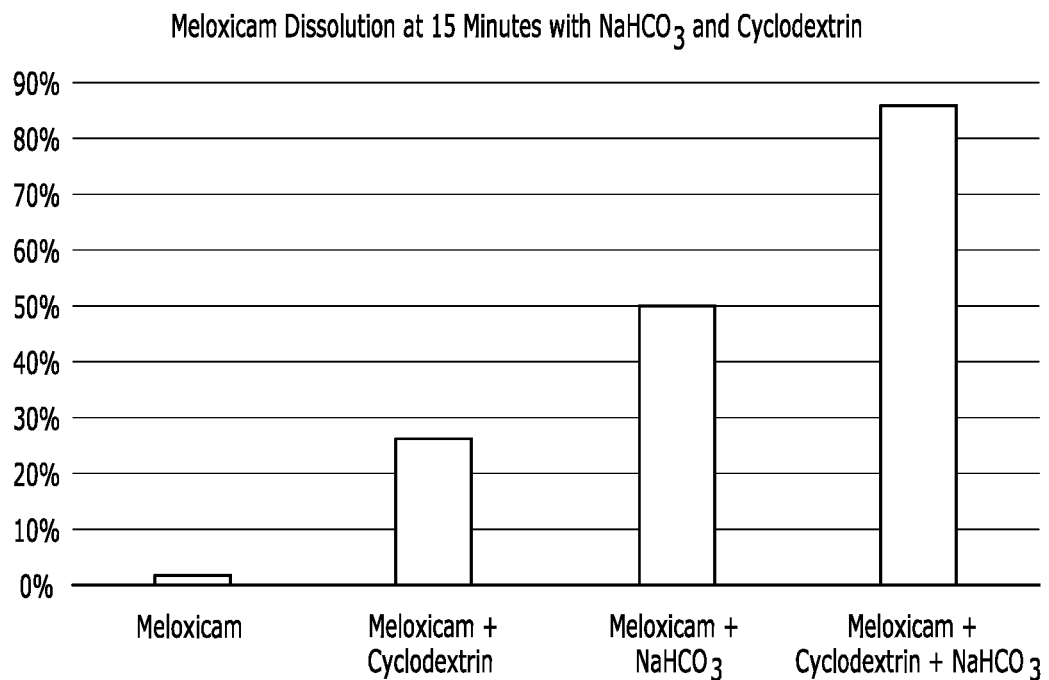
FIG. 7 is another depiction of the results described in Example 2 and contained in Table 6.
Figure 8:
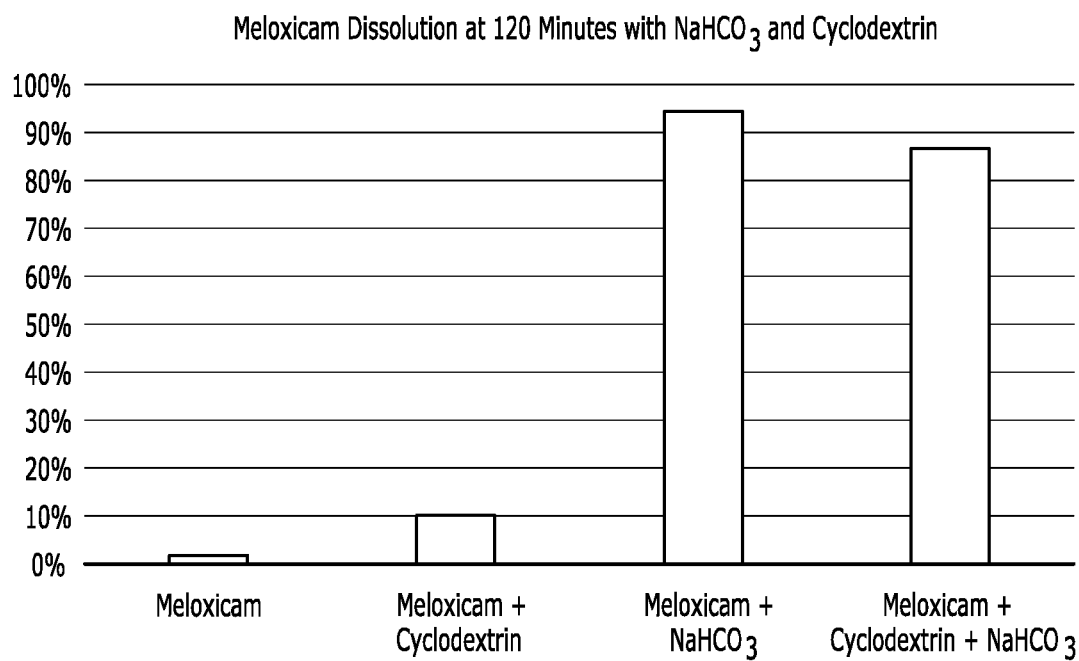
FIG. 8 is another depiction of the results described in Example 2 and contained in Table 6.
Figure 9:
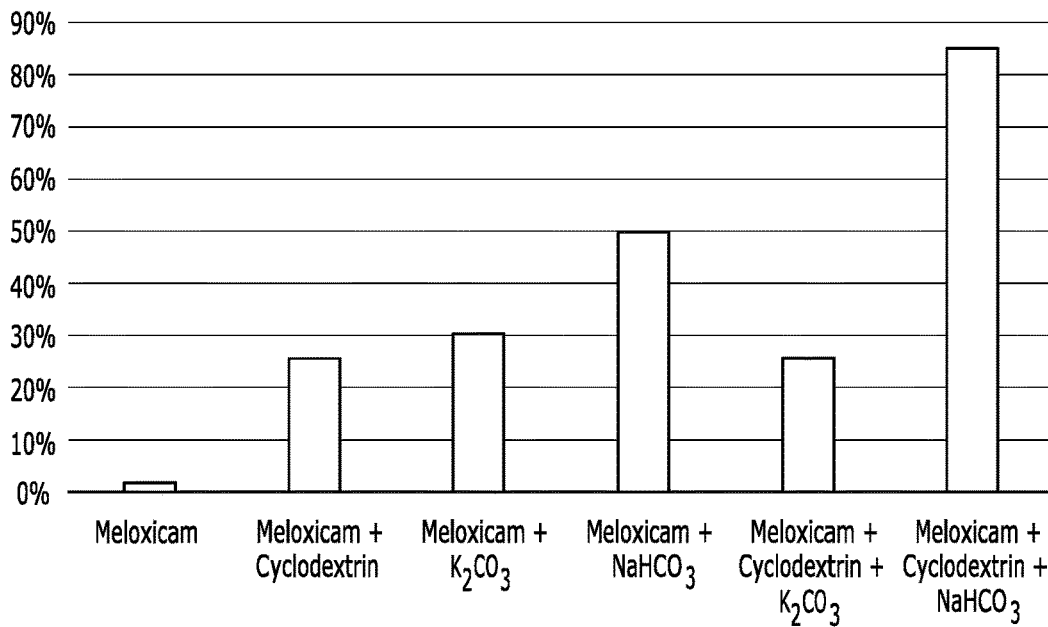
FIG. 9 is another depiction of the results described in Example 2 and contained in Table 6.
Figure 10:
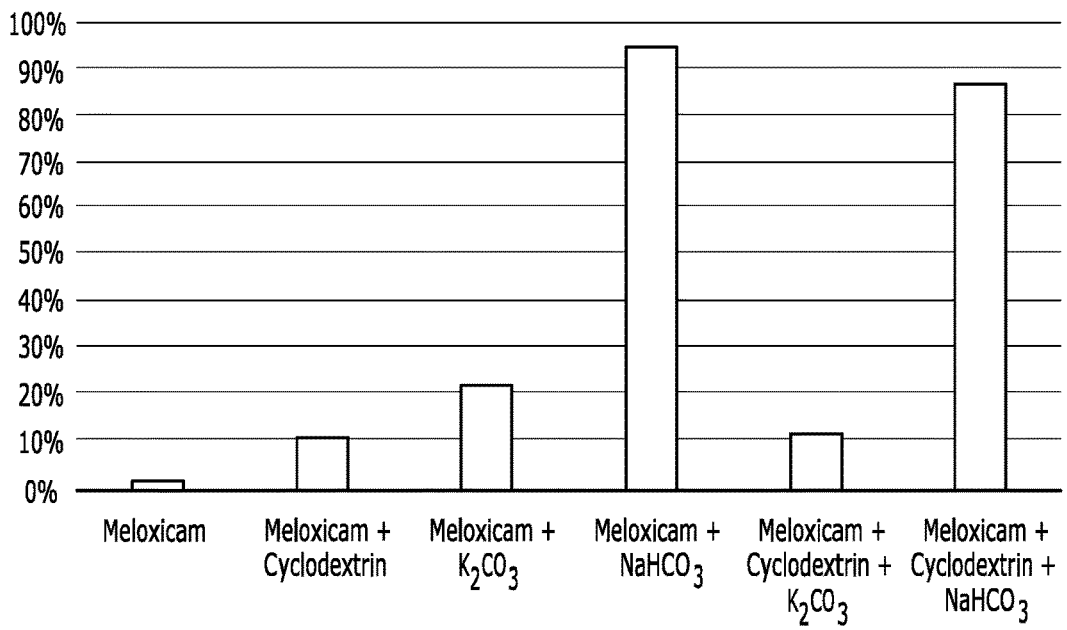
FIG. 10 is another depiction of the results described in Example 2 and contained in Table 6.

Provided herein are dosage forms with NSAIDs (such as meloxicam) and cyclodextrin (optionally in an inclusion complex), and/or bicarbonate, and methods of treatment using the dosage form.

A dosage form may be given enterally including, but not limited to, oral, sublingual, or rectal delivery, or parenterally including, but not limited to, intravenous, intramuscular, intranasal, or subcutaneous delivery.

Some methods include administration of a product that combines an NSAID that is formulated with: a) a cyclodextrin and/or b) a buffering agent. In some embodiments, the method involves treating a patient with a pharmaceutical formulation comprising meloxicam and a cyclodextrin and/or a carbonate/bicarbonate. Method embodiments may also include treating a patient to increase the bioavailability of meloxicam in the patient or increase the rate at which the meloxicam becomes bioavailable.

The combination of meloxicam, a cyclodextrin (such as SBEβCD), and a bicarbonate (such as sodium bicarbonate) may substantially increase the solubility and rate of absorption of meloxicam after oral administration, while maintaining its extended plasma concentration half-life in mammals, such as humans after oral administration.

The combination of meloxicam, a cyclodextrin (such as SBEβCD), and a bicarbonate (such as sodium bicarbonate) may substantially increase the oral bioavailability of meloxicam in mammals, such as humans, after oral administration.

Unless otherwise indicated, any reference to a compound herein, such as meloxicam or rizatriptan, by structure, name, or any other means, includes pharmaceutically acceptable salts, alternate solid forms, such as polymorphs, solvates, hydrates, enantiomers, tautomers, deuterium-modified forms, or any other chemical species, such as precursors, prodrugs, or any other chemical species that may rapidly convert to a compound described herein under conditions in which the compounds are used as described herein.

A subject combination may be given enterally including, but not limited to, oral, sublingual, or rectal delivery, or parenterally including, but not limited to, intravenous, intramuscular, intranasal, or subcutaneous delivery. In some embodiments, both meloxicam and rizatriptan are administered orally. In some embodiments, meloxicam is administered intravenously and rizatriptan is administered orally. In some embodiments, meloxicam is administered intramuscularly and rizatriptan is administered orally.

Normally, the combination of meloxicam and rizatriptan is administered so that the human being receives the meloxicam and rizatriptan within a short period of time with respect to one another. For example, the meloxicam and rizatriptan may be administered within about 2 hours, within about 1 hour, within about 30 minutes, within about 20 minutes, within about 15 minutes, within about 10 minutes, within about 5 minutes, or within about 1 minute of one another. In some embodiments, the meloxicam and rizatriptan are administered simultaneously, which for the purpose of this disclosure includes administration within about 5 minutes. In some embodiments, the meloxicam and rizatriptan are administered in a single dosage form.

The term "treating" or "treatment" broadly includes any kind of treatment activity, including the diagnosis, cure, mitigation, or prevention of disease in man or other animals, or any activity that otherwise affects the structure or any function of the body of man or other animals.

The dosage form or the subject combination may be used to treat, or provide relief of, any type of pain including, but not limited to, migraine and other types of headache, inflammatory pain, musculoskeletal pain, neuropathic pain, chronic pain, acute pain, localized pain, systemic pain, cancer-related pain, acute pain, pain due to injury, pain due to illness (e.g., fever), post-operative pain, etc. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. In some embodiments, the pain affects a muscle, nerve, cartilage, bone, ligament, tendon, tendon sheaths, bursae, or joint.

Migraine is a disabling neurological disorder characterized by recurrent attacks of pulsating head pain accompanied by nausea and sensitivity to light and sound. This pain may be moderate to severe, but is often severe and incapacitating, requiring bed rest. The headaches may affect one half of the head, may be pulsating in nature, and may last from 2 to 72 hours. Associated symptoms may include nausea, vomiting, and sensitivity to light (photophobia), sound (phonophobia), or smell. The migraine pain may be accompanied by disturbed vision. The migraine pain can be made worse by physical activity. Migraines may be associated with an aura, which may be a short period of visual disturbance which signals that the headache will soon occur. Some migraine patients may not have aura.

In some embodiments, the human being who is being treated for migraine pain suffers from allodynia, such as cutaneous allodynia with their migraine attacks. Allodynia, such as cutaneous allodynia, which is pain from normally non-painful stimuli (such as brushing hair, wearing glasses, taking a shower, etc.). Patients having allodynia, such as cutaneous allodynia are believed to be less likely to respond well to triptan medications.

Current treatments are suboptimal, with more than 70% of sufferers reporting dissatisfaction with existing acute treatments. The most commonly reported reasons for patient dissatisfaction are slow onset of pain relief, inconsistent pain relief, and recurrence of pain during the same day. Suboptimal acute treatment is associated with a significantly increased risk of new-onset chronic migraine, which may be prevented by improving acute treatment outcomes.

Administering a subject combination to a human being suffering from migraine, such as an acute attack of migraine pain or aura, may quickly result in a reduction in a migraine symptom, such as pain, nausea, vomiting, photophobia, or phonophobia, such as at or within about 5 minutes (intended as a shorthand for "at about 5 minutes, or within about 5 minutes"), at or within about 10 minutes, at or within about 30 minutes, at or within about 1 hour, at or within about 90 minutes, at or within about 2 hours, at or within about 2.5 hours, or at or within about 3 hours. In some embodiments, a human being experiences a reduction of, or complete relief from, pain, such as headache pain or migraine pain, nausea, vomiting, photophobia, and/or phonophobia, at or within about 1 hour, at or within about 90 minutes, at or within about 2 hours, at or within about 2.5 hours, or at or within about 3 hours. In some embodiments, the relief experienced, is greater than would be experienced by receiving the same amount of rizatriptan without meloxicam. In some embodiments, the relief experienced, is greater than would be experienced by receiving the same amount of meloxicam without rizatriptan.

The subject combination may be administered at the earliest sign of migraine pain, or soon after the earliest sign of migraine, such as within about 1 minute, within about 5 minutes, within about 10 minutes, within about 15 minutes, within about 20 minutes, within about 30 minutes, or within about 1 hour. At this early state, the pain may still be mild, or before the pain progresses to moderate or severe intensity. For some methods, the subject combination may be administered when the migraine pain has reached moderate or severe intensity.

The combination of meloxicam and rizatriptan may have distinct dual mechanisms of action for the acute treatment of migraine. Meloxicam is a potent, COX-2 preferential NSAID which is limited by slow absorption. Rizatriptan is a potent $5\text{-HT1}_{B/D}$ agonist believed to have efficacy in migraine.

Observation of relief or reduction in a symptom at a specific period of time, such as "at 2 hours," is useful because it allows the effectiveness of the treatment to be evaluated at a specific or consistent time point, which facilitates comparison between patients. Observation of relief or reduction in a symptom within a specific period of time, such as "within about 2 hours," is useful because it is desirable for relief or reduction of a symptom to occur as early as possible, and specifying that relief occur within a specified time sets a guideline in which it is desirable that relief occur.

For some methods, administration of the subject combination may achieve a reduction in migraine pain, nausea, vomiting, photophobia, or phonophobia that lasts at least about one hour, at least about two hours, at least about three hours, at least about four hours, at least about six hours, at least about eight hours, about 8-24 hours, about 24 hours, or more than 24 hours.

In some embodiments, the meloxicam and the rizatriptan are administered simultaneously (e.g. in a single dosage form, such as a single oral dosage form), and two hours after the meloxicam and the rizatriptan are administered, the human being experiences greater pain relief than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater pain relief than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater pain relief than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater pain relief than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from nausea than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from nausea than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from nausea than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from nausea than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from vomiting than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from vomiting than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from vomiting than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from vomiting than the human being would have experienced twenty-four hours after receiving the same amount of rizatriptan without the meloxicam. In some embodiments, the meloxicam and the rizatriptan are administered simultaneously (e.g. in a single dosage form, such as a single oral dosage form), and two hours after the meloxicam and the rizatriptan are administered, the human being experiences greater relief from photophobia than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from photophobia than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from photophobia than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from photophobia than the human being would have experienced twenty-four hours after receiving the same amount of rizatriptan without the meloxicam.

In some embodiments, the meloxicam and the rizatriptan are administered simultaneously (e.g. in a single dosage form, such as a single oral dosage form), and two hours after the meloxicam and the rizatriptan are administered, the human being experiences greater relief from phonophobia than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from phonophobia than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from phonophobia than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from phonophobia than the human being would have experienced twenty-four hours after receiving the same amount of rizatriptan without the meloxicam.

In some embodiments, the human being receiving the subject combination has a history of inadequate response to prior migraine treatments. For example, if the human being is asked whether he or she was pain-free within two hours of treatment for most attacks, and given the option of answering "never," "rarely," "less than half the time," or "half the time or more;" and the human being answers "never," "rarely," or "less than half the time," then the human being has had an inadequate response to the treatment. Similarly, if the human being is asked whether one dose of medication usually relieved the human being's headache and kept it away for at least 24 hours, and given the option of answering "never," "rarely," "less than half the time," or "half the time or more;" and the human being answers "never," "rarely," or "less than half the time," then the human being has had an inadequate response to the treatment.

In some embodiments, the human being receiving the subject combination has indicated that he or she was "never" pain-free within two hours of treatment for most attacks. In some embodiments, the human being receiving the subject combination has indicated that he or she was "rarely" pain-free within two hours of treatment for most attacks. In some embodiments, the human being receiving the subject combination has indicated that he or she was pain-free within two hours of treatment for most attacks "less than half the time."

In some embodiments, the human being receiving the subject combination has indicated that one dose of medication "never" relieved the respondent's headache and kept it away for at least 24 hours. In some embodiments, the human being receiving the subject combination has indicated that one dose of medication "rarely" relieved the respondent's headache and kept it away for at least 24 hours. In some embodiments, the human being receiving the subject combination has indicated that one dose of medication relieved the respondent's headache and kept it away for at least 24 hours "less than half the time."

In some embodiments, the human being receiving the subject combination has a history of inadequate response to prior migraine treatments as assessed by a total mean score of less than 7, less than 6, less than 5, less than 4, less than 3, less than 2, 1-2, 2-3, 3-4, 4-5, 5-6, or 6-7 on the Migraine Treatment Optimization Questionnaire (mTOQ-4). In some embodiments, the human being has had prior triptan use before receives the subject combination, such as a combination comprising meloxicam and rizatriptan.

In some embodiments, the human being receiving the subject combination, such as a combination comprising meloxicam and rizatriptan, has migraine, and may have a history of inadequate response to prior migraine treatments. In some embodiments, the human being having migraine does not have cluster headaches or other types of migraines. In some embodiments, the human being having migraine does not have chronic daily headache. In some embodiments, the human being having migraine does not have more than 15, 15-20, 20-25, 25-28, 28-30, or 30-31 non-migraine headache days per month. In some embodiments, the human being having migraine does not have a history of significant cardiovascular disease. In some embodiments, the human being having migraine does not have uncontrolled hypertension.

In some embodiments, the dosage form may also be administered to relieve arthritis pain. In some embodiments the dosage form may be administered to relieve other signs and/or symptoms of arthritis. Examples of arthritis include, but are not limited to, rheumatoid arthritis, juvenile rheumatoid arthritis (pauciarticular and polyarticular course), osteoarthritis, erosive osteoarthritis, sero-negative (non-rheumatoid), arthropathies, non-articular rheumatism, peri-articular disorders, axial spondyloarthritis, transient osteoarthritis of the hip, vertebral crush fractures, osteoporosis, and neuropathic arthropathies including Charcot's foot, axial spondyloarthritis including ankylosing spondylitis, and SAPHO syndrome. In other embodiments, the arthritis pain may be chronic or acute. In some embodiments the dosage form may be administered to relief the signs and/or symptoms of an arthritis including but not limited osteoarthritis For some methods, administration of the dosage form may achieve a reduction in pain that lasts at least about one hour, two hours, three hours, four hours, six hours, at least about eight hours, about eight to about 24 hours, or about 24 hours. In other embodiments, administration of the dosage form may achieve a reduction in pain that is observed at about 10 minutes, at about 30 minutes, at about one hour, at about two hours, at about three hours, at about four hours, at about five hours, at about six hours, at less than 15 minutes, at less than 20 minutes, 30 minutes, at less than one hour, at less than two hours, at less than three hours, at about 5, 10, 15, 20, 25, 30, 35, 40, 45, 50, or 60 minutes, or other time period bound by these ranges, after administration of the dosage form.

In some embodiments, the dosage form may also be administered to relieve neuropathic pain, including diabetic peripheral neuropathy, post-herpetic neuralgia, trigeminal neuralgia, monoradiculopathies, phantom limb pain, sciatica, pudendal neuralgia, and central pain. Other causes of neuropathic pain may include, but are not limited to, cancer-related pain, lumbar nerve root compression, spinal cord injury, post-stroke pain, central multiple sclerosis pain, HIV-associated neuropathy, and radio-therapy or chemotherapy associated neuropathy. The neuropathic pain treated may be chronic or acute.

In some methods, the dosage form may be administered to relieve inflammatory pain including inflammatory musculoskeletal pain, pain due to injury, arthritis pain, and complex regional pain syndrome. In other embodiments, the inflammatory pain may be chronic or acute.

Arthritis refers to inflammatory joint diseases that can be associated with pain. Examples of arthritis pain include but are not limited to pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome. The inflammatory joint disease treated may be chronic or acute.

For some methods, the meloxicam may be administered to relieve musculoskeletal pain. Examples of musculoskeletal pain may include, but are not limited to, back pain, low back pain (e.g., lumbosacral pain), neck pain, infection, cramps, tendonitis, epidondylitis, carpal tunnel syndrome, joint pain, fibromyalgia, pain due to injury, Tunnel syndromes, pain associated with bone fractures, sprains, fibrous dysplasia, osteogenesis imperfecta, Paget's disease of bone, transient osteoporosis, and transient osteoporosis of the hip. In other embodiments, the musculoskeletal pain may be chronic or acute.

For some methods, administration of the dosage form or the subject combination may achieve a reduction in pain that lasts at least about one hour, at least about two hours, at least about three hours, at least about four hours, at least about six hours, at least about eight hours, about 8 to about 24 hours, or about 24 hours. In other embodiments, administration of the subject combination may achieve a reduction in pain that is observed at about 10 minutes, at about 30 minutes, at about one hour, at about two hours, at about three hours, at about four hours, at about five hours, at about six hours, at or within about 5 minutes, at or within about 10 minutes, at or within about 15 minutes, at or within about 20 minutes, at or within about 25 minutes, at or within about 30 minutes, at or within about 35 minutes, at or within about 40 minutes, at or within about 45 minutes, at or within about 50 minutes, or at or within about 60 minutes, at two hours or less, at three hours or less, or other time period bound by these ranges, after administration of the subject combination.

A human being that is treated for a disease or condition with the dosage forms described herein may be of any age. For example the person may have an age of about 10 years to about 90 years, about 20 years to about 80 years, about 30 years to about 75 years, about 40 years to about 70 years, about 1 year to about 16 years, about 80 years to about 95 years, about 18 years or more, about 20 years or more, about 25 years or more, about 30 years or more, about 40 years or more, about 45 years or more, about 50 years or more, about 55 years or more, about 60 years or more, about 65 years or more, or any other age in a range bounded by, or between, these values.

In some embodiments, a human being who is treated for migraine with the dosage forms described herein, for example comprising meloxicam, rizatriptan, SBEβCD, and a bicarbonate such as sodium bicarbonate, may be of 18 years to 65 years of age, about 18-20 years of age, about 20-25 years of age, about 25-30 years of age, about 30-40 years of age, about 40-45 years of age, about 40-50 years of age, about 50-60 years of age, about 60-65 years of age, or any other age in a range bounded by, or between, these values.

In some embodiments, a human being who is treated for migraine with a dosage forms described herein, such as a dosage form comprising meloxicam, rizatriptan, SBEβCD, and a bicarbonate such as sodium bicarbonate, may be white, black or African American, or Asian.

In some embodiments, a human being that is treated for a disease or condition with a dosage form comprising meloxicam or another NSAID has suffered from the pain or condition associated with the pain for at least 1 day, at least one week, at least 2 weeks, at least 1 month, at least 6 weeks, at least 2 months, at least 3 months, at least 6 months, or at least 1 year, or any duration in a range bounded by, or between, these values.

In some embodiments, a human being that is treated for migraine with a dosage form comprising meloxicam and rizatriptan has been diagnosed of migraine with or without aura as defined by the ICHD-3 criteria for at least 3 months, at least 6 months, at least 1 year, at least 2 years, about 1-2 years, 2-3 years, or longer, or at least 1 year, or any duration in a range bounded by, or between, these values.

In some embodiments, a human being has an average 2 to 8, 2-3, 3-4, 4-5, 5-6, 6-7, or 7-8 moderate to severe migraines per month.

A cyclodextrin used in a dosage form with meloxicam could include a cyclodextrin, a cyclodextrin derivative, and/or a salt thereof. An inclusion complex of meloxicam and cyclodextrin may be more water-soluble relative to the non-complexed meloxicam. The cyclodextrin may be a naturally-occurring cyclodextrin (e.g., α, β, or γ-cyclodextrins) or a synthetic cyclodextrin. In some embodiments, α-cyclodextrins, derivatives, or salts thereof may be used. α-Cyclodextrins may include, but are not limited to, (2,3,6-tri-O-acetyl)-α-cyclodextrin, (2,3,6-tri-O-methyl)-α-cyclodextrin, (2,3,6-tri-O-octyl)-α-cyclodextrin, 6-bromo-6-deoxy-α-cyclodextrin, 6-iodo-6-deoxy-α-cyclodextrin, (6-O-tertbutyl-dimethylsilyl)-α-cyclodextrin, butyl-α-cyclodextrin, succinyl-α-cyclodextrin, (2-hydroxypropyl)-α-cyclodextrin, or combinations thereof.

In some embodiments, β-cyclodextrins, derivatives, or salts thereof may be used. β-cyclodextrins may include, but are not limited to, hydroxypropyl-β-cyclodextrin, 6-monodeoxy-6-monoamino-β-cyclodextrin, glucosyl-β-cyclodextrin, maltosyl-β-cyclodextrin, 6-O-α-D-glucosyl-β-cyclodextrin, 6-O-α-maltosyl-β-cyclodextrin, 6-azido-6-deoxy-β-cyclodextrin, (2,3-di-O-acetyl-6-O-sulfo)-β-cyclodextrin, methyl-β-cyclodextrin, dimethyl-β-cyclodextrin (DMβCD), trimethyl-β-cyclodextrin (TMβCD), (2,3-di-O-methyl-6-O-sulfo)-β-cyclodextrin, (2,6-di-O-methyl)-β-cyclodextrin, (2,6-di-O-ethyl)-β-cyclodextrin, (2,3,6-tri-O-methyl)-β-cyclodextrin, (2,3,6-tri-O-acetyl)-β-cyclodextrin, -(2,3,6-tri-O-benzoyl)-β-cyclodextrin, (2,3,6-tri-O-ethyl)-β-cyclodextrin, 6-iodo-6-deoxy-β-cyclodextrin, 6-(dimethyl-tert-butylsilyl)-6-deoxy-β-cyclodextrin, 6-bromo-6-deoxy-β-cyclodextrin, monoacetyl-β-cyclodextrin, diacetyl-β-cyclodextrin, triacetyl-β-cyclodextrin, (3-O-acetyl-2,6-di-O-methyl)-β-cyclodextrin, (6-O-maltosyl)-β-cyclodextrin, (6-O-sulfo)-β-cyclodextrin, (6-O-t-butyldimethylsilyl-2,3-di-O-acetyl)-β-cyclodextrin, succinyl-(2-hydroxypropyl)-β-cyclodextrin, (2,6-di-O-)ethyl-β-cyclodextrin, (2-carboxyethyl)-β-cyclodextrin (CMEβCD), hydroxyethyl-β-cyclodextrin (HEβCD), (2-hydroxypropyl)-β-cyclodextrin, (2-hydroxypropyl)-β-cyclodextrin (HPβCD), (3-hydroxypropyl)-β-cyclodextrin (3HPβCD), (2,3-hydroxypropyl)-β-cyclodextrin (DHPβCD), butyl-β-cyclodextrin, methyl-β-cyclodextrin, silyl((6-O-tert-butyldimethyl)-2,3, -di-O-acetyl)-β-cyclodextrin, succinyl-β-cyclodextrin, (2-hydroxyisobutyl)-β-cyclodextrin, randomly methylated-β-cyclodextrin, branched-β-cyclodextrin, or combinations thereof.

In other embodiments, a β-cyclodextrin may be a sulfoalkyl ether cyclodextrin, derivative, or salt thereof. Examples of sulfoalkyl ether cyclodextrin derivatives may include, but are not limited to, sulfobutyl ether-β-cyclodextrin (e.g., SBEβCD, betadex, CAPTISOL®). In some embodiments, a SBEβD may have about 4-8, about 5-8, about 4-7, about 6-7, or about 6.5 sulfobutyl ether groups per cyclodextrin molecule.

In some embodiments, γ-cyclodextrins, derivatives, or salts thereof may be used. γ-cyclodextrins may include carboxymethyl-γ-cyclodextrin, (2,3,6-tri-O-acetyl)-γ-cyclodextrin, (2,3,6-tri-O-methyl)-γ-cyclodextrin, (2,6-di-O-pentyl)-γ-cyclodextrin, 6-(dimethyl-tert-butylsilyl)-6-deoxy-γ-cyclodextrin, 6-bromo-6-deoxy-γ-cyclodextrin, 6-iodo-6-deoxy-γ-cyclodextrin, (6-O-t-butyldimethylsilyl)-γ-cyclodextrin, succinyl-γ-cyclodextrin, hydroxypropyl-γ-cyclodextrin (2-hydroxypropyl)-γ-cyclodextrin, acetyl-γ-cyclodextrin, butyl-γ-cyclodextrin, or combinations thereof.

In some embodiments, the dosage form may include a bicarbonate, such as sodium bicarbonate, potassium bicarbonate, magnesium bicarbonate, calcium bicarbonate, ammonium bicarbonate, or a combination thereof. A bicarbonate may help to increase bioavailability of the meloxicam.

In other embodiments, the dosage form may include a carbonate, derivatives, or salts thereof. Examples of carbonates may include aluminum carbonate, ammonium carbonate, barium carbonate, calcium carbonate, cobalt(II) carbonate, lanthanum carbonate, lithium carbonate, magnesium carbonate, manganese(II) carbonate, potassium carbonate, sodium carbonate, or combinations thereof.

In some embodiments, enhanced bioavailability of the dosage form may be achieved in treating one of these conditions by administering a dosage form comprising a salt form of the meloxicam, by creating an inclusion complex with meloxicam and cyclodextrin, and/or by including a bicarbonate. This may allow a reduced molar amount of the meloxicam to be used as compared to other meloxicam dosage forms.

Unless otherwise indicated, any reference to a compound herein, such as meloxicam or a cyclodextrin, by structure, name, or any other means, includes pharmaceutically acceptable salts, alternate solid forms, such as polymorphs, solvates, hydrates, enantiomers, tautomers, deuterium-modified forms, or any other chemical species that may rapidly convert to a compound described herein under conditions in which the compounds are used as described herein.

In some embodiments, use of a cyclodextrin, a carbonate, or a bicarbonate may improve the oral bioavailability of meloxicam by at least about 10%, at least about 20%, at least about 30%, at least about 40%, at least about 50%, at least about 60%, at least about 70%, at least about 80%, at least about 90%, up to about 100%, up to about 200%, or any amount in a range bounded by, or between, these values as compared to administration of meloxicam alone.

Due to the improved bioavailability, the dosage form may contain, or a subject may receive, on a molar basis, less of the meloxicam than would otherwise be administered. For example, a dosage form may contain, or a mammal may receive, at least about 10 mole % less, at least about 20 mole % less, at least about 30 mole % less, at least about 40 mole % less, at least about 50 mole % less, at least about 60 mole % less, at least about 70 mole % less, at least about 80 mole % less, at least about 85 mole % less, and/or up to about 90 mole % less, 95 mole % less, or any amount in a range bounded by, or between, these values as would otherwise be administered of meloxicam.

In other embodiments, use of other NSAIDs, opioids, or other pain medications may be reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, up to about 100%, as compared to the use of other NSAIDs, opioids or other pain medications without administration of meloxicam with cyclodextrin, carbonate, and/or bicarbonate.

In some embodiments, a dosage form may contain meloxicam in an amount from about 1-50 mg; about 1-10 mg; about 1-5 mg; about 10-40 mg; about 1-35 mg; about 1-25 mg; about 1-15 mg; about 5-20 mg; about 5-10 mg; about 5-15 mg; about 10-20 mg; about 20-30 mg; about 30-40 mg; about 40-50 mg; about 5 mg; about 7.5 mg; about 10 mg; about 15 mg; about 30 mg; or any amount in a range bounded by, or between, any of these values. These doses may be a safe dose for repeated administration, such as once hourly dosing to once daily dosing, twice daily dosing, dosing one to 12 times daily, doing 3, 4, 5, or 6 times daily, etc. In some embodiments, the meloxicam may be safely administered 2, 3, 4, 5, 6, 7, 8, 9, 10, 11, 12, 13, 14, or 15 times, or about 3 to about 10 times a day, once a day, or less frequently, such as once a week, once every two weeks, once a month, etc.

For some dosage forms, meloxicam forms a complex with the substituted-β-cyclodextrin or other another cyclodextrin which may be formulated into a solid dosage form. Such a dosage form may be suitable for oral administration. A meloxicam-cyclodextrin inclusion complex may also be dissolved in water or another solvent to form a parenteral formulation. However, physical mixtures of meloxicam and the substituted-β-cyclodextrin or other cyclodextrins may also be used in oral or parenteral dosage forms.

Formation of an inclusion complex of meloxicam and a cyclodextrin may help to improve the properties of a dosage form. For some inclusion complexes, the meloxicam and the cyclodextrin (e.g., SBEβCD) may have a molar ratio of about 0.5-2 (a molar ratio of 0.5 is 0.5 moles of meloxicam to 1 mole of cyclodextrin), about 0.5-0.7, about 0.6-0.8, about 0.7-0.9, about 0.8-1, about 0.9-1.1, about 1-1.2, about 1.1-1.3, about 1.2-1.4, about 1.3-1.5, about 1.4-1.6, about 1.5-1.7, about 1.6-1.8, about 1.7-1.9, about 1.8-2, about 0.8-1.2, about 1, or any ratio in a range bounded by any of these values.

For some dosage forms, a cyclodextrin (e.g., SBEβCD) may be employed in a weight ratio to the meloxicam within the range from about 1-1000 (e.g. 1 g of cyclodextrin per 1 g of meloxicam is a weight ratio of 1); about 1-20; about 1-10; about 1-15; about 2-4, about 3-5, about 4-6, about 5-7, about 6-8, about 7-9, about 8-10, or any weight ratio in a range bounded by, or between, any of these values. For some dosage forms, a cyclodextrin (e.g., SBEβCD) may be employed in a weight ratio to the meloxicam within the range from about 0.001-1 (e.g. 0.1 g of cyclodextrin per 1 g of meloxicam is a weight ratio of 0.1); about 0.01-1; about 0.05-1; about 0.1-1; about 0.2-1; about 0.3-1, about 0.4-1, about 0.5-1, about 0.6-1, about 0.7-1, about 0.8-1, or any weight ratio in a range bounded by, or between, any of these values. Each type of cyclodextrin employed may have a different ratio.

For some dosage forms, the cyclodextrin may be present in an amount from about 1-200 mg; 25-175 mg; about 50-150 mg; about 25-100 mg; about 75-150 mg; about 100-175 mg; about 20-80 mg; about 25-50 mg; about 60-100 mg; about 80-100 mg; about 80-120 mg; about 100-120 mg; about 100-140 mg; about 120-160 mg; about 140-180 mg; about 30-90 mg; about 40-80 mg; about 50-70 mg, about 55-65 mg, about 60-62 mg, or any amount in a range bounded by, or between, any of these values.

For some methods, the inclusion complex of meloxicam and cyclodextrin such as a substituted-β-cyclodextrin is delivered orally (for example by tablet, capsule, elixir, or the like). Other potential routes of administration include intravenous, intramuscular, intranasal, lyophilized parenteral, subcutaneous, transdermal, transmucosal, or through other parenteral means. The meloxicam may also be delivered alone or non-complexed with cyclodextrin.

Some dosage forms contain a bicarbonate (e.g., sodium bicarbonate) in amount from about 1-2000 mg; about 1-1000 mg; about 100-1000 mg; about 200-800 mg; about 1-500 mg; about 1-200 mg; about 1-100 mg; about 50-750 mg; about 500-1000 mg; about 100-500 mg; about 100-300 mg; about 500-1000 mg; about 300-700 mg; about 400-600 mg; about 50-250 mg; about 250-750 mg; about 100-200 mg; about 200-300 mg; about 300-400 mg; about 400-500 mg; about 410-510 mg; about 420-520 mg; about 430-530 mg; about 440-540 mg; about 450-550 mg; about 460-560 mg; about 470-570 mg; about 480-580 mg; about 490-590 mg; about 500-600 mg; about 600-700 mg; about 700-800 mg; about 800-900 mg; about 150-650 mg; about 350-850 mg; or any amount in a range bounded by, or between, any of these values.

Some dosage forms contain a carbonate in amount from about 1-1000 mg; about 1-500 mg; about 1-200 mg; about 1-100 mg; about 50-750 mg; about 500-1000 mg; about 100-500 mg; about 100-300 mg; about 200-800 mg; about 500-1000 mg; about 300-700 mg; about 400-600 mg; about 50-250 mg; about 250-750 mg; about 100-200 mg; about 200-300 mg; about 300-400 mg; about 400-500 mg; about 500-600 mg; about 600-700 mg; about 700-800 mg; about 800-900 mg; about 150-650 mg; about 350-850 mg; or any amount in a range bounded by, or between, any of these values.

In some embodiments, the daily dose of meloxicam (e.g., an oral dose, a parenteral dose, etc.) is about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 5-10 mg, about 10-15 mg, about 15-20 mg, about 20-25 mg, about 25-30 mg, about 30-35 mg, or any amount in a range bounded by any of these values.

In some embodiments, the weekly dose of meloxicam (e.g., an oral dose) is about 1-1000 mg; about 1-500 mg; about 10-250 mg; about 100-300 mg; about 10-100 mg; about 10-150 mg; about 10-300 mg; about 20-150 mg; about 20-60 mg; about 30-70 mg; about 40-60 mg; about 50-70 mg; about 70-90 mg; about 90-110 mg; about 50 mg; about 55 mg; about 100-150 mg; about 30-100 mg; or any amount in a range bounded by, or between, any of these values. The weekly dose may be given as a single dose, given once during the week, or may be given in 2, 3, 4, 5, 6, or 7 individual doses during the week.

In some embodiments, the monthly dose of meloxicam (e.g., an oral dose), or a dose administered over a period of a month, is about 5000 mg or less; about 4000 mg or less; about 3000 mg or less; about 2000 mg or less; about 1000 mg or less; about 700 mg or less; about 600 mg or less; about 1-4000 mg; about 1-1000 mg; about 10-1000 mg; about 50-1000 mg; about 10-600 mg; about 40-600 mg; about 50-600 mg; about 40-400 mg; about 50-200 mg; about 200-240 mg; about 240-280 mg; about 280-320 mg; about 320-360 mg; about 360-400 mg; about 400-450 mg; about 450-500 mg; about 500-600 mg; about 250-350 mg; about 100-600 mg; about 40-2000 mg; about 40-800 mg; about 100-900 mg; about 100-800 mg; about 40-1000 mg; about 50-1000 mg; about 100-1000 mg; or any monthly dose in a range bounded by, or between, any of these values. A monthly dose may be given as a single dose, or as two or more individual doses administered during the month. In some embodiments, the monthly dose is administered in 2 or 3 bi-weekly doses. In some embodiments, the monthly dose is administered in 4 or 5 weekly doses. In some embodiments, the monthly dose is administered in 28 to 31 daily doses, or in 56 to 62 daily doses or more. In some embodiments, the monthly dose is administered in 5 to 15 individual doses during the month. The monthly dose may be administered for only 1 month, or may be repeatedly administered for 2 or more months.

In other embodiments, the dosage form may be administered weekly for about one, two, three, four, or more consecutive weeks, every other week or bi-weekly, or once every three weeks. This regimen may be repeated once weekly, twice in a month, three times in a month, once monthly, once every two months, once every three months, or as directed by a medical professional.

In certain embodiments, the pharmaceutical composition results in increased bioavailability (e.g., reduced $T_{max}$, increased $C_{max}$, increased AUC, etc.) of the meloxicam from the dosage form as compared to a dosage form containing meloxicam but not containing a cyclodextrin, an acid inhibitor, or a buffering agent (such as a bicarbonate). In some embodiments, the bioavailability of meloxicam will increase with multiple dosing. For example, the bioavailability of meloxicam in the dosage form may increase after about 1-10 days of dosing; about 2-6 days of dosing; about 3-5 days of dosing; about 4-6 days of dosing; about 5-8 days of dosing; about 5 days of dosing; about 6 days of dosing; about 7 days of dosing; about 8 days of dosing; about 10 days of dosing; about 15 days of dosing; or time in any range bounded by, or between, any of these values; as compared to the bioavailability of meloxicam in a dosage form not containing a cyclodextrin, an acid inhibitor, or a buffering agent (such as a bicarbonate).

Some of the dosage forms may result in a desired range for an area under the plasma concentration curve (AUC) of meloxicam. For example the dosage with meloxicam may result in an AUC of meloxicam of about 1-150 μg·hr/mL; about 10-30 μg·hr/mL; about 20-40 μg·hr/mL; about 30-50 μg·hr/mL; about 40-60 μg·hr/mL; about 50-70 μg·hr/mL; about 60-80 μg·hr/mL; about 70-90 μg·hr/mL; about 80-100 μg·hr/mL; about 10-100 μg·hr/mL; about 50-150 μg·hr/mL; about 25-125 μg·hr/mL; about 75-150 μg·hr/mL; about 20-50 μg·hr/mL; about 40-70 μg·hr/mL; about 60-90 μg·hr/ mL; about 80-110 µg·hr/mL; about 100-130 µg·hr/mL; about 120-150 µg·hr/mL; or any AUC in a range bounded by, or between, any of these values.

Unless otherwise indicated, the AUC refers to the AUC calculated to the last measured concentration ($AUC_{0-t}$), such as, over a period of 6 hours ($AUC_{0-6}$), over a period of 12 hours ($AUC_{0-12}$), over a period of 24 hours ($AUC_{0-24}$), or extrapolated to infinity ($AUC_{0-inf}$).

In Example 3 below, the $AUC_{0-24}$ of meloxicam in human beings for an oral dosage form containing sodium bicarbonate and sulfobutylether β-cyclodextrin (SBEβCD) was about 27 µg·hr/mL. This dosage form contained 15 mg of meloxicam.

The 15 mg IV and intramuscular doses also provide an $AUC_{0-24}$ of meloxicam in human beings that is about 27 µg·hr/mL. The AUC of meloxicam is believed to be approximately dose proportional. So for this oral dosage form, or for an IV or intramuscular dosage form, a meloxicam dose of, for example, approximately 17 mg to about 30 mg would be expected to result in an $AUC_{0-24}$ of meloxicam of about 30-50 µg·hr/mL.

For some acute pain conditions, such as migraine and other types of headache, the AUC for a short period after oral administration, such as an AUC measured over 6 hours (or $AUC_{0-6}$), may be of particular interest. For example, some dosage forms may result in an $AUC_{0-6}$ of at least about 6 µg·hr/mL; at least about 7 µg·hr/mL; at least about 8 µg·hr/mL; at least about 9 µg·hr/mL; about 6-10 µg·hr/mL; about 7-11 µg·hr/mL; about 8-12 µg·hr/mL; about 9-13 µg·hr/mL; or any AUC in a range bounded by, or between, any of these values.

In some embodiments, the dosage form may result in a $C_{max}$ of meloxicam of about 10-2500 ng/mL; about 100-2250 ng/mL; about 500-2000 ng/mL; about 1000-2500 ng/mL; about 1000-2000 ng/mL; about 100-900 ng/mL; about 750-1500 ng/mL; about 1250-2000 ng/mL; about 1500-2300 ng/mL; about 800-1200 ng/mL; about 1900-2400 ng/mL; about 50-500 ng/mL; about 400-950 ng/mL; about 900-1500 ng/mL; about 1100-2200 ng/mL; about 1300-1600 ng/mL; about 1200-1500 ng/mL; about 1400-2100 ng/mL; about 1500-1900 ng/mL; about 1600-2100 ng/mL; about 1700-2000 ng/mL; about 1800-2000 ng/mL; about 1900-2500 ng/mL; about 150-1700 ng/mL; about 1600-1800 ng/mL; about 1700-1900 ng/mL; about 1800-2000 ng/mL; about 1900-2100 ng/mL; about 2000-2200 ng/mL; about 2100-2300 ng/mL; about 2200-2400 ng/mL; about 2300-2500 ng/mL; about 2500-3000 ng/mL; or any $C_{max}$ in a range bounded by, or between, any of these values.

For example, a method described herein may reduce the $T_{max}$ of meloxicam. In some embodiments, the method may include treating a patient to achieve the $T_{max}$ of meloxicam in the patient within about 10 minutes; about 20 minutes; about 30 minutes; about 40 minutes; about 50 minutes; about 60 minutes; about 70 minutes; about 80 minutes; about 90 minutes; about 100 minutes; about 110 minutes; about 120 minutes; about 180 minutes; about 1-10 hr; about 2-9 hr; about 3-7 hr; about 4-6 hr; about 1-5 hr; about 2-7 hr; about 3-8 hr; about 4-9 hr; about 1-4 hr; about 2-5 hr; about 3-6 hr; about 4-7 hr; about 5-8 hr; about 6-9 hr; about 7-10 hr; after administration or any $T_{max}$ in a range bounded by, or between, any of these values.

In some embodiments, an oral dosage form may have a $T_{max}$ of meloxicam that is shorter than would be achieved by administering meloxicam by intramuscular injection. In some embodiments, an oral dosage form may have a $T_{max}$ of meloxicam that is shorter, or may increase meloxicam plasma levels at a faster rate, by a factor of at least about 1.5, about 2, about 3, about 4, about 5, about 6, about 7, about 8, about 9, about 10, about 12, about 15, about 20, or by a factor of about 1.5-1000, about 2-100, about 3-100, about 4-100, about 5-100, about 6-100, about 7-100, about 8-100, about 9-100, about 10-100, about 12-100, about 15-100, about 20-100, or by a factor in a range bounded by any of these values.

The oral dosage form of Example 3 below gave a $T_{max}$ of meloxicam of approximately 30 minutes. The reported $T_{max}$ of intravenous meloxicam is approximately 30 minutes for an infusion or 3 minutes for a bolus. The reported $T_{max}$ of intramuscular meloxicam is approximately 60-84 minutes.

In some embodiments, a dosage form comprising meloxicam may result in a plasma concentration of meloxicam at 12 hours that is about 0.01-0.5 µg/mL; about 0.5-0.7 µg/mL; about 0.6-0.8 µg/mL; about 0.7-0.9 µg/mL; about 0.8-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1.9-2.1 µg/mL; about 2-2.2 µg/mL; about 2.1-2.3 µg/mL; about 2.2-2.4 µg/mL; about 2.3-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; or any plasma concentration in a range bounded by, or between, any of these values.

In some embodiments, meloxicam is administered at a dose that results in a meloxicam plasma level (such as a $C_{avg}$, or average plasma level) of about 0.01-0.5 µg/mL; about 0.5-0.7 µg/mL; about 0.6-0.8 µg/mL; about 0.7-0.9 µg/mL; about 0.8-1 µg/mL; about 0.9-1.1 µg/mL; about 1-1.2 µg/mL; about 1.1-1.3 µg/mL; about 1.2-1.4 µg/mL; about 1.3-1.5 µg/mL; about 1.4-1.6 µg/mL; about 1.5-1.7 µg/mL; about 1.6-1.8 µg/mL; about 1.7-1.9 µg/mL; about 1.8-2 µg/mL; about 1.9-2.1 µg/mL; about 2-2.2 µg/mL; about 2.1-2.3 µg/mL; about 2.2-2.4 µg/mL; about 2.3-2.5 µg/mL; about 2.4-2.6 µg/mL; about 2.5-2.7 µg/mL; about 2.6-2.8 µg/mL; about 2.7-2.9 µg/mL; about 2.8-3 µg/mL; about 2.9-3.1 µg/mL; about 3-3.2 µg/mL; about 3.1-3.3 µg/mL; about 3.2-3.4 µg/mL; about 3.3-3.5 µg/mL; about 3.4-3.6 µg/mL; about 3.5-3.7 µg/mL; about 3.6-3.8 µg/mL; about 3.7-3.9 µg/mL; about 3.8-4 µg/mL; about 0.1-20 µg/mL; about 0.5-15 µg/mL; about 0.5-10 µg/mL; about 5-15 µg/mL; about 10-20 µg/mL; about 7.5-15 µg/mL; about 2-10 µg/mL; about 1-8 µg/mL; about 1-6 µg/mL; about 1-2 µg/mL; about 0.5-3.5 µg/mL; about 0.5-7 µg/mL; about 12-20 µg/mL; about 8-12 µg/mL; about 1-4 µg/mL; about 4-7 µg/mL; about 7-11 µg/mL; about 11-15 µg/mL; about 15-19 µg/mL; about 16-20 µg/mL; or any amount of meloxicam plasma level in a range bounded by, or between, any of these values.

Administration of a dosage form described herein may result in a decreased time to therapeutic plasma concentration of meloxicam. The therapeutic plasma concentration is the $C_{avg}$ for a 15 mg dose of Mobic® meloxicam. In some embodiments, the time to therapeutic plasma concentration of meloxicam ($T_{thera}$) is about 10-30 minutes, about 10-15 minutes, about 15-20 minutes, about 20-25 minutes, about 25-30 minutes, about 10-20 minutes, about 20-30 minutes, about 16-18 minutes, or about 17 minutes.

A method described herein may reduce the $T_{max}$ of rizatriptan. For example, the method may achieve a $T_{max}$ of rizatriptan in the patient within about 50 minutes; within about 60 minutes; within about 70 minutes; within about 80 minutes; or within about 90 minutes; at about 40-60 minutes, at about 40-45 minutes, at about 45-50 minutes, at about 50-55 minutes, or about 55-60 minutes after administration, or any $T_{max}$ in a range bounded by any of these values.

In some embodiments, the meloxicam and the rizatriptan are administered simultaneously (e.g. in a single dosage form, such as a single oral dosage form), and two hours after the meloxicam and the rizatriptan are administered, the human being experiences greater relief from allodynia, such as cutaneous allodynia than the human being would have experienced two hours after receiving the same amount of meloxicam without the rizatriptan.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from allodynia, such as cutaneous allodynia than the human being would have experienced twenty-four hours after receiving the same amount of meloxicam without the rizatriptan.

In some embodiments, the meloxicam and the rizatriptan are administered simultaneously (e.g. in a single dosage form, such as a single oral dosage form), and two hours after the meloxicam and the rizatriptan are administered, the human being experiences greater relief from allodynia, such as cutaneous allodynia than the human being would have experienced two hours after receiving the same amount of rizatriptan without the meloxicam.

In some embodiments, the meloxicam and the rizatriptan are administered simultaneously (e.g. in a single dosage form, such as a single oral dosage form), and twenty-four hours after the meloxicam and the rizatriptan are administered, the human being experiences greater relief from allodynia, such as cutaneous allodynia than the human being would have experienced twenty-four hours after receiving the same amount of rizatriptan without the meloxicam.

One embodiment is a method for reducing the risk of gastrointestinal side effects in people taking NSAIDs for pain relief and for other conditions, particularly during chronic treatment, and improving the bioavailability of the NSAID. In one embodiment, the method involves the administration of a product that combines: a) an agent that actively raises intragastric pH; and b) an NSAID that is formulated with a cyclodextrin. In another embodiment, the method involves the administration of a product that combines: a) an agent that actively raises intragastric pH; b) an NSAID that is formulated with a cyclodextrin; and c) a buffering agent. Either short or long acting acid inhibitors can be effectively used in the dosage forms. This method has the added benefit of being able to protect patients from other gastrointestinal ulcerogens whose effect may otherwise be enhanced by the disruption of gastroprotective prostaglandins due to NSAID therapy.

The meloxicam formulation in an aqueous parenteral form may include a buffer to adjust the pH of an aqueous formulation, within a range of about 2 to about 5; about 3.5 to about 5; about 5 to about 11; about 6 to about 9; about 6 to about 8; about 6 to about 7; or any other pH in a range bounded by, or between, any of these values. The meloxicam formulation in an oral form may include a buffer to adjust the pH of stomach fluid within a range of about 2 to about 5; about 3.5 to about 5; about 5 to about 11; about 6 to about 9; about 6 to about 8; about 6 to about 7; or any other pH in a range bounded by, or between, any of these values. Examples of buffers suitable for use herein include sulfate buffers, phosphate buffers, borate buffers, carbonate buffers, citrate buffers, etc.

In some embodiments, the dosage form may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non-toxic in the amounts employed.

Some compositions or dosage forms may be a liquid, or may comprise a solid phase dispersed in a liquid.

The dosage form may further comprise a second therapeutically active agent, such as an acid inhibitor or an analgesic.

In some embodiments, the dosage form may further comprise an acid inhibitor present in an amount effective to raise the gastric pH of a patient to at least 2, to at least 2.5, to at least 3, to at least 3.5, to at least 4, and more to at least 5, when one or more unit dosage forms are administered. The term "acid inhibitor" refers to agents that inhibit gastric acid secretion and increase gastric pH. Specific $H_2$ blockers, also referred to as $H_2$ antagonists or histamine $H_2$ blockers or antagonists, that may be used include but are not limited to cimetidine, ranitidine, ebrotidine, pabutidine, lafutidine, loxtidine, famotidine, or combinations thereof.

Other agents that may be effectively used as acid inhibitors are the proton pump inhibitors such as omeprazole, esomeprazole, pantoprazole, lansoprazole, dexlansoprazole, rabeprazole, pariprazole, leminoprazole and tenatoprazole. In some embodiments the daily dose of the acid inhibitor is about 1-200 mg, about 1-100 mg, about 1-50 mg, about 40-80 mg, about 5-50 mg, about 20-40 mg, about 10-50 mg, about 10-20 mg, about 20-40 mg, about 15-50 mg, about 30-60 mg, about 10 mg, about 20 mg, about 30 mg, about 40 mg or any other amount in a range bounded by, or between, any of these values.

Examples of particular proton pump inhibitors include esomeprazole, present in unit dosage forms in an amount of between 5 mg and 50 mg; omeprazole, present in unit dosage forms in an amount of between 5 mg and 50 mg; lansoprazole, present in unit dosage forms in an amount of between 5 mg and 150 mg (and preferably at between 5 mg and 30 mg); and pantoprazole, present in unit dosage forms in an amount of between 10 mg and 200 mg. In some embodiments, the proton pump inhibitor is present in the dosage form in an amount of about 10-30 mg, about 20-40 mg, about 30-50 mg, about 40-60 mg, about 50-70 mg, about 60-80 mg, about 70-90 mg, or about 80-100 mg. Recently, a newer class of acid inhibitor has been developed which competes with potassium at the acid pump. The compounds in this class have been referred to as "reversible proton pump inhibitors" or "acid pump antagonists" and may also be used. Examples include AZD-0865, AR-H047108, CS-526, pumaprazole, revaprazan and soraprazan (see WO9605177 and WO9605199). Other compounds in this group are H-335/25 (AstraZeneca, Dialog file 128, accession number 020806); Sch-28080 (Schering Plough, Dialog file 128, accession number 009663); Sch-32651 (Schering Plough, Dialog file 128, accession number 006883) and SK&F-96067 (CAS Registry no. 115607-61-9).

The second therapeutically active agent may include an analgesic such as a second non-steroidal anti-inflammatory drug, an opioid, a steroid, a triptan, etc. In some embodiments, the dosage form or treatment also further comprises administering a second non-steroidal anti-inflammatory drug in an amount effective to reduce or eliminate pain or inflammation. The NSAID may include, but is not limited to, celecoxib, rofecoxib, lumiracoxib, valdecoxib, parecoxib, etoricoxib, CS-502, JTE-522, L-745,337, NS398, aspirin, acetaminophen (considered to be an NSAID for the purposes of the present disclosure), ibuprofen, flurbiprofen, ketoprofen, naproxen, oxaprozin, etodolac, indomethacin, ketorolac, lornoxicam, meloxicam, piroxicam, droxicam, tenoxicam, nabumetone, diclofenac, meclofenamate, mefenamic acid, diflunisal, sulindac, tolmetin, fenoprofen, suprofen, benoxaprofen, aceclofenac, tolfenamic acid, oxyphenbutazone, azapropazone, phenylbutazone, or combinations thereof. It will be understood that, for the purposes of the present disclosure, reference to an acid inhibitor, NSAID, or analgesic agent will include all of the common forms of these compounds and, in particular, their pharmaceutically acceptable salts. The amounts of NSAIDs which are therapeutically effective may be lower in the current embodiments than otherwise found in practice due to potential positive kinetic interaction and NSAID absorption in the presence of an acid inhibitor, and or in the presence of a buffering agent.

In other embodiments, the dosage form or treatment may further comprise administering an opioid in an amount effective to reduce or eliminate pain or inflammation. The opioid may include, but is not limited to, (dextro)propoxyphene, A-methylfentanyl, alfentanil, allylprodine, bezitramide, buprenorphine, butorphanol, carfentanyl, desmethylprodine, dextromoramide, dezocine, diacetylmorphine, dihydrocodeinone, dihydroetorphine, dimorphone, diphenoxylate, dipipanone, etorphine, fentanyl, ketobemidone, lefetamine, levacetylmethadol, levomethorphan, levorphanol, loperamide, meperidine, meptazinol, methadone, methylmorphine, morphine, nalbuphine, nalmefene, naloxone, naltrexone, nicomorphine, ohmefentanyl, oripavine, oxycodone, oxymorphone, PEPAP, paramorphine, pentazocine, phenazocine, piritramide, prodine, remifentanil, sufentanil, tapentadol, tilidine, tramadol, or combinations thereof.

Useful triptans may include sumatriptan, rizatriptan, naratriptan, eletriptan, donitriptan, almotriptan, frovatriptan, alvitriptan, zolmatriptan, etc. In some embodiments, the triptan comprises rizatriptan. In some embodiments, the dosage form may contain about 1-5 mg, about 2-6 mg, about 3-7 mg, about 4-8 mg, about 5-10 mg, about 6-11 mg, about 7-12 mg, about 8-13 mg, about 9-14 mg, about 10-15 mg, about 15-20 mg, or about 20-30 mg, of the triptan, such as rizatriptan, or any amount in a range bounded by any of these values.

In some embodiments; a dosage form comprising the subject combination may contain rizatriptan in an amount of about 1-50 mg; about 1-10 mg; about 10-20 mg; about 20-30 mg; about 30-40 mg; or about 40-50 mg; about 10-40 mg; about 1-35 mg; about 1-25 mg; about 1-15 mg; about 1-10 mg; about 5-20 mg; about 1-5 mg; about 2-6 mg; about 3-7 mg; about 4-8 mg; about 5-10 mg; about 6-11 mg; about 7-12 mg; about 8-13 mg; about 9-11 mg; about 9-14 mg; about 10-15 mg; about 11-16 mg; about 12-17 mg; about 13-18 mg; about 14-19 mg; about 15-20 mg; about 5-15 mg; about 0.5 mg; about 1 mg; about 1.5 mg; about 2 mg; about 2.5 mg; about 3 mg; about 3.5 mg; about 4 mg; about 4.5 mg; about 5 mg; about 6 mg; about 7 mg; about 7.5 mg; about 8 mg, about 9 mg, about 10 mg; about 15 mg; about 20 mg, about 25 mg, about 30 mg; or any amount in a range bounded by, or between, any of these values.

For acute migraines, the amount of meloxicam and/or rizatriptan in a single dose, or the AUC of the meloxicam and/or rizatriptan associated with a single dose, is of particular interest. For example, after a single dose, the symptoms may be relieved for an extended period of time, such that, in the short term, repeated doses may not be needed. For more continuous conditions, including more chronic, continuous, or frequent migraine symptoms, daily, weekly, or monthly doses may be of particular interest.

For any amounts of rizatriptan described herein, salt forms of rizatriptan may be present in the amounts recited above, or amounts that are molar equivalents to these amounts for the rizatriptan free base. For example, assuming that the molecular weight of rizatriptan free base is 269.3 g/mol, 10 mg of rizatriptan is 37.1 mmol of rizatriptan. Thus, a molar equivalent of 10 mg of rizatriptan free base would be the mass of 37.1 mmol of that salt form. For example, for the benzoate salt (mw=391.2 g/mol), the molar equivalent of 10 mg of the free base (or 37.1 mmol), would be 14.5 mg. These doses may be safe for repeated administration, such as 1, 2, 3, or 4 times a day, or repeated at an interval of 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 4 weeks, 4-6 weeks, about 1-2 months, about 6 weeks, about 2-3 months, about 3-4 months, about 4-5 months, about 5-6 months, about 6-7 months, about 7-8 months, about 8-9 months, about 9-10 months, about 10-11 months, about 11-12 months, etc.

A pharmaceutical composition may be in the form of a tablet or capsule that has: (a) the acid inhibitor; and/or (b) a buffering agent; and (c) the non-steroidal anti-inflammatory drug (NSAID) present in an amount effective to reduce or eliminate pain or inflammation in a patient upon administration of one or more of said unit dosage forms. The components of the pharmaceutical composition may be in an immediate or extended release form individually or in total.

The term "unit dosage form" as used herein refers to a single entity for drug administration. For example, a single tablet or capsule combining both an acid inhibitor and an NSAID would be a unit dosage form. A "unit dosage form" (or "unit dose form") may also be referred to as a "fixed dosage form" (or "fixed dose form") or "fixed dosage combination" (or "fixed dose combination") and are otherwise interchangeable. In one embodiment, the unit dosage form is a multilayer tablet.

In another embodiment, the unit dosage form is suitable for oral administration to a patient. In yet another embodiment, the unit dosage form is a tablet. In still another embodiment, the unit dosage form is a multilayer tablet comprising a single core and one or more layers outside of the core.

Some dosage forms may comprise a first layer comprising meloxicam, an SBEβCD, and a bicarbonate; and a second layer comprising a second therapeutically active agent and a bicarbonate.

The first layer may contain, for example, any amount of meloxicam in one of the ranges recited above. For example, all of the meloxicam in the dosage form may be present in the first layer. The second layer may contain all of the second therapeutically active agent, such that any amount in the ranges recited above with respect to the second therapeutically active agent may apply to the second layer.

In some embodiments, the first layer contains about 10-200 mg, about 50-150 mg, about 50-100 mg, about 70-120 mg, about 90-140 mg, or about 100 mg of the bicarbonate, such as sodium bicarbonate, or any amount of the bicarbonate in a range bounded by any of these values.

In some embodiments, the second layer contains about 100-500 mg, about 200-500 mg, about 300-500 mg, about 350-450 mg, about 380-420 mg, or about 400 mg of the bicarbonate, such as sodium bicarbonate, or any amount of the bicarbonate in a range bounded by any of these values.

In some embodiments, the pharmaceutical composition may have an effective amount of meloxicam, a cyclodextrin, and a carbonate or bicarbonate to increase bioavailability of meloxicam. In other embodiments, the pharmaceutical composition may have an effective amount of meloxicam, sulfobutylether-β-cyclodextrin (SBEβCD), and sodium bicarbonate to increase bioavailability of meloxicam or reduce the $T_{max}$ of meloxicam.

Some oral dosage forms may have enteric coatings or film coatings. In some embodiments, a dosage form may comprise a tablet or a capsule having an enteric coating. In some embodiments, a dosage form may comprise a tablet or a capsule having a film coating.

An embodiment of the present disclosure is directed to a pharmaceutical composition in unit dosage form suitable for administration to a patient, comprising:
  (a) esomeprazole, which may or may not be surrounded by an enteric coating;
  (b) sodium or potassium bicarbonate and/or sodium or potassium carbonate; and
  (c) meloxicam, which may or may not be formulated with a cyclodextrin, and which may or may not be surrounded by an enteric coating An embodiment of the present disclosure is directed to a pharmaceutical composition in unit dosage form suitable for administration to a patient for treat a disease, a condition, or disorder, such as migraine, comprising:
  (1) an inclusion complex of a meloxicam and a sulfobutyl ether β-cyclodextrin (SBEβCD);
  (2) a bicarbonate, such as sodium bicarbonate or potassium bicarbonate; and
  (3) a triptan, such as rizatriptan.

In certain embodiments, the pharmaceutical composition results in faster release or dissolution of the meloxicam from the dosage form as compared to a dosage form containing meloxicam but not containing the acid inhibitor, or not containing the buffering agent.

A dosage form comprising a combination of rizatriptan and meloxicam (a "subject combination") may be used to treat migraine. The subject combination may be used for the acute treatment of migraine. The subject combination may provide substantially greater and more sustained migraine pain relief compared to rizatriptan, meloxicam, or placebo. The subject combination may provide rapid relief of migraine pain. The subject combination may significantly reduce the use of rescue medication compared to rizatriptan, meloxicam and placebo. The migraine patients being treated with a combination of rizatriptan and meloxicam described herein may have a history of inadequate response to prior acute treatments. The migraine patients being treated with a combination of rizatriptan and meloxicam described herein may have allodynia, such as cutaneous allodynia. The migraine patients being treated with a combination of rizatriptan and meloxicam described herein may have severe pain intensity. The migraine patients being treated with a combination of rizatriptan and meloxicam described herein may have obesity. The migraine patients being treated with a combination of rizatriptan and meloxicam described herein may have morning migraine. The migraine patients being treated with a combination of rizatriptan and meloxicam described herein may have a total mean score of the Migraine Treatment Optimization Questionnaire (mTOQ-4) of less than 7, such as 1-2, 2-3, 3-4, 4-5, 5-6, or 6-7. The migraine patients being treated with a combination of rizatriptan and meloxicam described herein may have allodynia, such as cutaneous allodynia, severe pain intensity, obesity, morning migraine, a total mean score of the mTOQ-4 of less than 7, and a history of inadequate response to prior acute treatments. A dosage form comprising a combination of rizatriptan and meloxicam described herein is safe and well tolerated in the migraine patients being treated.

A dosage form comprising a combination of rizatriptan and meloxicam described herein may provide rapid relief of migraine pain in less than 15 minutes, about 15 minutes, less than 30 minutes, 15-30 minutes, less than 1 hour, 0.5-0.75 hour, or 0.75-1 hour post dose. The combination of rizatriptan and meloxicam described herein may provide relief of migraine pain that is numerically greater than rizatriptan at less than 15 minutes, about 5 minutes, about 5-10 minutes, about 10-15 minutes, about 15 minutes, about 15-30 minutes, about 30-45 minutes, about 45-60 minutes, about 1-1.5 hours, about 1.5-2 hours, about 2-2.5 hours, about 2.5-3 hours, about 3-3.5 hours, about 3.5-4 hours, about 4-5 hours, about 5-6 hours, about 6-8 hours, about 8-10 hours, about 10-12 hours, about 12-24 hours, about 24-48 hours, or longer, post dose. The percentage of migraine patients reporting pain relief with the treatment of a combination of rizatriptan and meloxicam described herein may be 1-100%, 3-100%, 4-100%, 5-100%, 3-5%, 5-10%, 10-20%, 20-30%, 30-40%, 40-50%, 50-60%, 60-70%, 70-80%, 80-90%, 90-95%, or 95-100%.

The migraine patients receiving a dosage form comprising a combination of rizatriptan and meloxicam described herein ("subject combination") may achieve pain freedom at less than 2 hours, about 2 hours, about 2-3 hours, about 3-4 hours, about 4-6 hours, about 6-8 hours, about 8-10 hours, about 10-12 hours, about 12-16 hours, about 16-20 hours, about 20-24 hours, about 24-30 hours, about 30-36 hours, about 36-40 hours, about 40-44 hours, about 44-48 hours, or longer post dose.

The percentage of migraine patients achieving pain freedom increases over time after receiving a dose of a combination of rizatriptan and meloxicam described herein. For example, at 2 h post dose, the percentage of migraine patients achieving pain freedom may be about 15-25%, about 15-20%, about 20%, about 20-25%. At 4 h post dose, the percentage of migraine patients achieving pain freedom may be about 30-50%, about 30-40%, about 40%, about 40-45%, about 45-47%, about 47-50%. At 12 h post dose, the percentage of migraine patients achieving pain freedom may be about 45-70%, about 45-50%, about 50-55%, about 55-60%, about 56-57%, about 60-65%, about 65-70%. At 16 h post dose, the percentage of migraine patients achieving pain freedom may be about 45-70%, about 45-50%, about 50-55%, about 55-60%, about 58-59%, about 60-65%, about 65-70%. The combination of rizatriptan and meloxicam described herein may provide significant improvement over rizatriptan in pain freedom in the migraine patients. There may be about 2-10%, 2-3%, 3-5%, 5-7%, 6-7%, 7-8%, 8-9%, or 9-10% more migraine patients receiving the combination of rizatriptan and meloxicam described herein achieving pain freedom than the migraine patients receiving rizatriptan at 2-16 hours post dose with an improvement of about 10-25%, 10-15%, 14-15%, 15-16%, 16-17%, 17-18%, 18-19%, 19-20%, 20-21%, or 21-25%. For example, at 4 hours post dose, if about 40% migraine patients receiving the subject combination achieve pain freedom, while 33% migraine patients receiving rizatriptan achieve pain freedom, then the improvement of the subject combination is about 21% [((40-33)/33)×100%]. The improvement with the subject combination over meloxicam may be bigger than over rizatriptan in migraine patients achieving pain freedom. For example, The improvement with the subject combination over meloxicam in migraine patients achieving pain freedom may be about 25-75%, 25-30%, 27-28%, 28-29%, 30-40%, 40-50%, 50-60%, 55-50%, 60-70%, 65-75%, or 70-75% at 2-16 hours post dose.

There may be at least 50%, at least 60%, at least 70%, at least 80%, about 70-80%, about 80-90%, about 90-95%, about 80% of migraine patients receiving the combination of rizatriptan and meloxicam described herein ("subject combination") achieving pain freedom at 2 hours may maintain it through 24 hours post dose. The increase of the number of migraine patients (or improvement) achieving sustained pain freedom from 2-24 hours post dose of the subject combination may be about 35-55%, about 35-40%, about 40-45%, about 45-50%, or about 50-55% as compared to administering rizatriptan. The increase of the number of migraine patients (or improvement) achieving sustained pain freedom from 2-24 hours post dose of the subject combination may be about 100-165%, about 100-110%, about 110-120%, about 120-130%, about 130-140%, about 140-150%, about 150-160%, or about 160-165% as compared to administering meloxicam.

The increase of the number of migraine patients (or improvement) achieving sustained pain relief from 2-24 hours post dose of the subject combination may be about 15-30%, about 15-20%, about 20-25%, about 25-30%, about 20-22%, or about 21% as compared to administering rizatriptan. The increase of the number of migraine patients (or improvement) achieving sustained pain relief from 2-24 hours post dose of the subject combination may be about 20-35%, about 20-25%, about 25-30%, about 30-35%, about 25-26%, about 26-27%, about 27-28%, about 28-30%, or about 27% as compared to administering meloxicam.

There may be at least 50%, at least 60%, at least 70%, at least 80%, about 70-80%, about 80-90%, about 90-95%, or about 77% of migraine patients receiving the combination of rizatriptan and meloxicam described herein ("subject combination") achieving pain freedom at 2 hours may maintain it through 48 hours post dose. The increase of the number of migraine patients (or improvement) achieving sustained pain freedom from 2-48 hours post dose of the subject combination may be about 60-90%, about 60-70%, about 70-75%, about 75-80%, about 80-90%, or about 75% as compared to administering rizatriptan. The increase of the number of migraine patients (or improvement) achieving sustained pain freedom from 2-48 hours post dose of the subject combination may be about 70-110%, about 70-80%, about 80-90%, about 90-100%, about 100-110%, or about 90% as compared to administering meloxicam.

The increase of the number of migraine patients (or improvement) achieving sustained pain relief from 2-48 hours post dose of the subject combination may be about 20-35%, about 20-25%, about 25-30%, about 30-35%, about 25-26%, about 26-27%, about 27-28%, about 28-20%, or about 27% as compared to administering rizatriptan. The increase of the number of migraine patients (or improvement) achieving sustained pain relief from 2-48 hours post dose of the subject combination may be about 15-30%, about 15-20%, about 20-25%, about 25-30%, about 20-21%, about 21-22%, about 22-23%, about 23-24%, about 24-25%, or about 23% as compared to administering meloxicam.

There may be at least 50%, at least 60%, at least 70%, about 60-65%, about 65-70%, about 70-75%, about 75-80%, about 80-85%, about 85-90%, about 90-95%, or about 77% of migraine patients receiving the combination of rizatriptan and meloxicam described herein ("subject combination") may not require rescue medication. The decrease of the number of migraine patients who took rescue medication through 24 hours post dose of the subject combination may be about 35-60%, about 35-40%, about 40-45%, about 45-50%, about 50-55%, about 55-60%, about 47-48%, or about 47% as compared to administering placebo. The decrease of the number of migraine patients who took rescue medication through 24 hours post dose of the subject combination may be about 25-45%, about 25-30%, about 30-35%, about 35-40%, about 40-45%, about 34-36%, or about 35% as compared to administering meloxicam. The decrease of the number of migraine patients who took rescue medication through 24 hours post dose of the subject combination may be about 25-40%, about 25-30%, about 30-35%, about 35-40%, about 33-35%, or about 34% as compared to administering rizatriptan. In some embodiments, the migraine patient does not take rescue medication in the 24 hours after the subject combination is administered.

The following embodiments are contemplated:

Embodiment 1

An inclusion complex of meloxicam in a cyclodextrin.

Embodiment 2

A dosage form comprising: 1) the inclusion complex of embodiment 1, or 2) meloxicam and a carbonate or a bicarbonate.

Embodiment 3

The dosage form of embodiment 2 comprising the inclusion complex, wherein the cyclodextrin comprises substituted β-cyclodextrin.

Embodiment 4

The dosage form of embodiment 3, wherein the substituted β-cyclodextrin is a sulfobutyl ether β-cyclodextrin (SBEβCD) or hydroxypropyl β-cyclodextrin (HPβCD).

Embodiment 5

The dosage form of embodiment 4, wherein the cyclodextrin is the SBEβCD.

Embodiment 6

The dosage form of embodiment 5, wherein the SBEβCD has about 6 to about 7 sulfobutyl ether groups for each molecule of β-cyclodextrin.

Embodiment 7

The dosage form of embodiment 6, wherein the meloxicam and the SBEβCD have a molar ratio of about 0.8 to about 1.2.

Embodiment 8

The dosage form of embodiment 6, wherein the meloxicam and the SBEβCD have a molar ratio of about 1.

Embodiment 9

The dosage form of embodiment 2, 3, 4, 5, 6, 7, or 8, comprising a bicarbonate.

Embodiment 10

The dosage form of embodiment 9, wherein the bicarbonate comprises sodium bicarbonate.

Embodiment 11

The dosage form of embodiment 2, 3, 4, 5, 6, 7, 8, 9, or 10, which is an oral dosage form.

Embodiment 12

The dosage form of embodiment 2, 3, 4, 5, 6, 9, 10, or 11, wherein about 50 mg to about 200 mg of SBEβCD is present in the dosage form.

Embodiment 13

The dosage form of embodiment 2, 3, 4, 5, 6, 7, 8, 9, 10, 11, or 12, wherein the carbonate or bicarbonate is present in an amount in a range of about 400 mg to about 600 mg.

Embodiment 14

The dosage form of embodiment 2, 3, 4, 5, 6, 7, 8, 9, 10, 11, 12, or 13, wherein the $T_{max}$ of meloxicam is decreased as compared to a dosage form not having a carbonate, a bicarbonate, or a cyclodextrin.

Embodiment 15

The method of embodiment 14, wherein the $T_{max}$ of meloxicam is achieved in the patient at a time in a range of about 10 minutes to about 180 minutes after administration.

Embodiment 16

The dosage form of embodiment 2, 3, 4, 5, 6, 7, 8, 9, 10, 11, 12, 13, 14, or 15, having an oral bioavailability of meloxicam that is higher than a dosage form not having a carbonate, a bicarbonate, or a cyclodextrin.

Embodiment 17

The dosage form of embodiment 2, 3, 4, 5, 6, 7, 8, 9, 10, 11, 12, 13, 14, 15, 16, 17, 18, 19, or 20, further comprising an acid inhibitor.

Embodiment 18

The dosage form of embodiment 17, wherein the acid inhibitor is a proton pump inhibitor.

Embodiment 19

The dosage form of embodiment 18, wherein the proton pump inhibitor is esomeprazole.

Embodiment 20

The dosage form of embodiment 19, wherein about 30 mg to about 50 mg of esomeprazole is present in the dosage form.

Embodiment 21

A method of administering meloxicam orally, comprising orally administering a dosage form of embodiment 2, 3, 4, 5, 6, 7, 8, 9, 10, 11, 12, 13, 14, 15, 16, 17, 18, 19, or 20 to a patient in need of treatment.

Embodiment 22

The method of embodiment 21, wherein the dosage form is administered to treat pain.

Embodiment 23

The method of embodiment 21, wherein the dosage form is administered to treat inflammatory pain.

Embodiment 24

The method of embodiment 21, wherein the dosage form is administered to treat osteoarthritis, rheumatoid arthritis, or juvenile rheumatoid arthritis.

Embodiment 25

A method of administering meloxicam intravenously, comprising intravenously administering a dosage form of embodiment 2, 3, 4, 5, 6, 7, 8, 9, 10, 12, 13, 14, or 15, to a patient in need of treatment.

Embodiment 26

The method of embodiment 21, wherein the dosage form is administered to treat migraine.

Embodiment 27

A dosage form comprising: 1) the inclusion complex of meloxicam in a cyclodextrin, 2) a bicarbonate, and 3) a triptan.

Embodiment 28

The dosage form of embodiment 27, wherein the triptan is rizatriptan.

Embodiment 29

The dosage form of embodiment 27, wherein the bicarbonate comprises sodium bicarbonate.

Embodiment 30

The dosage form of embodiment 27, wherein the cyclodextrin is a sulfobutyl ether β-cyclodextrin (SBEβCD).

Embodiment 31

The dosage form of embodiment 30, wherein the SBEβCD has about 6 to about 7 sulfobutyl ether groups for each molecule of β-cyclodextrin.

Embodiment 32

The dosage form of embodiment 30, wherein the meloxicam and the SBEβCD have a molar ratio of about 0.8 to about 1.2.

Embodiment 33

The dosage form of embodiment 32, wherein the meloxicam and the SBEβCD have a molar ratio of about 1.

Embodiment 34

The dosage form of embodiment 27, 28, 29, 30, 31, 32, or 33, which is an oral dosage form.

Embodiment 35

The dosage form of embodiment 27, 28, 29, 30, 31, 32, 33, or 34, wherein about 50 mg to about 200 mg of SBEβCD is present in the dosage form.

Embodiment 36

The dosage form of embodiment 27, 28, 29, 30, 31, 32, 33, 34, or 35, wherein the bicarbonate is present in an amount of about 400 mg to about 1000 mg.

Embodiment 37

A method of treating migraine, comprising administering a dosage form comprising meloxicam, at least 400 mg of a bicarbonate, and a rizatriptan to a human being suffering from migraine; wherein the $T_{max}$ of rizatriptan in the dosage form is shorter than that in a reference dosage form comprising a) same amount of rizatriptan; 2) no meloxicam; and c) no bicarbonate.

Embodiment 38

A method of treating migraine, comprising administering meloxicam and about 8 mg to about 13 mg of rizatriptan, based upon the weight of the rizatriptan in the free base form, to a human being who is suffering from an acute attack of migraine pain or migraine aura, wherein the meloxicam and the rizatriptan are administered within about 30 minutes of one another, wherein administering the meloxicam to the human being results in a $T_{max}$ of meloxicam of 110 minutes or less, and an $AUC_{0-24}$ of meloxicam of about 30 μg·hr/mL to about 50 μg·hr/mL.

Embodiment 39

A pharmaceutical dosage form comprising: 1) about 0.028 mmol to about 0.085 mmol of meloxicam in a free acid or a salt form, 2) about 0.019 mmol to about 0.056 mmol of rizatriptan in a free base or a salt form, 3) about 100 mg to about 175 mg of a sulfobutylether-β-cyclodextrin (SBEβCD), and 4) about 400 mg to about 600 mg of sodium bicarbonate.

Embodiment 40

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan.

Embodiment 41

The method of embodiment 40, wherein the human migraine patient experiences relief of the migraine pain as a result of orally administering the dosage form to the migraine patient.

Embodiment 42

The method of embodiment 40 or 41, wherein the human migraine patient is free of migraine pain two hours after the dosage form is orally administered to the human migraine patient.

Embodiment 43

The method of embodiment 40, 41, or 42, wherein the migraine patient experiences a reduction in nausea as a result of orally administering the dosage form to the migraine patient.

Embodiment 44

The method of embodiment 40, 41, 42, or 43, wherein the human migraine patient is free of nausea two hours after the dosage form is orally administered to the human migraine patient.

Embodiment 45

The method of embodiment 40, 41, 42, 43, or 44, wherein the migraine patient experiences a reduction in photophobia as a result of orally administering the dosage form to the migraine patient.

Embodiment 46

The method of embodiment 40, 41, 42, 43, 44, or 45, wherein the human migraine patient is free of photophobia two hours after the dosage form is orally administered to the human migraine patient.

Embodiment 47

The method of embodiment 40, 41, 42, 43, 44, 45, or 46, wherein the migraine patient experiences a reduction in phonophobia as a result of orally administering the dosage form to the migraine patient.

Embodiment 48

The method of embodiment 40, 41, 42, 43, 44, 45, 46, or 47, wherein the human migraine patient is free of phonophobia two hours after the dosage form is orally administered to the human migraine patient.

Embodiment 49

The method of embodiment 40, 41, 42, 43, 44, 45, 46, 47, or 48, wherein the dosage form contains 400 mg to 600 mg of the bicarbonate.

Embodiment 50

The method of embodiment 40, 41, 42, 43, 44, 45, 46, 47, 48, or 49, wherein the dosage form contains about 5 mg to about 50 mg of meloxicam.

Embodiment 51

The method of embodiment 40, 41, 42, 43, 44, 45, 46, 47, 48, 49, or 50, wherein the dosage form contains about 50 mg to about 200 mg of the SBEβCD.

Embodiment 52

The method of embodiment 40, 41, 42, 43, 44, 45, 46, 47, 48, 49, 50, or 51, wherein the dosage form is a solid oral dosage form having a shorter Tmax of meloxicam in the human being than a reference dosage form that: 1) contains the same amount of meloxicam, 2) does not contain an SBEβCD, and 3) does not contain a bicarbonate.

Embodiment 53

The method of embodiment 40, 41, 42, 43, 44, 45, 46, 47, 48, 49, 50, 51, or 52, wherein about 1 mg to about 50 mg of the rizatriptan is present in the oral dosage form based upon the weight of the rizatriptan in the free base form.

Embodiment 54

The method of embodiment 53, wherein the rizatriptan is present in a salt form in an amount that is a molar equivalent of about 10 mg of the rizatriptan in the free base form.

Embodiment 55

The method of embodiment 53 or 54, wherein the rizatriptan is present as rizatriptan benzoate.

Embodiment 56

The method of embodiment 40, 41, 42, 43, 44, 45, 46, 47, 48, 49, 50, 51, 52, 53, 54, or 55, wherein the oral dosage form contains about 10 mg to about 30 mg of meloxicam.

Embodiment 57

The method of embodiment 56, wherein the oral dosage form contains about 20 mg of meloxicam.

Embodiment 58

The method of embodiment 56, wherein the oral dosage form contains about 15 mg of meloxicam.

Embodiment 59

The method of embodiment 40, 41, 42, 43, 44, 45, 46, 47, 48, 49, 50, 51, 52, 53, 54, 55, 56, 57, or 58, wherein the SBEβCD has about 6 to about 7 sulfobutyl ether groups for each molecule of β-cyclodextrin.

Embodiment 60

The method of embodiment 40, 41, 42, 43, 44, 45, 46, 47, 48, 49, 50, 51, 52, 53, 54, 55, 56, 57, 58, or 59, wherein the oral dosage form contains about 50 mg to about 150 mg of the SBEβCD.

Embodiment 61

The method of embodiment 60, wherein the oral dosage form contains about 100 mg of the SBEβCD.

Embodiment 62

The method of embodiment 40, 41, 42, 43, 44, 45, 46, 47, 48, 49, 50, 51, 52, 53, 54, 55, 56, 57, 58, 59, 60, or 61, wherein the molar ratio of the SBEβCD to meloxicam is about 0.5 to about 2.

Embodiment 63

The method of embodiment 62, wherein the molar ratio of the SBEβCD to meloxicam is about 0.8 to about 1.2.

Embodiment 64

The method of embodiment 62, wherein the molar ratio of the SBEβCD to meloxicam is about 1.

Embodiment 65

The method of embodiment 40, 41, 42, 43, 44, 45, 46, 47, 48, 49, 50, 51, 52, 53, 54, 55, 56, 57, 58, 59, 60, 61, 62, 63, or 64, wherein the oral dosage form contains about 10 mg to about 40 mg of meloxicam, and about 5 mg to about 50 mg of rizatriptan.

Embodiment 66

The method of embodiment 40, 41, 42, 43, 44, 45, 46, 47, 48, 49, 50, 51, 52, 53, 54, 55, 56, 57, 58, 59, 60, 61, 62, 63, 64, or 65, wherein the oral dosage form contains SBEβCD that is in a weight ratio to rizatriptan that is within a range of about 1 to about 100.

Embodiment 67

The method of embodiment 66, wherein the oral dosage form contains SBEβCD that is in a weight ratio to rizatriptan that is about 10.

Embodiment 68

The method of embodiment 40, 41, 42, 43, 44, 45, 46, 47, 48, 49, 50, 51, 52, 53, 54, 55, 56, 57, 58, 59, 60, 61, 62, 63, 64, 65, 66, or 67, wherein the bicarbonate comprises sodium bicarbonate.

Embodiment 69

The method of embodiment 68, wherein the oral dosage form contains 500 mg of sodium bicarbonate.

Embodiment 70

The method of embodiment 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein the oral dosage form has been shown to have a median Tmax of meloxicam that is less than about 90 minutes in fasted human subjects.

Embodiment 71

The method of embodiment 70, wherein the oral dosage form has been shown to have a median Tmax of meloxicam that is less than about 2 hours in fasted human subjects.

Embodiment 72

The method of embodiment 52, 53, 54, 55, 56, 57, 58, 59, 60, 61, 62, 63, 64, 65, 66, 67, 68, 69, 70, or 71, wherein the oral dosage form has been shown to have faster time to therapeutic plasma concentration in the human being as compared to the reference dosage form.

Embodiment 73

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan, wherein the human migraine patient experiences relief of the migraine pain as a result of orally administering the dosage form to the migraine patient.

Embodiment 74

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan, wherein the human migraine patient is free of migraine pain two hours after the dosage form is orally administered to the human migraine patient.

Embodiment 75

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan, wherein the migraine patient experiences a reduction in nausea as a result of orally administering the dosage form to the migraine patient.

Embodiment 76

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan, wherein the human migraine patient is free of nausea two hours after the dosage form is orally administered to the human migraine patient.

Embodiment 77

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan, wherein the migraine patient experiences a reduction in photophobia as a result of orally administering the dosage form to the migraine patient.

Embodiment 78

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan, wherein the human migraine patient is free of photophobia two hours after the dosage form is orally administered to the human migraine patient.

Embodiment 79

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan, wherein the migraine patient experiences a reduction in phonophobia as a result of orally administering the dosage form to the migraine patient.

Embodiment 80

A method of treating migraine comprising: selecting a human migraine patient with a history of inadequate response to prior migraine treatments, and orally administering a dosage form to the migraine patient, wherein the dosage form comprises a combination of: 1) meloxicam (optionally in a complex with a sulfobutyl ether β-cyclodextrin (SBEβCD)), 2) a bicarbonate, and 3) a rizatriptan, wherein the human migraine patient is free of phonophobia two hours after the dosage form is orally administered to the human migraine patient.

Embodiment 81

A method of more rapidly improving migraine pain relief associated with rizatriptan therapy, comprising: orally administering to a human being in need thereof, a combination of: 1) a complex of a meloxicam and a sulfobutylether-β-cyclodextrin, 2) a bicarbonate, and 3) a rizatriptan, wherein one hour after the combination is administered, the human being experiences a greater reduction in migraine pain than the human being would experience one hour after the same amount of the rizatriptan is administered alone.

Embodiment 82

A method of relieving migraine pain, comprising: orally administering to a human being in need thereof, a combination of: 1) a complex of meloxicam and a sulfobutylether-β-cyclodextrin, 2) a bicarbonate, and 3) a rizatriptan, wherein the combination is orally administered when the human being is suffering from moderate to severe migraine pain of an acute migraine, wherein two hours after the combination is administered, the human being experiences a greater reduction in the human being's most bothersome symptom than the human being would experience two hours after the same amount of the rizatriptan is administered alone.

Embodiment 83

A method of relieving migraine pain, comprising: orally administering to a human being in need thereof, a combination of: 1) a complex of meloxicam and a sulfobutylether-β-cyclodextrin, 2) a bicarbonate, and 3) a rizatriptan, wherein the combination is orally administered when the human being is suffering from moderate to severe migraine pain of an acute migraine, wherein the human being suffers from migraine with cutaneous allodynia, wherein two hours after the combination is orally administered, the human being experiences a greater reduction in the migraine pain than the human being would experience two hours after the same amount of the meloxicam is administered alone.

Embodiment 84

A method of relieving migraine pain, comprising: orally administering to a human being in need thereof, a combination of: 1) a complex of meloxicam and a sulfobutylether-β-cyclodextrin, 2) a bicarbonate, and 3) a rizatriptan, wherein the combination is orally administered when the human being is suffering from severe migraine pain of an acute migraine, wherein two hours after the combination is orally administered, the human being experiences a greater reduction in the migraine pain than the human being would experience two hours after the same amount of the meloxicam is administered alone.

Embodiment 85

A method of relieving migraine pain, comprising: orally administering to a human being in need thereof, a combination of: 1) a complex of meloxicam and a sulfobutylether-β-cyclodextrin, 2) a bicarbonate, and 3) a rizatriptan, wherein the combination is orally administered when the human being is suffering from moderate to severe migraine pain of an acute migraine, wherein the human being is obese, wherein two hours after the combination is orally administered, the human being experiences a greater reduction in the migraine pain than the human being would experience two hours after the same amount of the meloxicam is administered alone.

Embodiment 86

A method of relieving migraine pain, comprising: orally administering to a human being in need thereof, a combination of: 1) a complex of meloxicam and a sulfobutylether-β-cyclodextrin, 2) a bicarbonate, and 3) a rizatriptan, wherein the combination is orally administered when the human being is suffering from moderate to severe migraine pain of an acute migraine, wherein the human being has morning migraine, wherein two hours after the combination is orally administered, the human being experiences a greater reduction in the migraine pain than the human being would experience two hours after the same amount of the meloxicam is administered alone.

Embodiment 87

A method of relieving migraine pain, comprising: orally administering to a human being in need thereof, a combination of: 1) a complex of meloxicam and a sulfobutylether-β-cyclodextrin, 2) a bicarbonate, and 3) a rizatriptan, wherein the combination is orally administered when the human being is suffering from moderate to severe migraine pain of an acute migraine, wherein at least one year prior to orally administering the combination to the human being, the human being has been diagnosed as having migraine with aura or migraine without aura as defined by the International Classification of Headache Disorders, third edition (ICHD-3), wherein two hours after the combination is orally administered, the human being experiences a greater reduction in the migraine pain than the human being would experience two hours after the same amount of the meloxicam is administered alone.

Embodiment 88

A method of treating migraine comprising: orally administering a dosage form to a human migraine patient, wherein the oral dosage form comprises a combination of: 1) a complex of a meloxicam with a sulfobutyl ether β-cyclodextrin (SBEβCD), 2) a bicarbonate, and 3) a rizatriptan, wherein the human migraine patient suffers from migraine with cutaneous allodynia at the time the dosage form is administered, wherein the human migraine patient is free of cutaneous allodynia two hours after the dosage form is orally administered to the human migraine patient.

Embodiment 89

The method of embodiment 81, 82, 83, 84, 85, 86, 87, or 88, wherein the migraine pain is accompanied by disturbed vision.

Embodiment 90

The method of embodiment 89, wherein the human being achieves absence of the disturbed vision at 2 hours after the combination is orally administered.

Example 1

The effect of varying amounts of potassium carbonate ($K_2CO_3$) and sodium bicarbonate ($NaHCO_3$) on the pH of acidic media was tested. The acidic media was chosen to simulate gastric conditions. $K_2CO_3$ or $NaHCO_3$ was added to 50 mL of a 0.01 N HCl solution (pH 2). The pH of the solution was measured after addition of the $K_2CO_3$ or $NaHCO_3$. Deionized water (240 mL) was then added to the mixture and pH was measured again. The results are shown in Tables 1-4.

TABLE 1

Results with $K_2CO_3$ (0.01N HCl)

| $K_2CO_3$ (mg) | pH |
|---|---|
| 25 | 2.84 |
| 35 | 6.29 |
| 45 | 8.05 |
| 50 | 8.29 |
| 100 | 9.43 |
| 200 | 10.14 |
| 300 | 10.39 |
| 400 | 10.55 |
| 450 | 10.58 |

TABLE 2

Results with $K_2CO_3$ (0.01N HCl + Water)

| $K_2CO_3$ (mg) | pH |
|---|---|
| 200 | 10.27 |
| 300 | 10.46 |
| 400 | 10.57 |
| 450 | 10.63 |

TABLE 3

Results with $NaHCO_3$ (0.01N HCl)

| $NaHCO_3$ (mg) | pH |
|---|---|
| 200 | 5.28 |
| 300 | 5.90 |
| 400 | 6.44 |
| 450 | 6.86 |
| 500 | 8.23 |
| 750 | 8.30 |
| 1000 | 8.36 |

TABLE 4

Results with $NaHCO_3$ (0.01N HCl + Water)

| $NaHCO_3$ (mg) | pH |
|---|---|
| 200 | 5.41 |
| 300 | 5.89 |
| 400 | 6.11 |
| 450 | 6.46 |
| 500 | 8.33 |
| 750 | 8.54 |
| 1000 | 8.60 |

Example 2

Tablets containing meloxicam and combinations of a sulfobutylether-β-cyclodextrin (SBEβCD) (a cyclodextrin, containing about 6 to about 7 sulfobutyl ether groups for each molecule of β-cyclodextrin), $K_2CO_3$, or $NaHCO_3$ were manufactured and tested for dissolution. Tablets containing meloxicam alone (MOBIC®) were purchased and also tested for dissolution. The tested tablets are listed in Table 5. Meloxicam in the form of meloxicam/SBEβCD inclusion complexes was used in the tablets containing meloxicam and SBEβCD. The inclusion complexes were formed by mixing meloxicam and SBEβCD in an aqueous pH-adjusted solution. The pH of the solution was adjusted using buffering agents. The resulting soluble meloxicam/SBEβCD inclusion complexes were then spray dried. This spray-dried dispersion was used in the manufacture of the tablets containing SBEβCD.

TABLE 5

Tablets

| | |
|---|---|
| Tablet A | 15 mg meloxicam + 25 mg $K_2CO_3$ |
| Tablet B | 15 mg meloxicam + 50 mg $K_2CO_3$ |
| Tablet C | 15 mg meloxicam + 100 mg $K_2CO_3$ |
| Tablet D | 15 mg meloxicam + 150 mg $K_2CO_3$ |
| Tablet E | 15 mg meloxicam + 500 mg $NaHCO_3$ |
| Tablet F | 15 mg meloxicam + 100 mg SBEβCD |
| Tablet G | 15 mg meloxicam + 100 mg SBEβCD + 25 mg $K_2CO_3$ |
| Tablet H | 15 mg meloxicam + 100 mg SBEβCD + 50 mg $K_2CO_3$ |
| Tablet I | 15 mg meloxicam + 100 mg SBEβCD + 100 mg $K_2CO_3$ |
| Tablet J | 15 mg meloxicam + 100 mg SBEβCD + 150 mg $K_2CO_3$ |
| Tablet K | 15 mg meloxicam + 100 mg SBEβCD + 500 mg $NaHCO_3$ |
| Tablet L | 15 mg meloxicam (MOBIC®) |

Dissolution testing in acidic medium (chosen to simulate gastric conditions) was performed by placing the tablets in a 0.01 N HCl solution, at an agitation rate of 75 RPM, and vessel temperature of approximately 37° C. The results are presented in Tables 6 and in FIGS. 1-10. Results at various time points (0, 15, 30, 45, 60, 90, and 120 minutes) are presented as percent (%) of meloxicam dissolved.

TABLE 6

Dissolution Results

| | 0 mins | 15 mins | 30 mins | 45 mins | 60 mins | 90 mins | 120 mins |
|---|---|---|---|---|---|---|---|
| Tablet A | 0% | 23% | 17% | 15% | 13% | 12% | 11% |
| Tablet B | 0% | 27% | 20% | 17% | 16% | 17% | 15% |
| Tablet C | 0% | 31% | 26% | 25% | 24% | 23% | 21% |
| Tablet D | 0% | 30% | 26% | 25% | 24% | 23% | 22% |
| Tablet E | 0% | 50% | 66% | 77% | 84% | 92% | 95% |
| Tablet F | 0% | 26% | 17% | 14% | 12% | 11% | 10% |
| Tablet G | 0% | 48% | 39% | 26% | 20% | 16% | 14% |
| Tablet H | 0% | 44% | 30% | 22% | 17% | 16% | 13% |
| Tablet I | 0% | 32% | 33% | 27% | 21% | 16% | 15% |
| Tablet J | 0% | 26% | 27% | 19% | 15% | 12% | 11% |
| Tablet K | 0% | 85% | 86% | 86% | 86% | 86% | 86% |
| Tablet L | 0% | 2% | 2% | 2% | 2% | 2% | 2% |

Dissolution of meloxicam was greater with the tablets containing various combinations of meloxicam and SBEβCD, $K_2CO_3$, or $NaHCO_3$, as compared to tablets containing meloxicam alone. For example, after 120 minutes, dissolution of meloxicam tablets containing $NaHCO_3$ was 95% as compared to 2% for tablets containing meloxicam alone.

Dissolution of meloxicam increases with increasing amounts of $K_2CO_3$ in the absence of SBEβCD. However, in the presence of SBEβCD, increasing amounts of $K_2CO_3$ did not appear to increase meloxicam dissolution. At the highest dose of potassium carbonate tested, meloxicam dissolution in the presence of SBEβCD was reduced by approximately 50% as compared to meloxicam dissolution in the absence of SBEβCD at 120 minutes.

Dissolution of meloxicam with NaHCO$_3$ was significantly greater than that observed with the highest dose of K$_2$CO$_3$ at 15 minutes (50% versus 30%), and at 120 minutes (92% versus 23%). Meloxicam dissolution in the presence of SBEβCD was also significantly greater with NaHCO$_3$ as compared to the highest dose of K$_2$CO$_3$ at 15 minutes (85% versus 26%), and at 120 minutes (86% versus 12%). NaHCO$_3$ in the presence of SBEβCD increased meloxicam dissolution more at 15 minutes as compared to potassium carbonate, which resulted in a reduction in dissolution.

Example 3

A bilayer tablet containing 1) an inclusion complex of SBEβCD with meloxicam, prepared as described below, and 2) sodium bicarbonate was prepared (SBEβCD-Meloxicam/Bicarbonate). The first layer contained an inclusion complex of 15 mg meloxicam and 100 mg SBEβCD, and 100 mg of sodium bicarbonate. The second layer contained 40 mg of esomeprazole and 400 mg of sodium bicarbonate.

A total of 20 human subjects were randomly assigned in a 1:1 ratio to treatment with the SBEβCD-Meloxicam/Bicarbonate tablets described above or Mobic® tablets (15 mg meloxicam), once daily for 6 days under fasting conditions.

Figure 11:
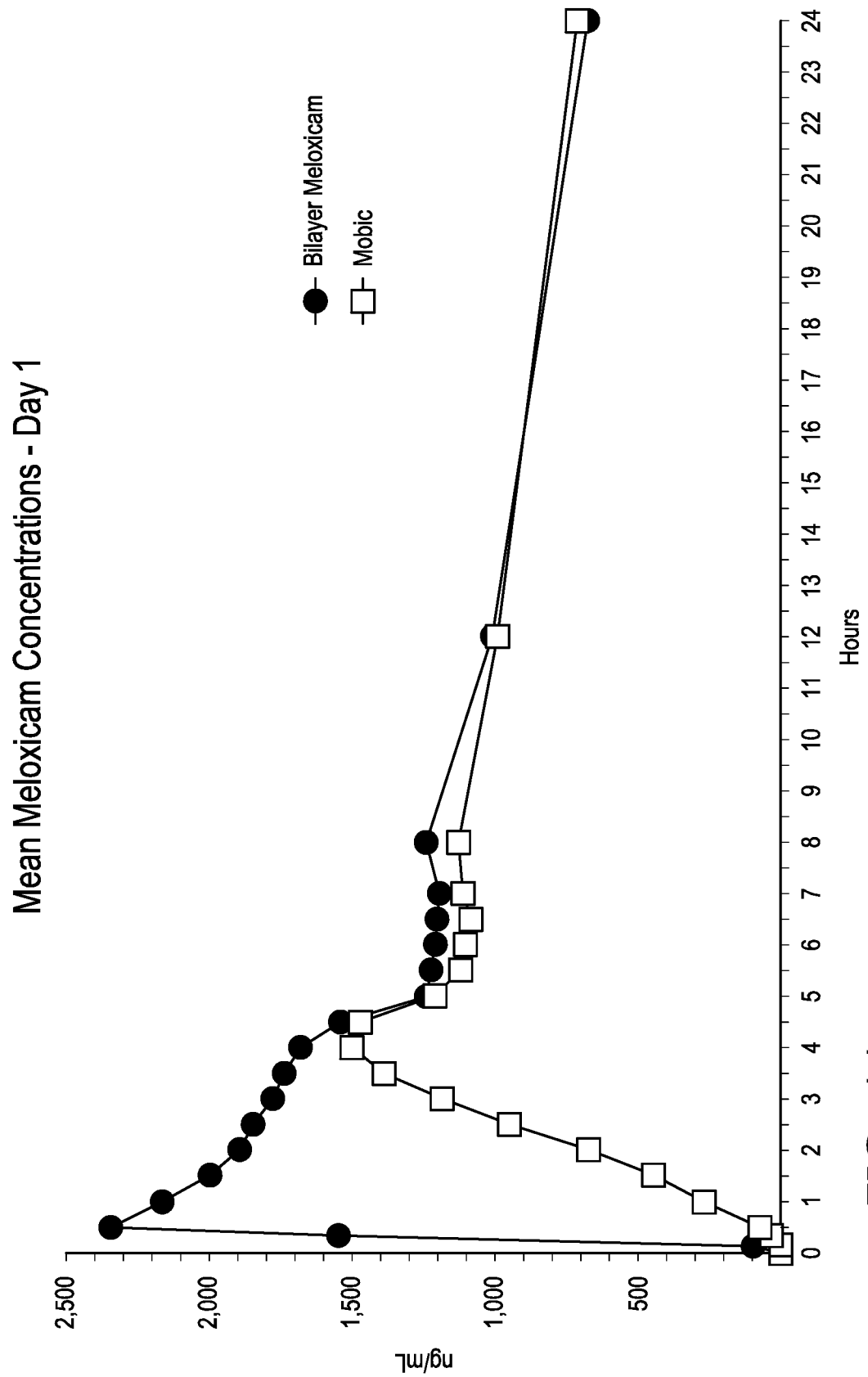
FIG. 11 is a plot of meloxicam plasma concentration at various time points over the first 24 hours for an embodiment of a dosage form described herein and a commercially available meloxicam dosage form.

On the first day of dosing, plasma samples were collected for concentration analysis of meloxicam at several time points. Concentrations of meloxicam were determined using LC-MS/MS. Pharmacokinetic parameters were calculated. The results are depicted in FIG. 11.

The median T$_{max}$ for meloxicam, the trial's primary endpoint, was 9 times faster for the SBEβCD-Meloxicam/Bicarbonate tablets as compared to Mobic® (0.5 hour versus 4.5 hours respectively, p<0.0001).

The SBEβCD-Meloxicam/Bicarbonate tablets also demonstrated higher mean maximum plasma concentration (C$_{max}$) (p=0.0018), faster time to therapeutic plasma concentration (p<0.0001), and faster time to half-maximal plasma concentration (p<0.0001) as compared to Mobic®.

Meloxicam in the form of meloxicam/SBEβD inclusion complexes was used in the tablets containing meloxicam and SBEβCD. The inclusion complexes were formed by mixing meloxicam and SBEβCD in an aqueous pH-adjusted solution. The pH of the solution was adjusted using buffering agents. The resulting soluble meloxicam/SBEβCD inclusion complexes were then spray dried. This spray-dried dispersion was used in the manufacture of the tablets containing SBEβCD.

Example 4

A monolayer tablet containing 1) the inclusion complex of SBEβCD with meloxicam; 2) rizatriptan; and 3) sodium bicarbonate was prepared (SBEβCD-Meloxicam/rizatriptan/Bicarbonate). The monolayer tablet contained 20 mg of meloxicam, 10 mg of rizatriptan, and 500 mg of sodium bicarbonate. The inclusion complex was the same as the inclusion complex of Example 3.

Dissolution testing of the tablets in acidic medium (chosen to simulate gastric conditions) was performed by placing the tablets in a 0.01 N HCl solution, at an agitation rate of 75 RPM, and vessel temperature of approximately 37° C. The results are presented in Table 7. Results at various time points (0, 15, 30, 45, 60, 90, and 120 minutes) are presented as percent (%) of meloxicam, and percent (%) of rizatriptan dissolved.

TABLE 7

Dissolution Results

| Time-point (minutes) | 0 min | 15 min | 30 min | 45 min | 60 min | 90 min | 120 min |
|---|---|---|---|---|---|---|---|
| Rizatriptan | 0% | 89% | 102% | 103% | 103% | 103% | 103% |
| Meloxicam | 0% | 79% | 92% | 93% | 93% | 93% | 94% |

As shown in Table 7, the dissolution results of the tablets in Example 4 are very similar to the dissolution result of Example 3. Therefore, we expected the pharmacokinetic properties, including bioavailability, T$_{max}$ of meloxicam, etc., of the tablets in Example 4 to be similar to those described in Example 3 and FIG. 11. This expectation turned out to be correct, as shown in the examples below.

Example 5

The monolayer tablet of Example 4 was administered to six human subjects. On the first day of dosing, plasma samples were collected for concentration analysis of rizatriptan at several time points. Concentrations of rizatriptan and meloxicam were determined using LC-MS/MS. Pharmacokinetic parameters were calculated. The results for meloxicam were comparable to those reported for the bilayer dosage form of Example 3. The median T$_{max}$ of rizatriptan was 0.75 hours and the mean C$_{max}$ of rizatriptan was 20.710 ng/mL. By comparison, the reported Tmax of the commercial rizatriptan dosage form, Maxalt®, is 1.0-1.5 hours.

Example 6

A Phase 1, randomized, single-dose, parallel-group clinical study was conducted to evaluate the PK, safety and tolerability of 1) a combination of meloxicam (20 mg), rizatriptan (10 mg), SBEβCD, and sodium bicarbonate (meloxicam/rizatriptan), as compared to 2) and Maxalt® (10 mg rizatriptan), in healthy human volunteers after oral administration under fasted conditions. A total of 20 healthy, adult male or female volunteers were randomized in a 1:1 ratio to receive a single dose of meloxicam/rizatriptan, or Maxalt® (10 mg rizatriptan).

Blood samples for PK analysis were collected pre dose and at multiple time points post dose. The pre-specified primary endpoint was T$_{thera}$, the time to reach a therapeutic plasma concentration of meloxicam, defined as the C$_{avg}$ of meloxicam after administration of the highest approved dose (15 mg) of standard meloxicam, which is approximately 1000 ng/mL. PK results for the rizatriptan component of meloxicam/rizatriptan were compared to those for Maxalt® (rizatriptan).

PK results for the meloxicam (20 mg) component of meloxicam/rizatriptan from this trial were compared to PK results for Mobic® (15 mg meloxicam) from Example 3.

Phase 1 Results

Figure 12:
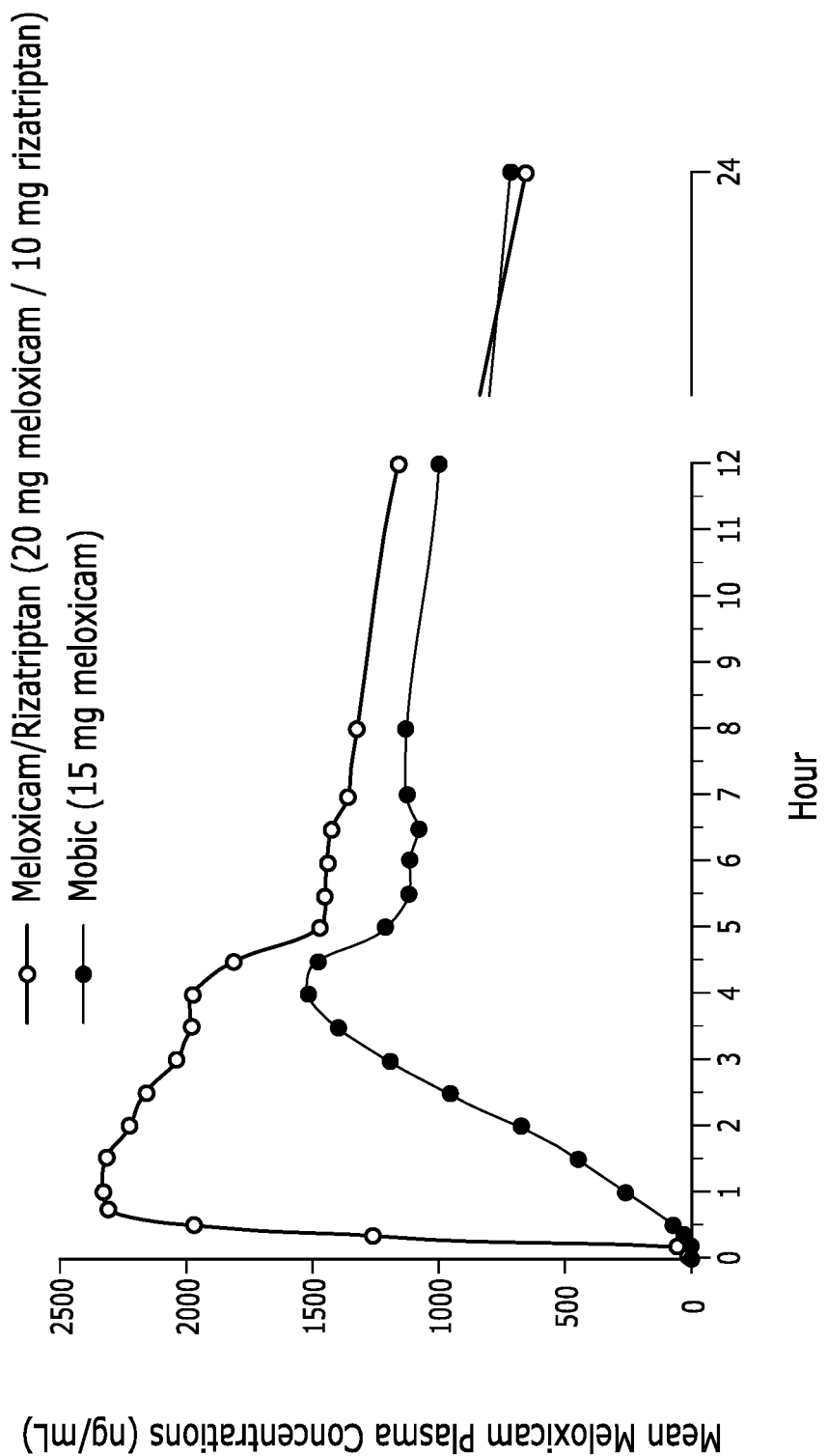
FIG. 12 is a plot of meloxicam plasma concentration at various time points over the first 24 hours for a dosage form of Meloxicam/Rizatriptan described in Example 6 and a commercially available meloxicam dosage form.

Meloxicam was rapidly absorbed after oral administration of meloxicam/rizatriptan (20 mg meloxicam/10 mg rizatriptan), with a median time to therapeutic plasma concentration (T$_{thera}$) of 17 minutes, the primary endpoint (FIG. 12 and Table 8). Median T$_{max}$ was 1 hour compared to 4.5 hours for 15 mg standard meloxicam) (Mobic®. The very short T$_{max}$ suggests the potential for meloxicam/rizatriptan to have rapid onset of action in treating migraine. Mean plasma elimination half-life ($T_{1/2}$) for meloxicam was 18.2 hours after administration of meloxicam/rizatriptan, which compares to 21.5 hours for standard meloxicam. The long elimination half-life suggests the potential for meloxicam/rizatriptan to enhanced and sustained efficacy, and to reduce migraine pain recurrence.

TABLE 8

Meloxicam Pharmacokinetic Parameters for Meloxicam/Rizatriptan

| Statistic | $AUC_{0-inf}$ (ng · hr/mL) | $T_{1/2}$ el (hr) | $C_{max}$ (ng/mL) | $T_{max}$ (hr)$^a$ | $T_{thera}$ (hr)$^a$ |
|---|---|---|---|---|---|
| N | 10 | 10 | 10 | 10 | 10 |
| Geometric Mean | 46,865 | 17.5 | 2,532 | 1.0 | 0.29 |
| SD | 11,965 | 5.25 | 607 | 0.5-2.5 | 0.20-0.61 |

$^a T_{max}$ and $T_{thera}$ present the value as a median or a range.

Figure 13:
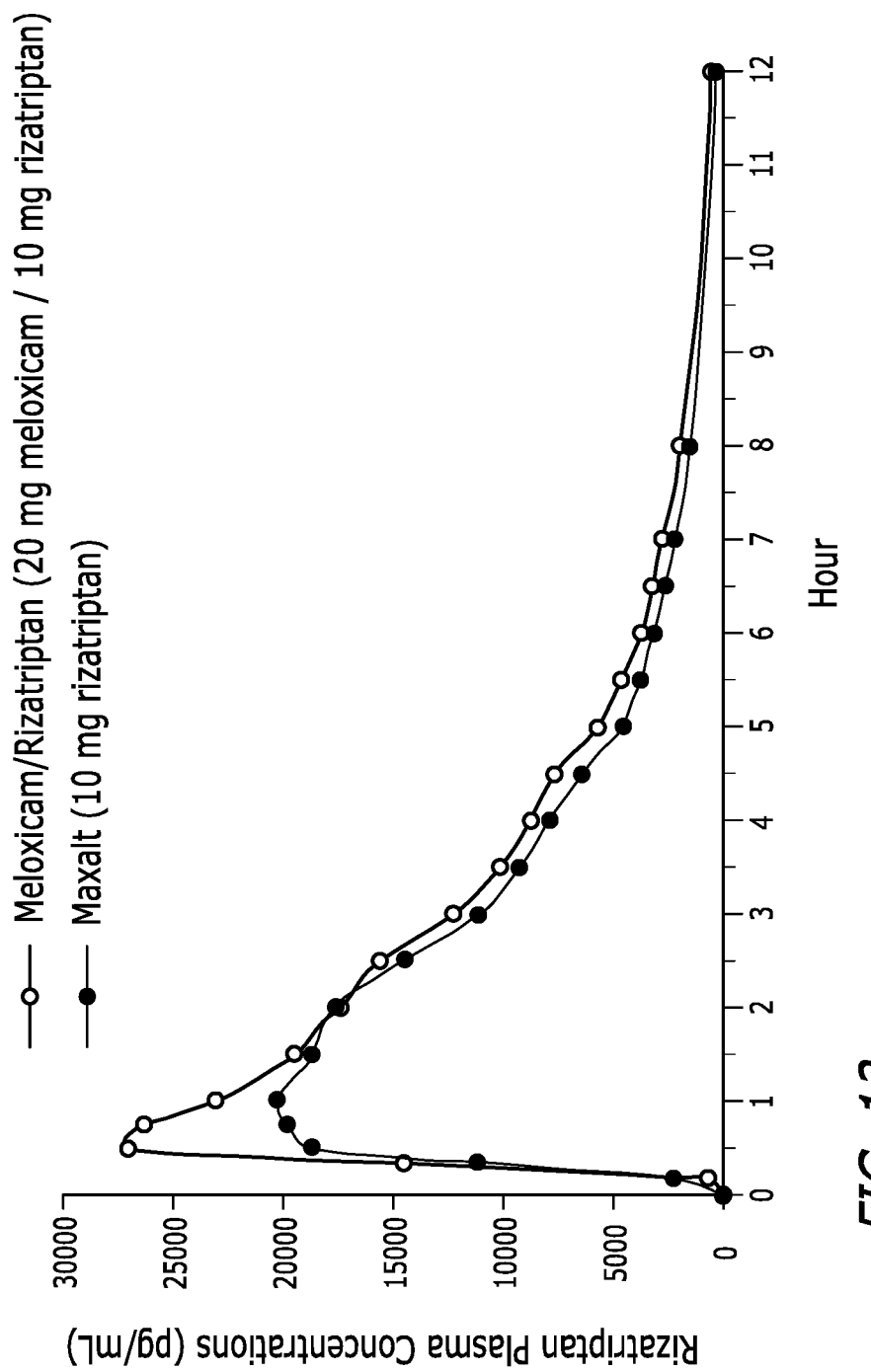
FIG. 13 is a plot of rizatriptan plasma concentration at various time points over the first 12 hours for a dosage form of Meloxicam/Rizatriptan described in Example 6 and a commercially available meloxicam dosage form.

Rizatriptan was rapidly absorbed after oral administration of meloxicam/rizatriptan, with a $T_{max}$ of 0.64 hour (38 min), which compares to 0.88 hour for the same dose of standard rizatriptan (Maxalt®) (FIG. 13 and Table 9). Systemic exposure measured using $C_{max}$ and AUC were also numerically greater for rizatriptan after administration of meloxicam/rizatriptan versus standard rizatriptan.

TABLE 9

Rizatriptan Pharmacokinetic Parameters for Meloxicam/Rizatriptan and Standard Rizatriptan

| | Statistic | $AUC_{0-inf}$ (pg · hr/mL) | $T_{1/2}$ el (hr) | $C_{max}$ (ng/mL) | $T_{max}$ (hr)$^a$ |
|---|---|---|---|---|---|
| Meloxicam/Rizatriptan | N | 10 | 10 | 10 | 10 |
| (20 mg meloxicam/10 | Geometric Mean | 83,800 | 1.98 | 29,991 | 0.64 |
| mg rizatriptan) | SD | 22,787 | 0.28 | 11,041 | 0.5-2.5 |
| Standard Rizatriptan | N | 10 | 10 | 10 | 10 |
| (Maxalt ®) | Geometric Mean | 71,811 | 1.81 | 23,236 | 0.88 |
| (10 mg rizatriptan) | SD | 24,287 | 0.11 | 9,476 | 0.5-2 |

$^a T_{max}$ presents the value as a median or a range.

Meloxicam/rizatriptan was well tolerated with no relevant differences in safety profile between the two treatment arms. There were no serious adverse events in the study.

Example 7

A Phase 3, randomized, double-blind, multicenter, active- and placebo-controlled trial is carried out to assess the efficacy and safety of meloxicam/rizatriptan in the acute treatment of moderate and severe migraine, in patients with a history of inadequate response to prior acute migraine treatments. Eligible patients are randomized in a 2:2:2:1 ratio to treatment with meloxicam/rizatriptan (20 mg meloxicam/10 mg rizatriptan, with SBEβCD and sodium bicarbonate as described in Example 4 above), rizatriptan (10 mg) (rizatriptan arm), meloxicam (20 mg) with SBEβCD and sodium bicarbonate (meloxicam arm), or placebo. Co-primary endpoints are freedom from headache pain, and freedom from the most bothersome migraine-associated symptom (nausea, photophobia, or phonophobia), two hours after dosing, for meloxicam/rizatriptan as compared to placebo.

Superiority of meloxicam/rizatriptan to the rizatriptan and the meloxicam arms (component contribution) will be established based on sustained freedom from headache pain from 2 hours to 24 hours after dosing (key secondary endpoint).

Eligible patients must have a history of inadequate response to prior acute migraine treatments, assessed using the Migraine Treatment Optimization Questionnaire (mTOQ-4). The mTOQ-4 is a validated questionnaire that assesses efficacy response to prior acute treatments based on four aspects (two-hour pain freedom, efficacy for at least 24 hours with one dose, ability to plan daily activities, and disruption of daily activities).

It is expected that meloxicam/rizatriptan will show significant improvement over placebo and superiority over the rizatriptan and the meloxicam arms because of the rapid absorption and distinct dual mechanisms of action of meloxicam/rizatriptan described herein.

Example 8

A female migraine sufferer visits her physician in the hope of having relief from her migraine pain. Her doctor gives her 10 mg rizatriptan (Maxalt®), which she takes during her next acute migraine. It provides some relief of pain, nausea, allodynia, such as cutaneous allodynia, photophobia, and phonophobia, but not complete relief from these symptoms. On her next visit, her doctor gives her 20 mg of meloxicam in a tablet also containing SBEβD and 500 mg of sodium bicarbonate, which she takes during her next acute migraine. It provides some relief of pain, nausea, allodynia, such as cutaneous allodynia, photophobia, and phonophobia, but not complete relief from these symptoms. On her next visit, her doctor gives her a tablet described in Example 4 above. She reports that at 2 hours and 24 hours after taking the tablet, she has about 10-30% improvement in pain, nausea, allodynia, such as cutaneous allodynia, photophobia, and/or phonophobia over what she experienced after taking meloxicam or rizatriptan alone.

Example 9

A male migraine sufferer visits his physician in the hope of having relief from his migraine pain. His doctor gives him 10 mg rizatriptan (Maxalt®), which he takes during his next acute migraine. It provides some relief of pain, nausea, allodynia, such as cutaneous allodynia, photophobia, and phonophobia, but not complete relief from these symptoms. On his next visit, his doctor gives his 20 mg of meloxicam in a tablet also containing SBEβD and 500 mg of sodium bicarbonate, which he takes during his next acute migraine. It provides some relief of pain, nausea, allodynia, such as cutaneous allodynia, photophobia, and phonophobia, but not complete relief from these symptoms. On his next visit, his doctor gives him a tablet described in Example 4 above. He reports that at 2 hours and 24 hours after taking the tablet, he has about 30-60% improvement in pain, nausea, allodynia, such as cutaneous allodynia, photophobia, and/or phonophobia over what he experienced after taking meloxicam or rizatriptan alone.

Example 10

A female migraine sufferer visits her physician in the hope of having relief from her migraine pain. Her doctor gives her 10 mg rizatriptan (Maxalt®), which she takes during her next acute migraine. It provides some relief of pain, nausea, allodynia, such as cutaneous allodynia, photophobia, and phonophobia, but not complete relief from these symptoms. On her next visit, her doctor gives her 20 mg of meloxicam in a tablet also containing SBEβCD and 500 mg of sodium bicarbonate, which she takes during her next acute migraine. It provides some relief of pain, nausea, allodynia, such as cutaneous allodynia, photophobia, and phonophobia, but not complete relief from these symptoms. On her next visit, her doctor gives her a tablet described in Example 4 above. She reports that at 2 hours and 24 hours after taking the tablet, she has about 60-100% improvement in pain, nausea, allodynia, such as cutaneous allodynia, photophobia, and/or phonophobia over what she experienced after taking meloxicam or rizatriptan alone.

Example 11

Over 37 million Americans suffer from migraine according to the Centers for Disease Control, and it is the leading cause of disability among neurological disorders in the United States according to the American Migraine Foundation. Migraine is characterized by recurrent attacks of pulsating, often severe and disabling head pain associated with nausea, and sensitivity to light and or sound. It is estimated that migraine accounts for $78 billion in direct (e.g. doctor visits, medications) and indirect (e.g. missed work, lost productivity) costs each year in the United States [Gooch C L, Pracht E, Borenstein A R, The burden of neurological disease in the United States: A summary report and call to action. Ann Neurol. 2017 April; 81(4):479-484]. Published surveys of migraine sufferers indicate that more than 70% are not fully satisfied with their current treatment, that nearly 80% would try a new therapy, and that they desire treatments that work faster, more consistently, and result in less symptom recurrence [(1) Smelt A F, Louter M A, Kies D A, Blom J W, Terwindt G M, van der Heijden G J, De Gucht V, Ferrari M D, Assendelft W J, What do patients consider to be the most important outcomes for effectiveness studies on migraine treatment? Results of a Delphi study. PLoS One. 2014 Jun. 16; 9(6):e98933, 6; and (2) Lipton R B, Stewart W F, Acute migraine therapy: do doctors understand what patients with migraine want from therapy? Headache. 1999; 39(suppl 2):520-526].

The World Health Organization classifies severe migraine attacks as among the most disabling illnesses, comparable to dementia, quadriplegia and active psychosis [(1) Menken et al. *Arch Neurol.* 2000; 57:418-420; and (2) Shapiro and Goadsby. *Cephalalgia.* 2007; 27:991-4]. Debilitating pain, and the often-constant fear of the next migraine attack, damage family life, social life, and employment [Global Burden of Disease Study. *Lancet.* 2017; 390:1211-1259]. Depression and anxiety are twice as common in people with migraine than in healthy individuals [Antonaci et al. *J Headache Pain.* 2011; 12:115-125]. Widespread misperception of the seriousness of migraine contributes to its under-recognition and under-treatment [Global Burden of Disease Study. *Lancet.* 2017; 390:1211-1259]. The majority of patients are not fully satisfied with their current treatment. Thus, there is an urgent need for new treatments that provide improved efficacy for this serious neurological disease.

A Phase 3, randomized, double-blind, multicenter, placebo- and active-controlled trial was conducted to assess the efficacy and safety of the combination of meloxicam and rizatriptan (meloxicam/rizatriptan) in the acute treatment of moderate and severe migraine. Eligible patients must have an age of 18 to 65 years, an established diagnosis (at least 1 year) of migraine with or without aura as defined by ICHD-3 criteria, an average of 2 to 8 moderate to severe migraines per month, had a history of inadequate response to prior acute migraine treatments, assessed by a score of 7 using the Migraine Treatment Optimization Questionnaire (mTOQ-4) (the average score was 3.6), corresponding to poor response to prior acute treatments. Exclusion criteria included cluster headaches or other types of migraines, chronic daily headache 15 non-migraine headache days per month), history of significant cardiovascular disease, and uncontrolled hypertension. In addition to a history of inadequate response, enrolled patients exhibited a high rate of characteristics that are strongly associated with poor treatment outcomes including cutaneous allodynia (75.4%), severe migraine pain intensity (41.2%), obesity (43.7%), and morning migraine (36.6%). A total of 1,594 patients were randomized in a 2:2:2:1 ratio to the monolayer tablet of Example 4 (20 mg meloxicam/10 mg rizatriptan, with SBEβCD and sodium bicarbonate), rizatriptan (10 mg), meloxicam (20 mg) with SBEβCD (MoSEIC Meloxicam), or placebo, to treat a single migraine attack of moderate or severe intensity. The two co-primary endpoints of the trial were the proportion of patients who are free from headache pain two hours after dosing, and the proportion of patients who no longer suffered from their most bothersome migraine-associated symptom (nausea, photophobia, or phonophobia) two hours after dosing, for meloxicam/rizatriptan as compared to placebo. Superiority of meloxicam/rizatriptan to the rizatriptan and meloxicam arms (component contribution) was to be established based on sustained freedom from headache pain from two to 24 hours after dosing (key secondary endpoint). The study was conducted pursuant to an FDA Special Protocol Assessment (SPA). Rizatriptan, an active comparator in the trial, is considered to be the fastest acting oral triptan and one of the most effective medications currently available for the acute treatment of migraine. (Ferrari M D, Roon K I, Lipton R B, Goadsby Pi. Oral triptans (serotonin 5-HT(1B/1D) agonists) in acute migraine treatment: a meta-analysis of 53 trials. Lancet. 2001 Nov. 17; 358(9294):1668-75.)

Figure 14:
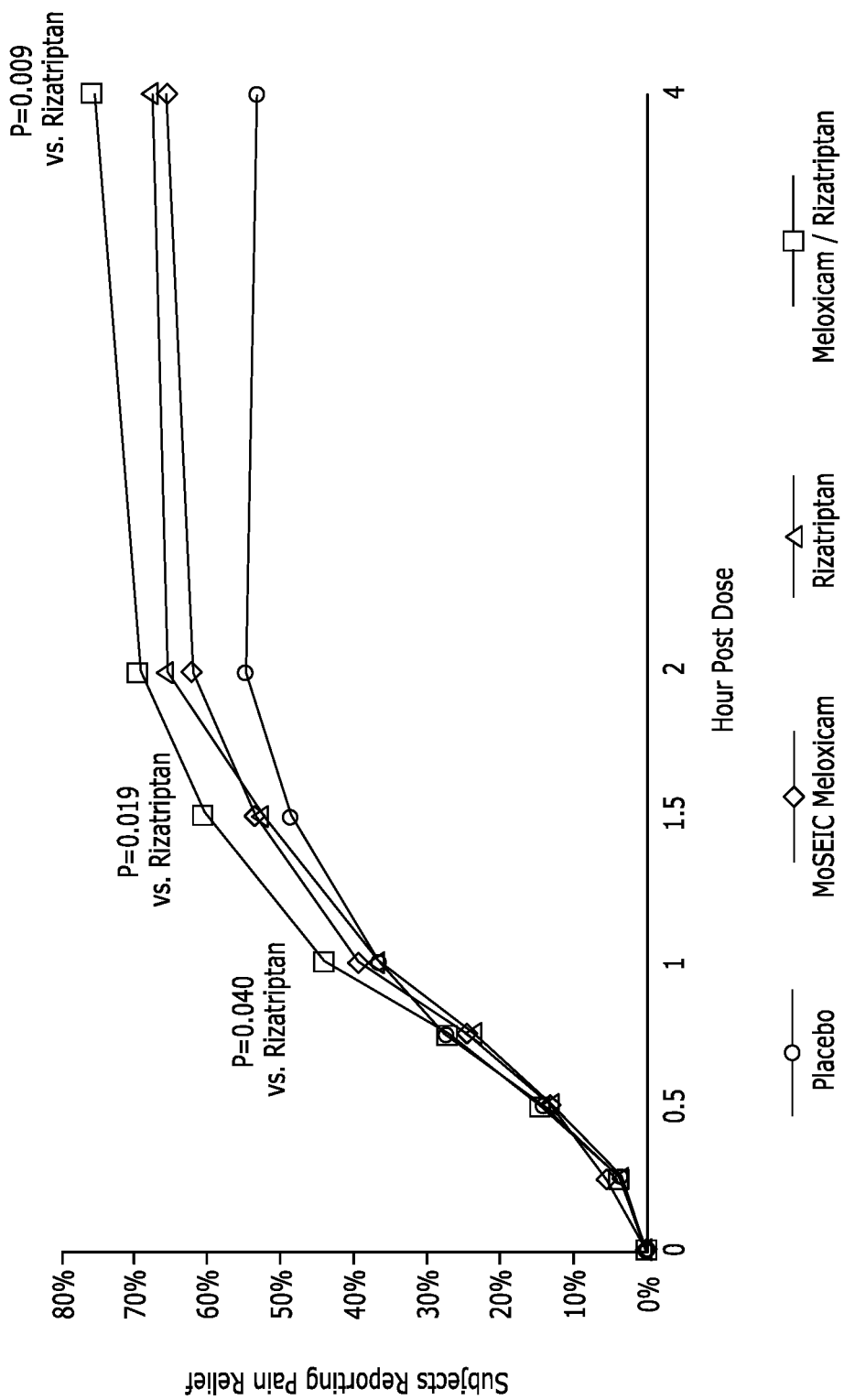
FIG. 14 shows plots of the percentages of subjects reporting pain relief at various time points over the first 4 hours post dose of the dosage forms of Meloxicam/Rizatriptan, rizatriptan, MoSEIC meloxicam, and placebo described in Example 11.
Figure 14A:
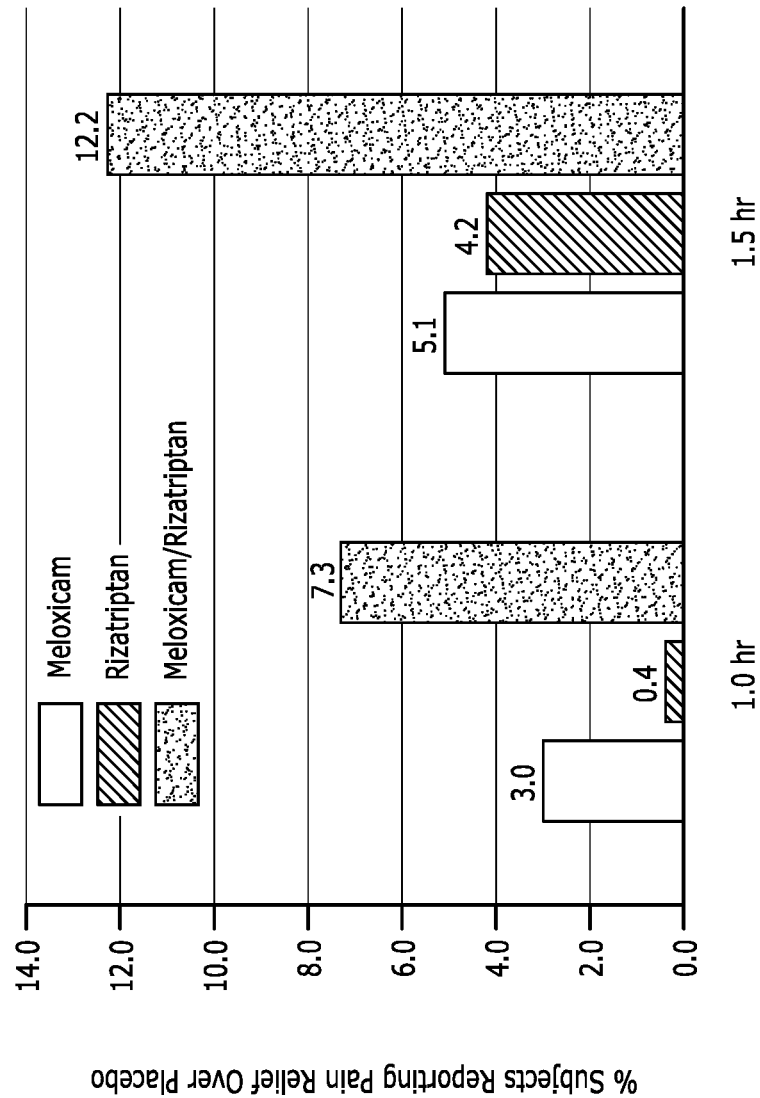
FIG. 14A shows the percentage of subjects reporting pain relief over placebo for meloxicam, rizatriptan, and meloxicam/rizatriptan at 1.0 hour and 1.5 hours.

Meloxicam/rizatriptan provided rapid relief of migraine pain with the percentage of patients achieving pain relief with meloxicam/rizatriptan being numerically greater than with rizatriptan at every time point measured starting at 15 minutes, and statistically significant by 60 minutes (p=0.04) (FIG. 14). The proportions of patients experiencing pain relief 1.5 hours after dosing were 60.5% for meloxicam/rizatriptan compared to 52.5% for rizatriptan and 48.3% for placebo (p=0.019, p=0.04, respectively versus meloxicam/rizatriptan) (FIG. 14). FIG. 14A shows the percentage of subjects reporting pain relief over placebo for meloxicam, rizatriptan, and meloxicam/rizatriptan at 1.0 hour and 1.5 hours.

Figure 15:
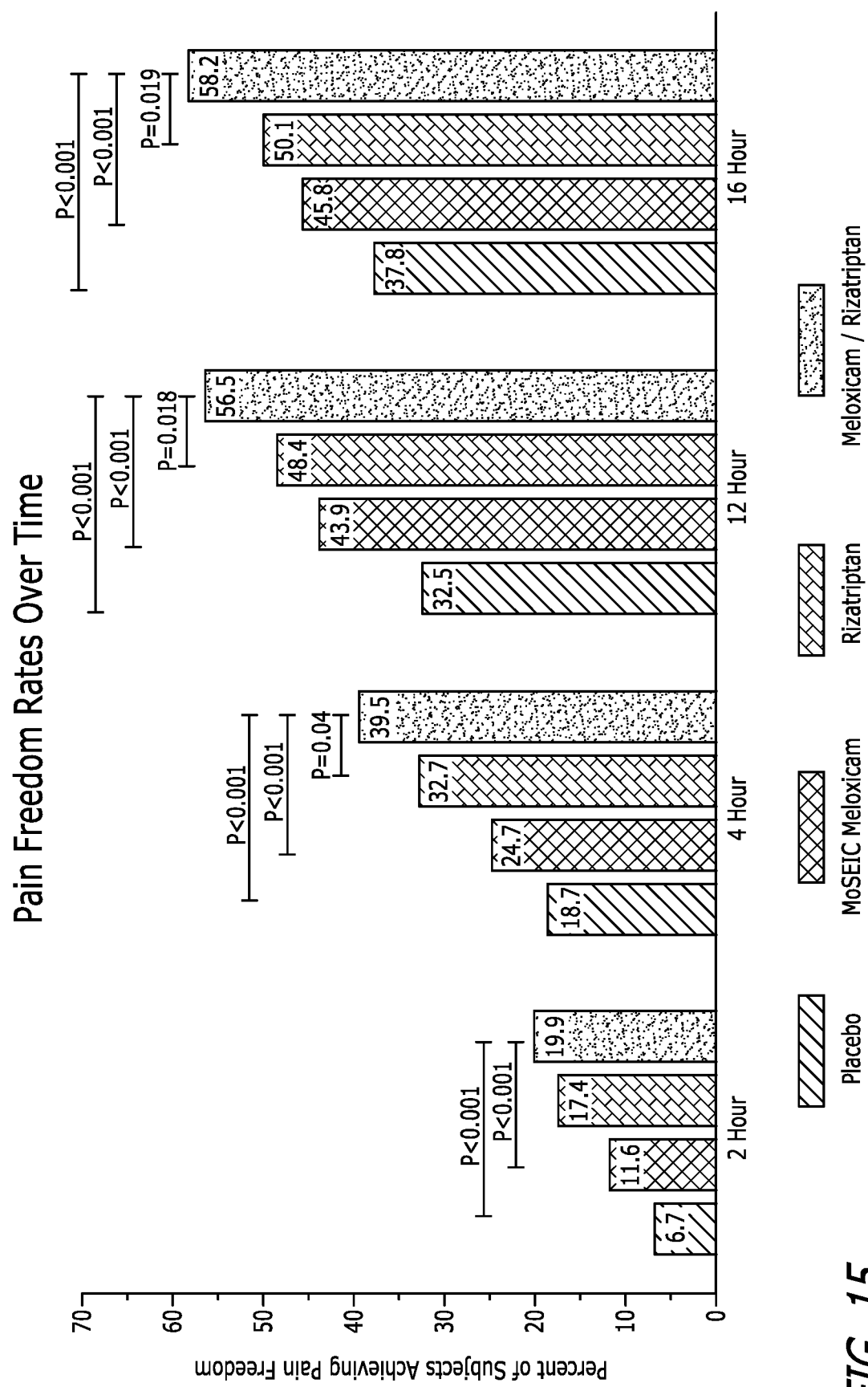
FIG. 15 shows the percentages of subjects achieving pain freedom at 2 hours, 4 hours, 12 hours, and 16 hours post dose of the dosage forms of Meloxicam/Rizatriptan, rizatriptan, MoSEIC meloxicam, and placebo described in Example 11.

Meloxicam/rizatriptan met the two regulatory co-primary endpoints by demonstrating, with high statistical significance, a greater percentage of patients as compared to placebo achieving pain freedom (19.9% versus 6.7%, p<0.001, FIG. 15), and absence of most bothersome symptom (36.9% versus 24.4%, p=0.002), 2 hours after dosing.

Figure 16B:
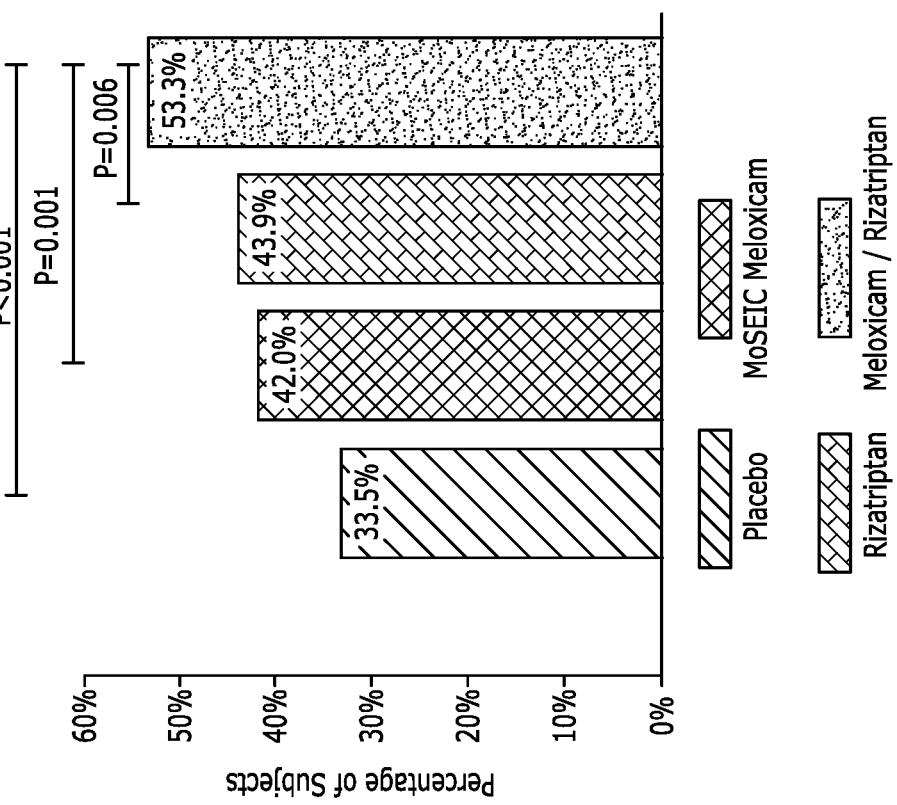
FIG. 16B shows the percentages of subjects achieving sustained pain relief from 2 hours to 24 hours post dose of the dosage forms of Meloxicam/Rizatriptan, rizatriptan, MoSEIC meloxicam, and placebo described in Example 11.
Figure 16A:
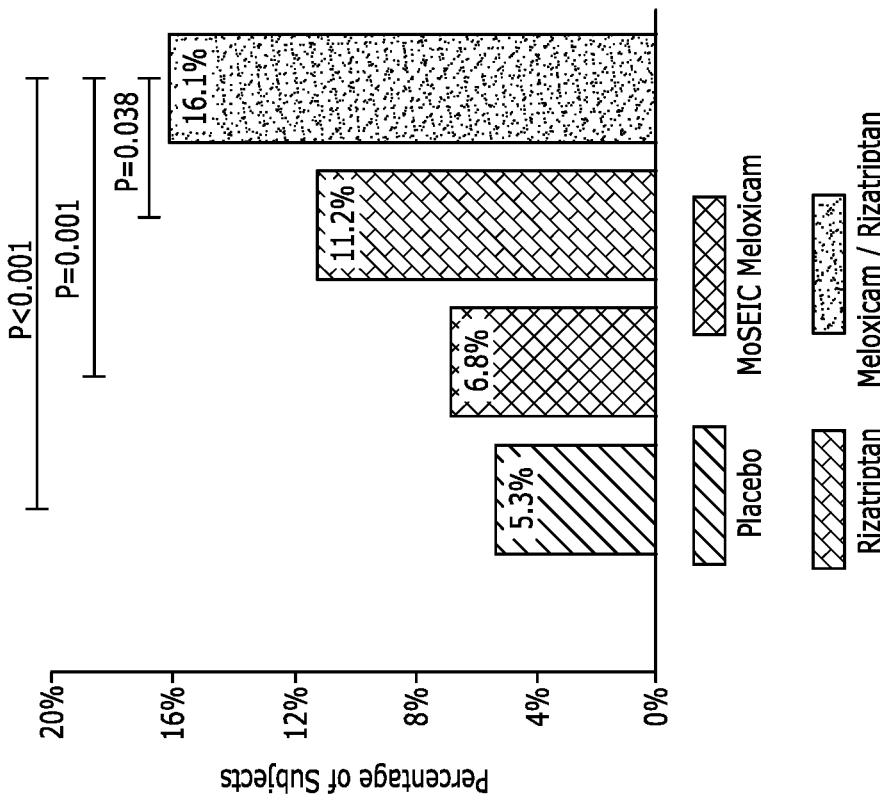
FIG. 16A shows the percentages of subjects achieving sustained pain freedom from 2 hours to 24 hours post dose of the dosage forms of Meloxicam/Rizatriptan, rizatriptan, MoSEIC meloxicam, and placebo described in Example 11.

Superiority of meloxicam/rizatriptan to rizatriptan (active comparator) and MoSEIC™ meloxicam (component contribution) was established as specified in the SPA, by the demonstration of a greater percentage of patients receiving meloxicam/rizatriptan achieving sustained pain freedom from 2 hours to 24 hours after dosing, compared to rizatriptan, MoSEIC™ meloxicam, and placebo (16.1%, 11.2%, 6.8% and 5.3%, respectively; p=0.038, p=0.001, and p<0.001, respectively versus meloxicam/rizatriptan, FIG. 16A), the pre-specified key secondary endpoint to demonstrate component contribution. About 80% of the patients treated with meloxicam/rizatriptan who achieved pain freedom at 2 hours maintained pain freedom through 24 hours. These results demonstrated the significant improvement in pain freedom and superiority of meloxicam/rizatriptan to rizatriptan in treating migraine.

Meloxicam/rizatriptan provided substantially greater and more sustained migraine pain relief compared to placebo and rizatriptan, which translated to a significant reduction in rescue medication use for meloxicam/rizatriptan compared to placebo and rizatriptan. The percentage of patients experiencing sustained pain relief from 2 hours to 24 hours after dosing was 53.3% for meloxicam/rizatriptan, compared to 33.5% for placebo and 43.9% for rizatriptan (p<0.001, p=0.006, respectively versus meloxicam/rizatriptan) (FIG. 16B).

Figure 17B:
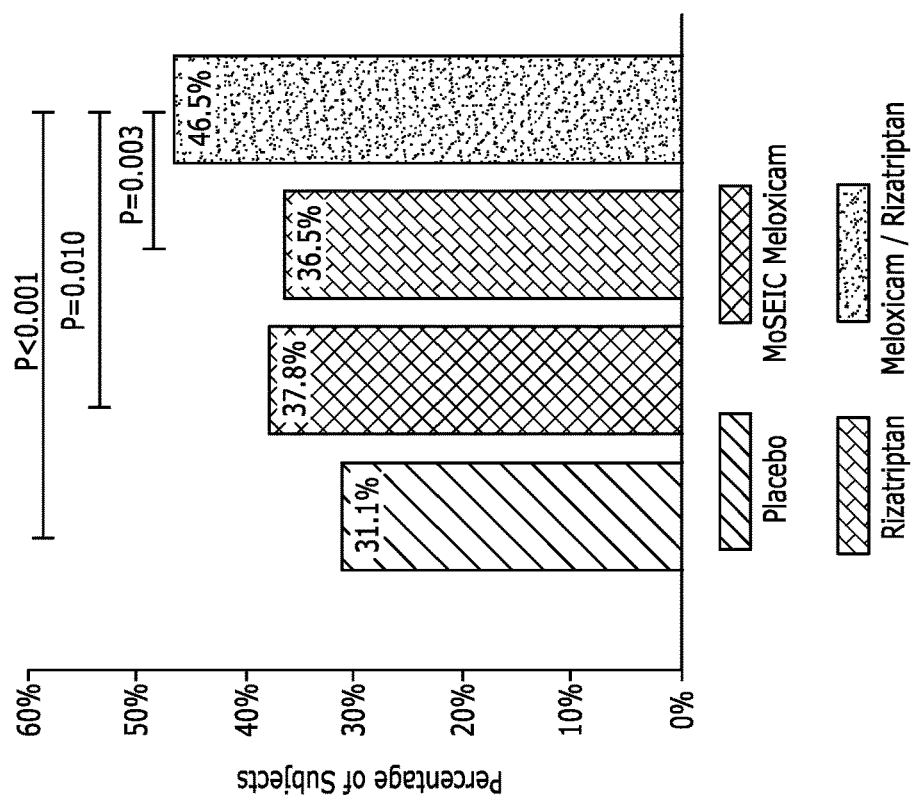
FIG. 17B shows the percentages of subjects achieving sustained pain relief from 2 hours to 48 hours post dose of the dosage forms of Meloxicam/Rizatriptan, rizatriptan, MoSEIC meloxicam, and placebo described in Example 11.
Figure 17A:
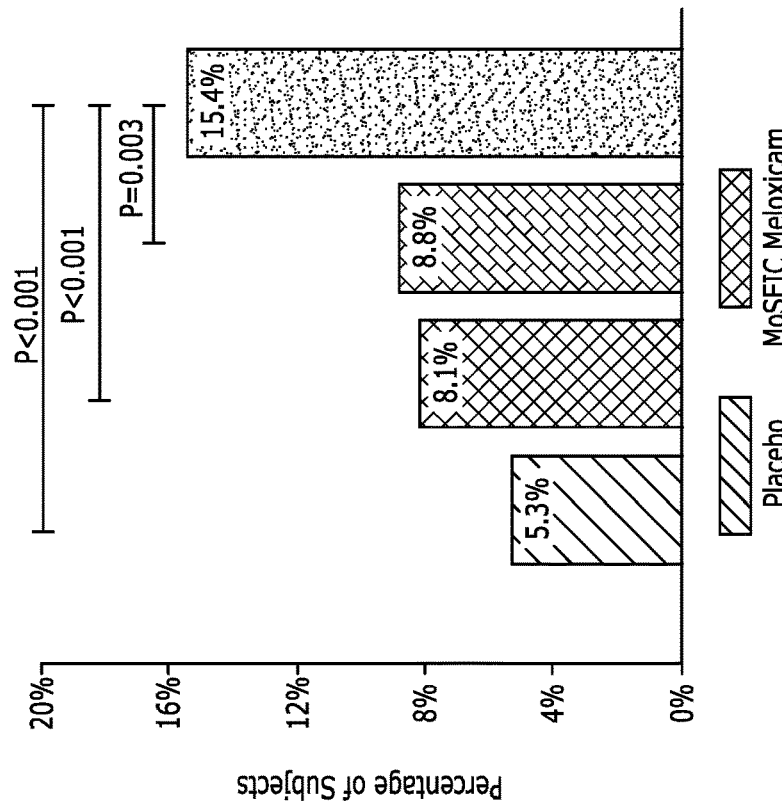
FIG. 17A shows the percentages of subjects achieving sustained pain freedom from 2 hours to 48 hours post dose of the dosage forms of Meloxicam/Rizatriptan, rizatriptan, MoSEIC meloxicam, and placebo described in Example 11.
Figure 17D:
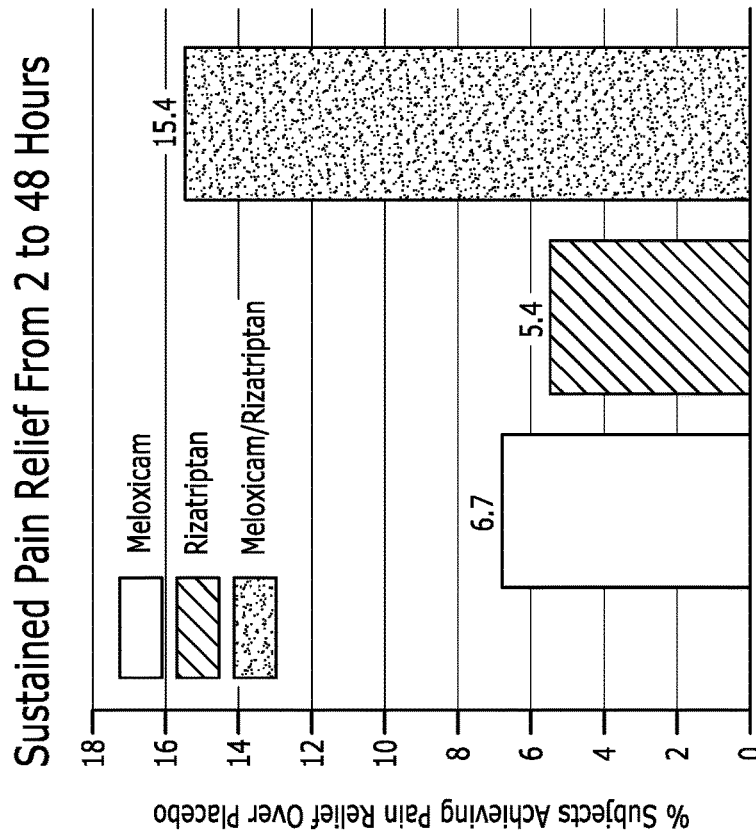
FIG. 17D shows the percentage of subjects achieving sustained pain relief over placebo from 2 hours to 48 hours for meloxicam, rizatriptan, and meloxicam/rizatriptan.
Figure 17C:
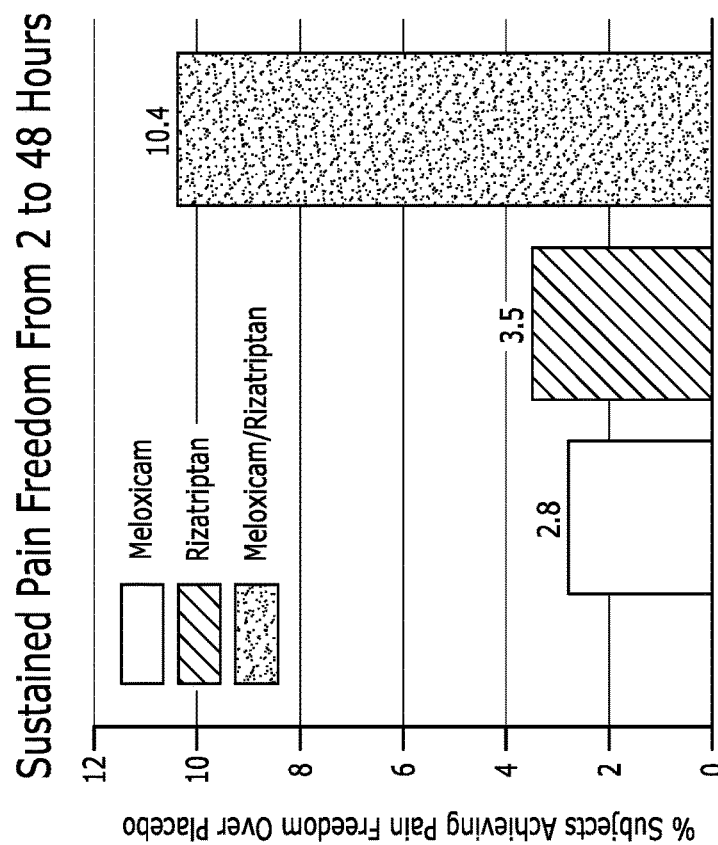
FIG. 17C shows the percentage of subjects achieving sustained pain freedom over placebo from 2 hours to 48 hours for meloxicam, rizatriptan, and meloxicam/rizatriptan.

Sustained pain relief from 2 hours to 48 hours was also experienced by a statistically significantly greater proportion of meloxicam/rizatriptan patients (46.5%), compared to placebo (31.1%) and rizatriptan (36.5%) patients (p<0.001, p=0.003, respectively versus meloxicam/rizatriptan) (FIG. 17B). FIG. 17D shows the percentage of subjects achieving sustained pain relief over placebo from 2 hours to 48 hours for meloxicam, rizatriptan, and meloxicam/rizatriptan. The sustained pain freedom from 2 hours to 48 hours was also experienced by a statistically significantly greater proportion of meloxicam/rizatriptan patients (15.4%), compared to placebo (5.3%), and rizatriptan (8.8%), and MoSEIC™ meloxicam (8.1%) patients (p<0.001, p=0.003, p=<0.001, respectively versus meloxicam/rizatriptan) (FIG. 17A). FIG. 17C shows the percentage of subjects achieving sustained pain freedom over placebo from 2 hours to 48 hours for meloxicam, rizatriptan, and meloxicam/rizatriptan. About 77% of patients treated with meloxicam/rizatriptan who achieved pain freedom at 2 hours maintained the pain freedom through 48 hours.

Figure 18:
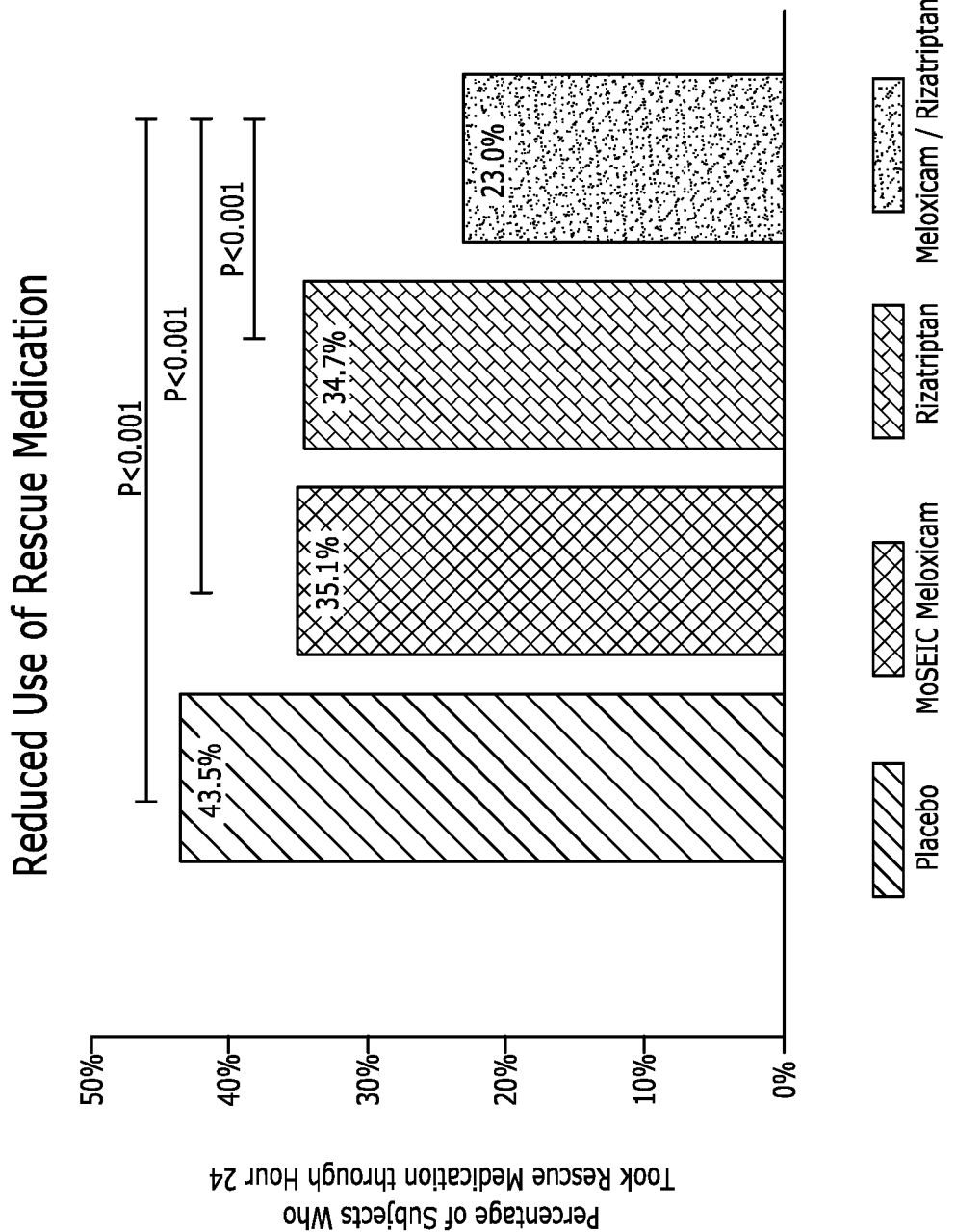
FIG. 18 shows the percentages of subjects who took rescue medication through hour 24 post dose of the dosage forms of Meloxicam/Rizatriptan, rizatriptan, MoSEIC meloxicam, and placebo described in Example 11.

Rescue medication was used by 23.0% patients received meloxicam/rizatriptan, compared to 43.5% patients received placebo and 34.7% patients received rizatriptan (p<0.001 for each group versus meloxicam/rizatriptan) (FIG. 18). About 77% of patients receiving meloxicam/rizatriptan did not require rescue medication. These results demonstrated the superiority of meloxicam/rizatriptan to rizatriptan, an active comparator, in treating migraine.

Meloxicam/rizatriptan was statistically significantly superior to rizatriptan on several other secondary endpoints, including Patient Global Impression of Change (PGI-C) (p=0.022), and return to normal functioning at 24 hours (p=0.027).

Some of the p-values for meloxicam/rizatriptan versus rizatriptan for various endpoints are listed in Table 10 below, demonstrating the statistically significant superiority of meloxicam/rizatriptan over rizatriptan in treating migraine.

TABLE 10

P-Values for Meloxicam/Rizatriptan vs Rizatriptan for Various Endpoints

| Endpoint | P-value Meloxicam/Rizatriptan vs Rizatriptan |
|---|---|
| 1 hour Pain Relief | 0.04 |
| 2-24 hour Sustained Pain Relief | 0.006 |
| 2-48 hour Sustained Pain Relief | 0.003 |
| 2-24 hour Sustained Pain Freedom | 0.038 |
| 2-48 hour Sustained Pain Freedom | 0.003 |
| PGI-C | 0.022 |
| Functional Improvement at 24 hours | 0.027 |
| Use of Rescue Medication | <0.001 |

Given that Rizatriptan, an active comparator in the trial, is considered to be the fastest acting oral triptan and one of the most effective medications currently available for the acute treatment of migraine, and that this trial enrolled patients with difficult-to-treat migraine, the observed treatment effects with meloxicam/rizatriptan that provided greater and more lasting migraine pain relief than rizatriptan, is highly significant. Many patients experience a suboptimal response to their current acute migraine treatments, placing them at increased risk of headache related disability and progression to chronic migraine, factors associated with increased healthcare costs. The results of this study suggest that meloxicam/rizatriptan may provide an important treatment option for people with difficult-to-treat migraine.

Meloxicam/rizatriptan was safe and well tolerated in the patients studied in the trial. The most commonly reported adverse events with meloxicam/rizatriptan were nausea, dizziness and somnolence, none of which occurred at a rate greater than placebo or greater than 3%. There was one serious adverse event in the meloxicam/rizatriptan arm which was deemed by the investigator not to be related to the study drug.

The results of this trial demonstrate the ability of meloxicam/rizatriptan to provide unique benefits to migraine patients, with fast, strong, and durable relief of migraine pain as compared to a potent active comparator, rizatriptan, in a stringently designed trial enriched with patients with difficult-to-treat migraine. These results have potentially important implications for patient care based on the high rate of inadequate response to and patient dissatisfaction with current treatments.

Meloxicam/rizatriptan incorporates multiple mechanisms of action to address various migraine processes with the goal of providing enhanced effectiveness. Meloxicam/rizatriptan is thought to act by inhibiting CGRP release, reversing CGRP-mediated vasodilation, and inhibiting neuro-inflammation, pain signal transmission, and central sensitization. The results of this trial validate this approach, demonstrating that meloxicam/rizatriptan can provide significant benefit that is greater than that of currently available treatments, even in patients with difficult-to-treat migraine. Meloxicam/rizatriptan may be used for the acute treatment of migraine in adults with or without aura effectively.

Example 12

A Phase 3, randomized, double-blind, multicenter, placebo-controlled trial was conducted evaluating the early treatment of migraine with meloxicam/rizatriptan. A total of 302 patients were randomized in a 1:1 ratio to treat a single migraine attack with a single dose of meloxicam/rizatriptan (20 mg meloxicam/10 mg rizatriptan, with SBEβCD and sodium bicarbonate as described in Example 4 above), or placebo, at the earliest sign of migraine pain, while the pain was mild, before progressing to moderate or severe intensity.

This clinical trial is different from the clinical trial in Example 11. The clinical trial of Example 11 enrolled only patients with a history of inadequate response to prior acute treatments, with patients waiting to treat their attacks only when the migraine pain had reached moderate or severe intensity. The clinical trial in Example 11 is in contrast to this clinical trial, which enrolled all corners and in which patients were instructed to administer meloxicam/rizatriptan at the earliest sign of migraine pain while the pain was mild, before progressing to moderate or severe intensity.

The patients were adult subjects with an established diagnosis of migraine with or without aura.

Co-primary endpoints are freedom from headache pain, and freedom from the most bothersome migraine-associated symptom (nausea, photophobia, or phonophobia), two hours after dosing, for meloxicam/rizatriptan as compared to placebo.

Secondary endpoints included sustained pain freedom, freedom from migraine pain progression, change in functional disability, and use of rescue medication.

Inclusion criteria included male or female at ages 18-65 inclusive, an established diagnosis (at least 1 year) of migraine with or without aura as defined by the ICHD-3 criteria, and an average of 2 to 8 migraines per month. Exclusion criteria included cluster headaches, tension headaches, or other types of migraines, chronic daily headache (≥15 non-migraine headache days per month), history of significant cardiovascular disease, and uncontrolled hypertension.

Meloxicam/rizatriptan substantially and significantly eliminated migraine pain, and substantially and significantly prevented progression of migraine pain intensity in this Phase 3 trial of meloxicam/rizatriptan in the early treatment of migraine. In the trial, meloxicam/rizatriptan met the co-primary endpoints of freedom from migraine pain and freedom from most bothersome symptoms as compared to placebo.

Figure 19B:
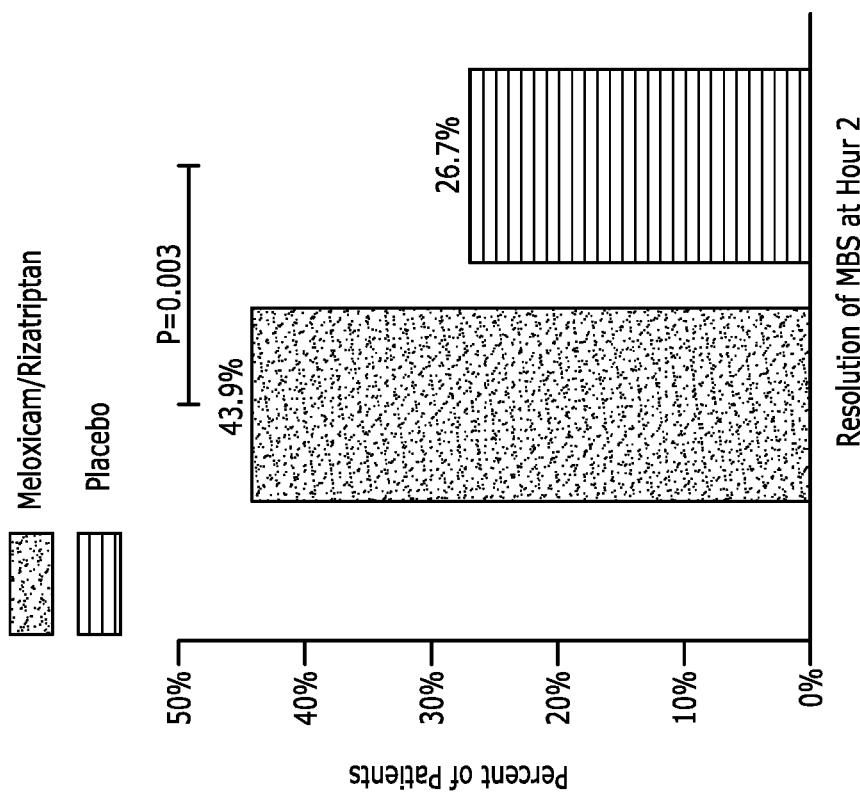
FIG. 19A and FIG. 19B show the percentage of subjects having freedom from pain and resolution of most bothersome symptom for subjects taking meloxicam/rizatriptan and placebo in Example 12.
Figure 19A:
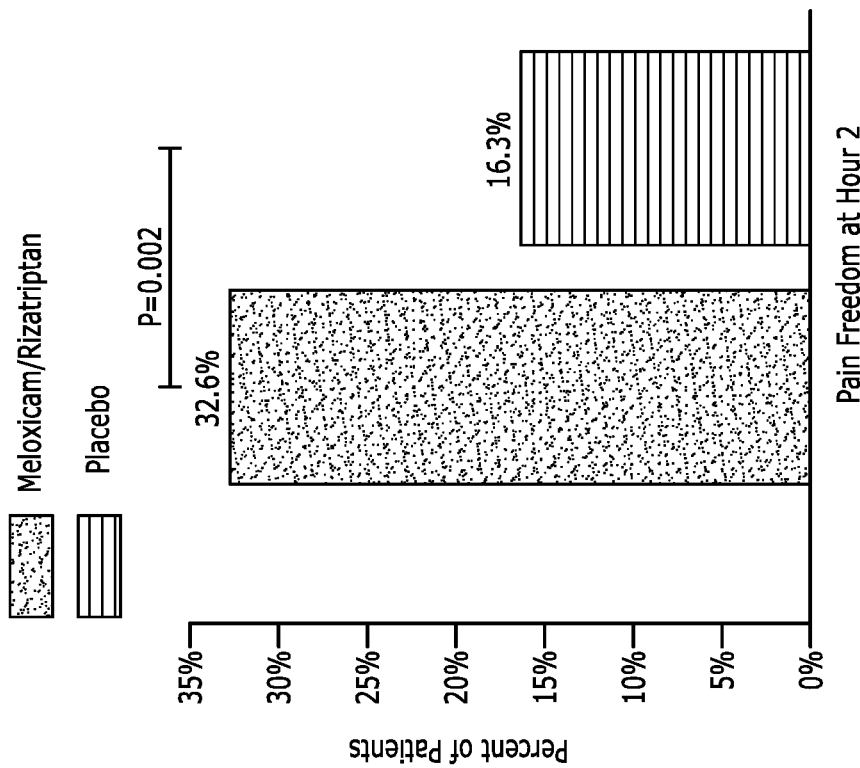

Meloxicam/rizatriptan demonstrated statistically significant improvement as compared to placebo on both of the co-primary endpoints of pain freedom (32.6% versus 16.3%, p=0.002), and freedom from most bothersome symptom (43.9% versus 26.7%, p=0.003), 2 hours after dosing (FIG. 19A and FIG. 19B). The most bothersome symptom is nausea, photophobia, or phonophobia.

Figure 20:
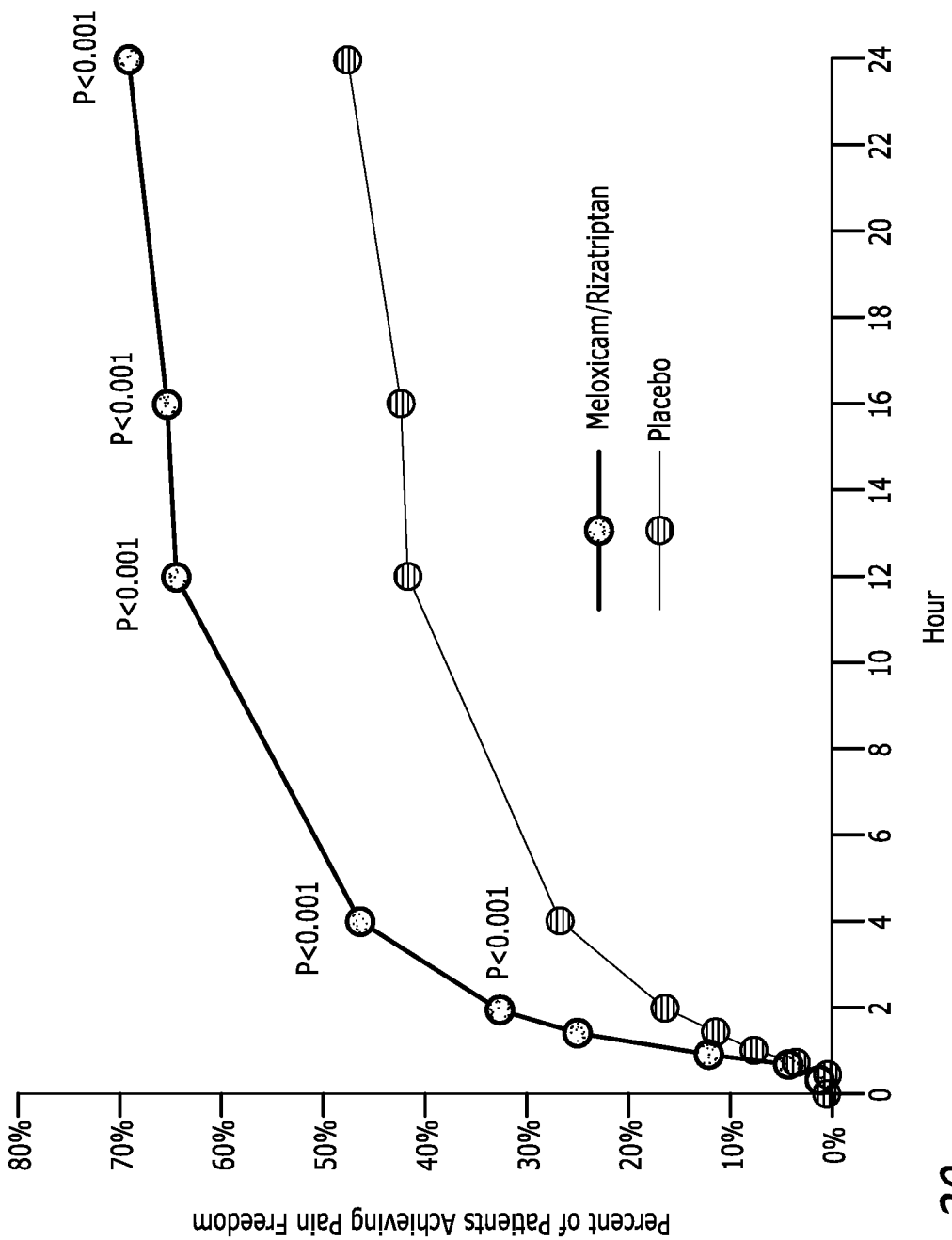
FIG. 20 shows the percentage of subjects achieving pain freedom over time for subjects taking meloxicam/rizatriptan and placebo in Example 12.
Figure 21:
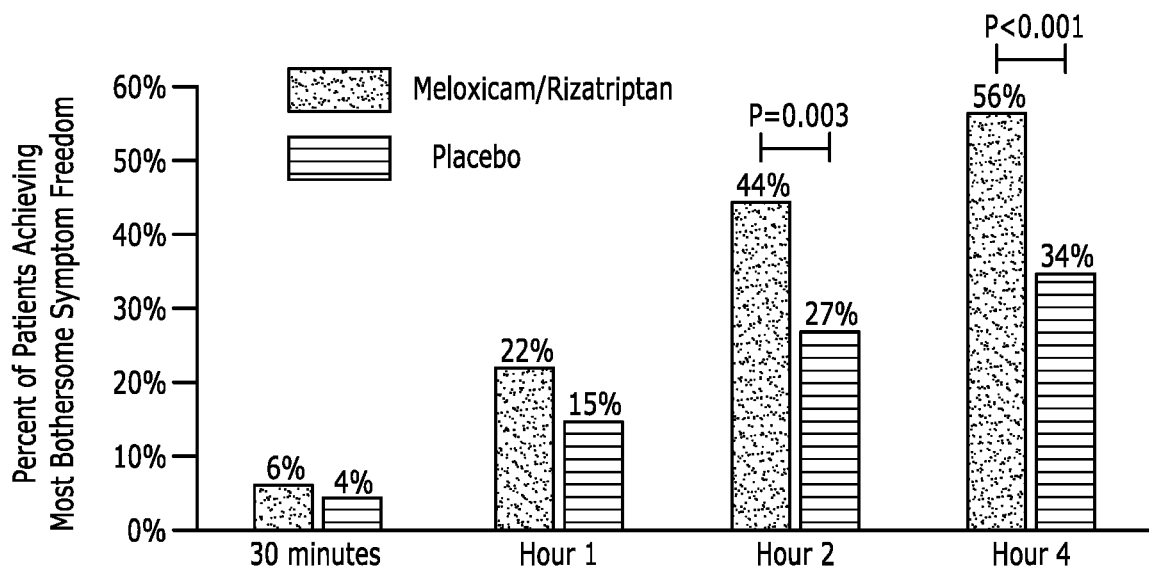
FIG. 21 shows the percentage of subjects achieving freedom from most bothersome symptom over time for subjects taking meloxicam/rizatriptan and placebo in Example 12.

Meloxicam/rizatriptan was numerically superior to placebo as early as 30 minutes for migraine pain freedom (FIG. 20) and most bothersome symptom freedom (FIG. 21), achieving statistical significance for migraine pain freedom at 90 minutes (p=0.003) and at every time thereafter (FIG. 20). At 12 hours, 64% of the patients receiving meloxicam/rizatriptan were pain free as compared to 42% of patients receiving placebo. At 24 hours, 69% of patients receiving meloxicam/rizatriptan were pain free as compared to 47% of patients receiving placebo.

Figures 22A, 22B:
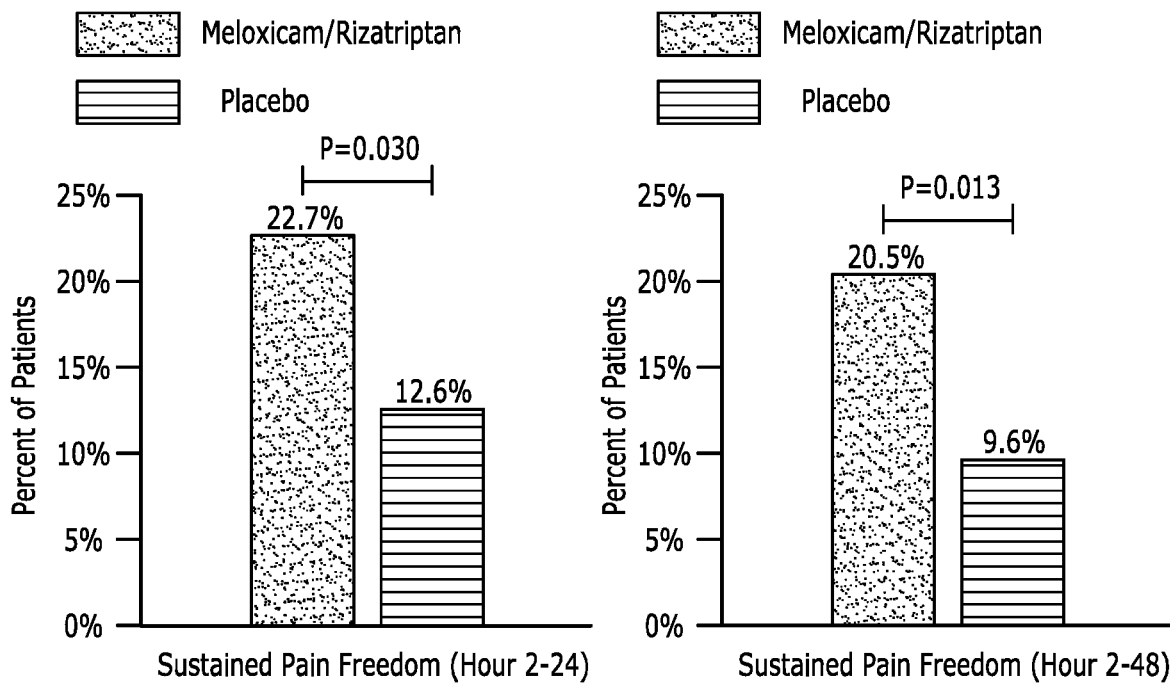
FIG. 22A and FIG. 22B show the percentage of subjects achieving pain freedom over hours 2-24 and hours 2-48 for subjects taking meloxicam/rizatriptan and placebo in Example 12.

Meloxicam/rizatriptan durably relieved migraine pain with a statistically significantly greater percentage of patients as compared to placebo achieving sustained pain freedom from 2 to 24 hours after dosing (22.7% versus 12.6%, p=0.030), and from 2 to 48 hours after dosing (20.5% versus 9.6%, p=0.013) (FIG. 22A and FIG. 22B).

Figure 23:
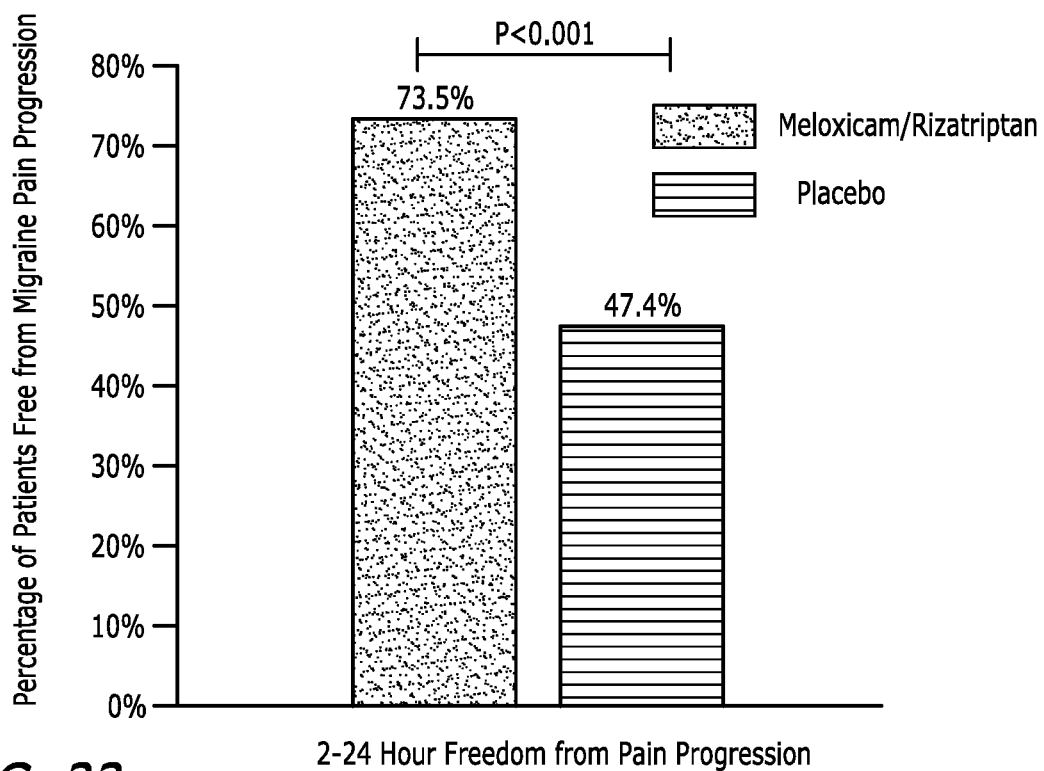
FIG. 23 shows the percentage of subjects achieving freedom from pain progression over hours 2-24 for subjects taking meloxicam/rizatriptan and placebo in Example 12.

Meloxicam/rizatriptan prevented progression of migraine pain intensity beyond mild in 73.5% of patients versus 47.4% of patients taking placebo from 2 to 24 hours (p<0.001) (FIG. 23). A single dose of meloxicam/rizatriptan prevented migraine pain progression beyond mild.

Figure 24:
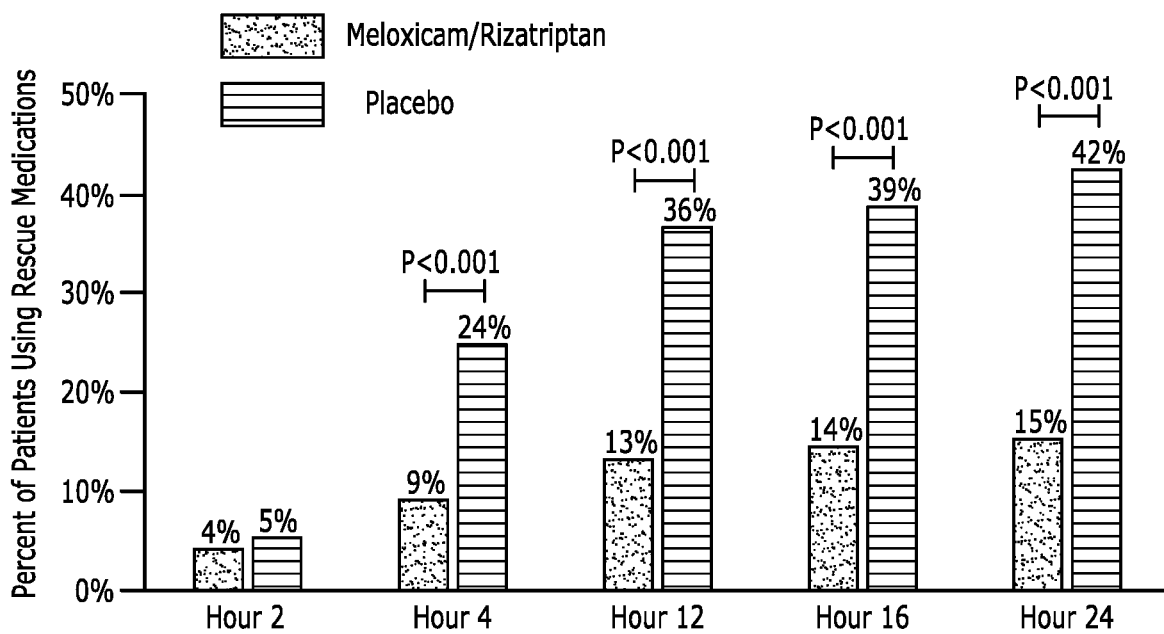
FIG. 24 shows the percentage of subjects taking rescue medication for subjects taking meloxicam/rizatriptan and placebo in Example 12.

The effect on pain progression translated to a significant reduction in the use of rescue medication, with only 15.3% of patients taking meloxicam/rizatriptan required rescue medication through 24 hours after dosing, versus 42.2% of patients taking placebo (p<0.001) (FIG. 24).

Figure 25:
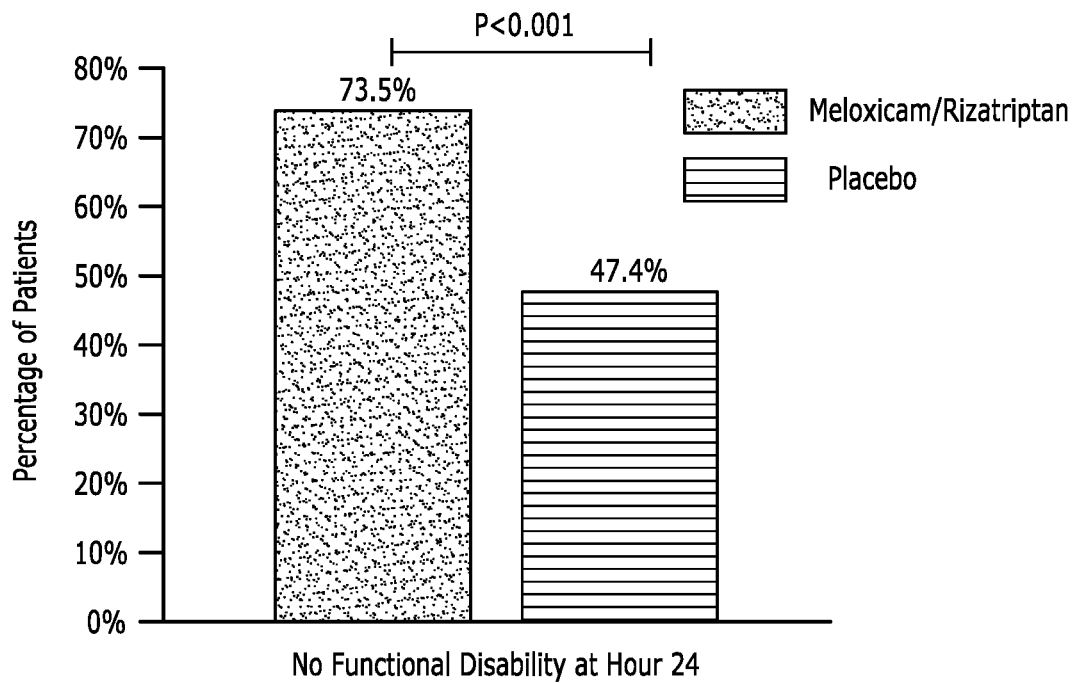
FIG. 25 shows the percentage of subjects having no functional disability at hour 24 for subjects taking meloxicam/rizatriptan and placebo in Example 12.

Meloxicam/rizatriptan substantially and significantly reduced functional disability, and demonstrated overall disease improvement. The ability to perform normal activities was achieved by 73.5% of patients taking meloxicam/rizatriptan compared to 47.4% of patients taking placebo at 24 hours (p<0.001) (FIG. 25).

Figure 26:
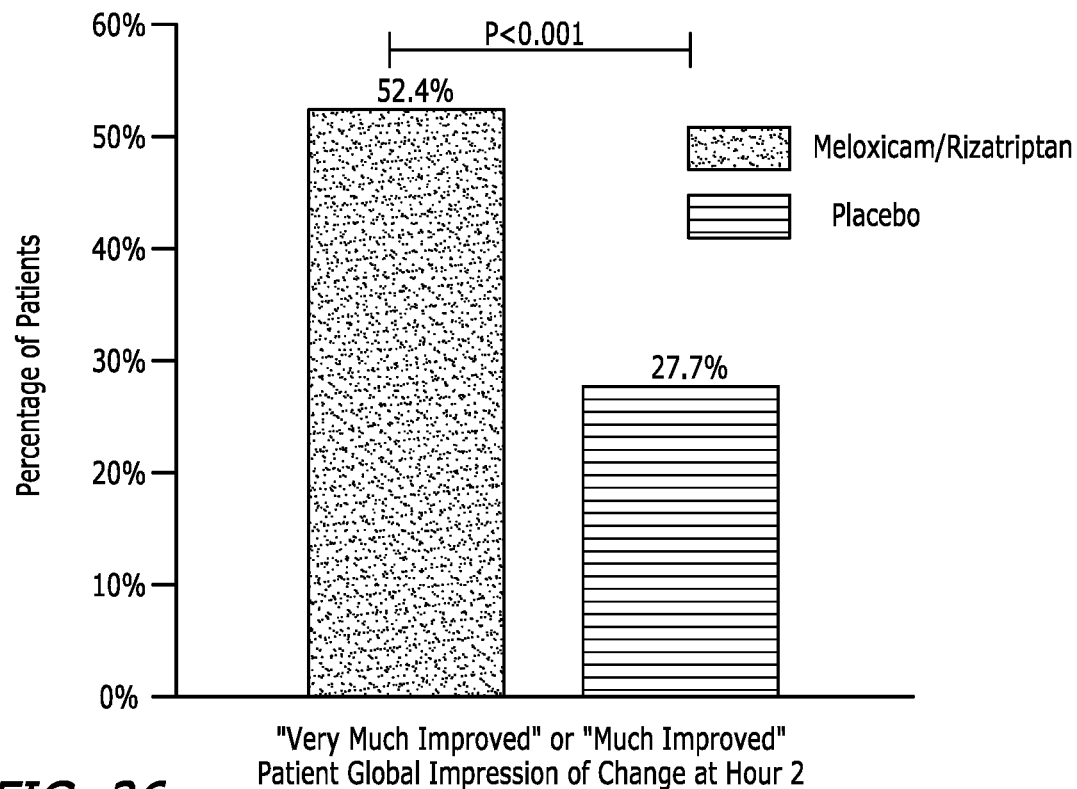
FIG. 26 shows the percentage of subjects having a Patient Global Impression of Change (PGI-C) of "very much improved" or "much improved" at hour 2 for subjects taking meloxicam/rizatriptan and placebo in Example 12.

On the Patient Global Impression of Change (PGI-C) scale, 52.4% of patients taking meloxicam/rizatriptan were very much or much improved compared to 27.7% of patients taking placebo (p<0.001) at hour 2 (FIG. 26).

Meloxicam/rizatriptan was generally safe and well tolerated in the trial. The most commonly reported adverse events with meloxicam/rizatriptan were somnolence, dizziness, and paresthesia, all of which occurred at a rate of less than five percent (Table 11). There were no serious adverse events in the trial.

TABLE 11

|  | Meloxicam/Rizatriptan (N = 140) | Placebo (N = 143) |
| --- | --- | --- |
| Any Treatment-Emergent Adverse Event | 25 (17.9%) | 11 (7.7%) |
| Somnolence | 6 (4.3%) | 3 (2.1%) |
| Dizziness | 4 (2.9%) | 2 (1.4%) |
| Paraesthesia | 3 (2.1%) | 0 |

Data presented as number of subjects (% of subjects)

"[This] study demonstrated high rates of freedom from migraine pain with meloxicam/rizatriptan treatment, and utilized an innovative design to evaluate migraine pain progression. It is remarkable that early treatment with meloxicam/rizatriptan prevented migraine pain progression in the vast majority of patients and enabled a similarly high percentage of patients to return to normal functioning," said Dr. Stewart Tepper, Professor of Neurology at the Geisel School of Medicine at Dartmouth. "The multiple mechanisms of meloxicam/rizatriptan address the many disordered physiological processes implicated in migraine attacks. These results, coupled with previous clinical data showing superiority of meloxicam/rizatriptan over an active comparator, provide clinical evidence that this synergistic, multi-mechanistic approach and the rapid absorption of meloxicam/rizatriptan may translate to important benefits for a wide range of patients. As clinicians continue to seek options for their patients with improved efficacy over currently available therapies, meloxicam/rizatriptan may offer an important new treatment for this disabling condition."

This Phase 3 trial confirmed the superior and durable efficacy of meloxicam/rizatriptan. The prevention of migraine pain progression, and the substantial increase in the rate of pain freedom demonstrated with early treatment with meloxicam/rizatriptan, expands and enhances its differentiated profile for the acute treatment of migraine. With this Phase 3 trial and the Phase 3 trial described in Example 11 in patients with a history of inadequate response to prior acute treatments, meloxicam/rizatriptan has now been evaluated in two positive well-controlled trials. These trials demonstrated the efficacy of meloxicam/rizatriptan against potent active and placebo comparators, across a spectrum of migraine attack settings, regardless of the timing of migraine treatment, disease severity, or baseline pain intensity.

"Migraine is one of the most disabling disorders, incapacitating sufferers and seriously damaging home life, social activity and the ability to work. Published surveys have underscored that patients remain dissatisfied with the efficacy of currently available therapies," said Cedric O'Gorman, M D, Senior Vice President of Clinical Development and Medical Affairs of Axsome. "The results of [this] trial demonstrate for the first time that meloxicam/rizatriptan can halt migraine pain progression before reaching moderate or severe intensity. These data grow the body of clinical evidence in support of the potential of meloxicam/rizatriptan to be a multi-mechanistic treatment for migraine with efficacy that is superior to the current standard of care, and which can rapidly, robustly, and durably alleviate symptoms, and return patients to their normal daily activities."

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of relieving migraine pain, comprising: orally administering to a human being in need thereof, a combination of: 1) a complex of a meloxicam and a sulfobutylether-β-cyclodextrin, 2) a bicarbonate, and 3) a rizatriptan, wherein the combination is orally administered when the human being is suffering from moderate to severe migraine pain of an acute migraine, and wherein one hour after the combination is orally administered, the human being experiences a greater reduction in migraine pain than the human being would experience one hour after the same amount of the meloxicam is orally administered alone.

2. The method of claim 1, wherein one hour after the combination is orally administered, the human being experiences a greater reduction in migraine pain than the human being would experience one hour after the same amount of the rizatriptan is orally administered alone.

3. The method of claim 1, wherein two hours after the combination is orally administered, the human being experiences a greater reduction in the human being's most bothersome symptom than the human being would experience two hours after the same amount of the rizatriptan is orally administered alone, and wherein the most bothersome symptom is nausea, phonophobia, or photophobia.

4. The method of claim 1, wherein twenty four hours after the combination is orally administered, the human being experiences a greater reduction in migraine pain than the human being would experience twenty four hours after the same amount of the rizatriptan is orally administered alone.

5. The method of claim 1, wherein the human being has a history of inadequate response to prior migraine treatments.

6. The method of claim 1, wherein the human being is selected for having a history of inadequate response to prior migraine treatments.

7. The method of claim 1, wherein the human being has had an average of about 2 to about 8 moderate to severe migraine attacks per month.

8. The method of claim 1, wherein the human being is selected for having an average of about 2 to about 8 moderate to severe migraine attacks per month.

9. The method of claim 1, wherein 1) the complex of the meloxicam and the sulfobutylether-β-cyclodextrin, 2) the bicarbonate, and 3) the rizatriptan, are combined together in a monolayer tablet.

10. The method of claim 1, wherein the combination contains: about 10 mg of rizatriptan in the free base form or a molar equivalent of a salt form; about 20 mg of meloxicam in the free base form, or a molar equivalent of a salt form; and about 400 mg to about 600 mg of the bicarbonate.

11. The method of claim 10, wherein the bicarbonate is sodium bicarbonate.

12. The method of claim 10, wherein thirty minutes after the combination is orally administered, the human being experiences a greater reduction in migraine pain than the human being would experience thirty minutes after the same amount of the rizatriptan is orally administered alone.

13. The method of claim 12, wherein the human being has a history of inadequate response to prior migraine treatments.

14. The method of claim 12, wherein the human being is selected for having a history of inadequate response to prior migraine treatments.

15. The method of claim 12, wherein 1) the complex of the meloxicam and the sulfobutylether-β-cyclodextrin, 2) the bicarbonate, and 3) the rizatriptan, are combined together in a monolayer tablet.

16. The method of claim 12, wherein twenty four hours after the combination is orally administered, the human being experiences a greater reduction in migraine pain than the human being would experience twenty four hours after the same amount of the rizatriptan is orally administered alone.

17. The method of claim 1, wherein the human being does not take any rescue medication for at least twenty four hours after the combination is orally administered.

18. The method of claim 1, wherein the human being achieves pain freedom one hour after the combination is orally administered.

19. The method of claim 1, wherein the human being achieves absence of the most bothersome symptom to the human being at two hours after the combination is orally administered, and wherein the most bothersome symptom is nausea, phonophobia, or photophobia.

20. The method of claim 1, wherein the complex of the meloxicam and the sulfobutylether-β-cyclodextrin are present in a dosage form with the bicarbonate, and the bicarbonate is present in an amount that is effective to increase the dissolution rate of meloxicam.

21. The method of claim 1, wherein the human being has migraine pain that is accompanied with nausea.

22. The method of claim 21, wherein at two hours after the combination is orally administered, the human being experiences a greater reduction in nausea than the human being would experience two hours after the same amount of the rizatriptan is orally administered alone.

23. The method of claim 1, wherein the bicarbonate is sodium bicarbonate.

24. The method of claim 1, wherein the meloxicam is in the free base form.

25. The method of claim 1, wherein the rizatriptan is rizatriptan benzoate.

26. The method of claim 1, wherein the complex of the meloxicam and the sulfobutylether-β-cyclodextrin, the bicarbonate, and the rizatriptan are present in a single dosage form.

27. The method of claim 1, wherein migraine pain is accompanied by disturbed vision.

28. The method of claim 27, wherein the human being achieves absence of the disturbed vision at two hours after the combination is orally administered.

\* \* \* \* \*